United States Patent [19]

Hillemann

[11] Patent Number: 4,588,432

[45] Date of Patent: May 13, 1986

[54] HERBICIDAL SELENYLSULFONAMIDES

[75] Inventor: Craig L. Hillemann, Wilmington, Del.

[73] Assignee: E. I. Du Pont De Nemours and Company, Wilmington, Del.

[21] Appl. No.: 680,949

[22] Filed: Dec. 11, 1984

Related U.S. Application Data

[63] Continuation-in-part of Ser. No. 583,975, Feb. 27, 1984, abandoned.

[51] Int. Cl.$^4$ .................... C07D 239/46; A01N 47/36
[52] U.S. Cl. .......................................... 71/92; 71/90; 71/93; 544/208; 544/209; 544/211; 544/212; 544/253; 544/278; 544/320; 544/321; 544/323; 544/324; 544/331; 544/332

[58] Field of Search ................... 71/92, 90; 544/321, 544/332, 331, 253, 278, 320, 323, 324

[56] References Cited

FOREIGN PATENT DOCUMENTS 107979  5/1984  European Pat. Off. ................ 71/92

*Primary Examiner*—Robert Gerstl

[57] ABSTRACT

Novel sulfonylurea compounds containing a selenoalkyl substituent such as N-[[4-methoxy-6-(methylselenyl)pyrimidin-2-yl]aminocarbonyl]-2-methylsulfonylbenzenesulfonamide and N-](4-methoxy-6-methyl-1,3,5-triazine-2-yl)aminocarbonyl]-2-methylselenylbenzenesulfonamide, suitable agricultural compositions containing these compounds, and their method-of-use as pre-emergence and post-emergence herbicides or plant growth regulators are disclosed.

15 Claims, No Drawings

HERBICIDAL SELENYLSULFONAMIDES

RELATED APPLICATIONS

This application is a continuation-in-part of Ser. No. 583,975, filed Feb. 27, 1984, and now abandoned.

BACKGROUND OF THE INVENTION

The invention relates to novel sulfonylurea compounds with a selenium-containing substituent on the heterocyclic portion or on the aromatic portion of the sulfonylurea.

U.S. Pat. No. 4,127,405 issued Nov. 28, 1978, and U.S. Pat. No. 4,169,719 issued Oct. 2, 1979 disclose herbicidal benzenesulfonylureas.

Herbicidal benzenesulfonylureas bearing ortho-carboxy groups are disclosed in U.S. Pat. No. 4,383,113, issued May 10, 1983.

Herbicidal thiophene sulfonylureas are disclosed in European Patent Application No. (EP-A) 30,142. Herbicidal naphthylsulfonylureas are disclosed in U.S. Pat. No. 4,370,479, issued Jan. 25, 1983. Herbicidal pyridine sulfonylureas are disclosed in EP-A No. 13,480.

SUMMARY OF THE INVENTION

This invention relates to novel compounds of Formula I and novel compounds of Formula II, suitable agricultural compositions containing them, and their method-of-use as general and/or selective pre-emergence and/or post-emergence herbicides or plant growth regulants.

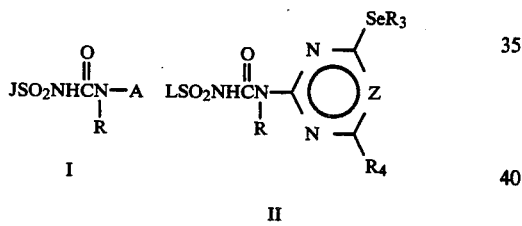

where
for the compounds of Formula I
R is H or $CH_3$;
J is

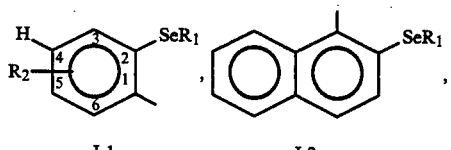

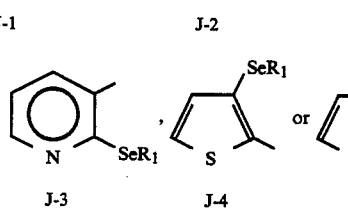

$R_1$ is $C_1$-$C_4$ alkyl, $C_3$-$C_4$ alkenyl, $C_3$-$C_4$ alkynyl, $CF_2H$ or $CH_2CH_2OCH_3$;

$R_2$ is H, $C_1$-$C_3$ alkyl, $C_1$-$C_3$ haloalkyl, halogen, nitro, $SeR_1$, $C_1$-$C_3$ alkoxy, $SO_2NR^IR^{II}$, $C_1$-$C_3$ alkylthio, $C_1$-$C_3$ alkylsulfinyl, $C_1$-$C_3$ alkylsulfonyl or $CO_2R^{III}$;

$R^I$ is H, $C_1$-$C_4$ alkyl, $C_2$-$C_3$ cyanoalkyl, methoxy or ethoxy;

$R^{II}$ is H, $C_1$-$C_4$ alkyl or $C_3$-$C_4$ alkenyl; or $R^I$ and $R^{II}$ may be taken together as $-(CH_2)_3-$, $-(CH_2)_4-$, $-(CH_2)_5-$ or $-CH_2CH_2OCH_2CH_2-$;

$R^{III}$ is $C_1$-$C_4$ alkyl, $C_3$-$C_4$ alkenyl, $C_3$-$C_4$ alkynyl, $C_2$-$C_4$ haloalkyl, $C_1$-$C_3$ cyanoalkyl, $C_5$-$C_6$ cycloalkyl, $C_4$-$C_7$ cycloalkylalkyl or $C_2$-$C_4$ alkoxyalkyl;

A is

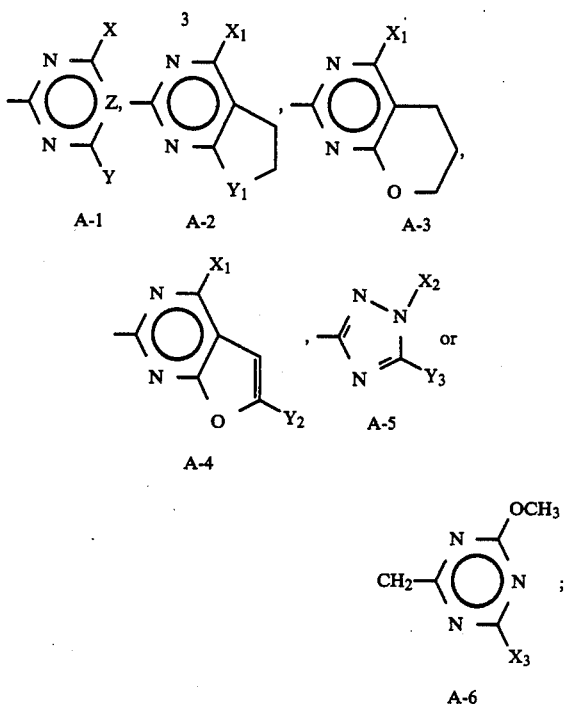

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino or di($C_1$-$C_3$ alkyl)amino;

Y is H, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino, di($C_1$-$C_3$-alkyl)amino, $C_3$-$C_4$ alkenyloxy, $C_3$-$C_4$ alkynyloxy, $C_2$-$C_5$ alkylthioalkyl, $C_1$-$C_4$ haloalkyl, $C_3$-$C_5$ cycloalkyl, $C_2$-$C_4$ alkynyl,

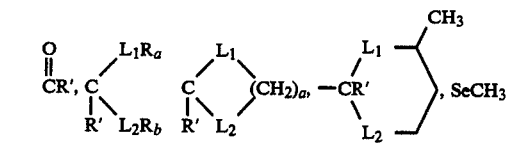

or $N(OCH_3)CH_3$;
a is 2 or 3;
$L_1$ is O or S;
$L_2$ is O or S;
$R_a$ is $C_1$-$C_2$ alkyl;
$R_b$ is $C_1$-$C_2$ alkyl;
$R'$ is H or $CH_3$;
Z is CH or N;
$Y_1$ is $CH_2$ or O;

$X_1$ is $CH_3$, $OCH_3$, $OCH_2CH_3$ or $OCF_2H$;
$Y_2$ is H or $CH_3$;
$X_2$ is $CH_3$, $CH_2CH_3$ or $CH_2CF_3$;
$Y_3$ is $OCH_3$, $OCH_2CH_3$, $SCH_3$, $CH_3$ or $CH_2CH_3$;
$X_3$ is $CH_3$ or $OCH_3$;

(1) provided that when X is Cl, F or Br, then Z is CH and Y is $OCH_3$, $OCH_2CH_3$, $NH_2$, $NHCH_3$, $N(CH_3)_2$ or $OCF_2H$;

(2) when Y is $SeCH_3$, then X is $CH_3$, $OCH_3$, $OCH_2CH_3$, $OCF_2H$ or $CF_3$;

(3) when X or Y is $OCF_2H$, then Z is CH; and (4) when $R_2$ is $SeR_1$ or $CO_2R^{III}$, then it is attached to position 6 of J-1.

For the compounds of Formula II:
R is H or $CH_3$;
$R_3$ is $CH_3$, $CH_2CH_3$ or $CHF_2$;
$R_4$ is $C_1$-$C_4$ alkyl, $C_1$-$C_4$ alkoxy, $C_1$-$C_4$ haloalkoxy, Cl, $CF_3$, $NHCH_3$ or $N(CH_3)_2$;
Z is CH or N; and
L is

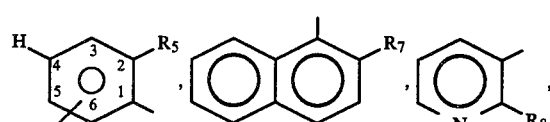

L-1, L-2, L-3

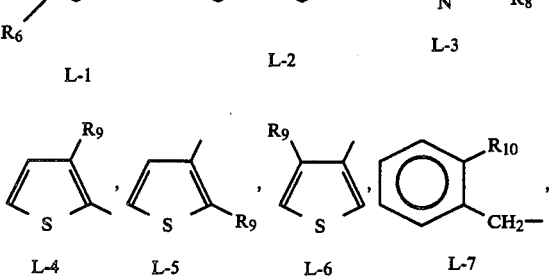

L-4, L-5, L-6, L-7

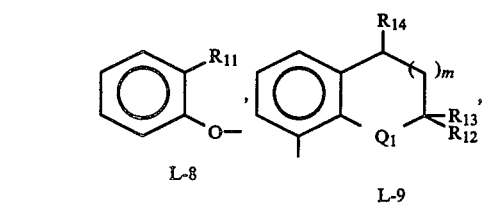

L-8, L-9

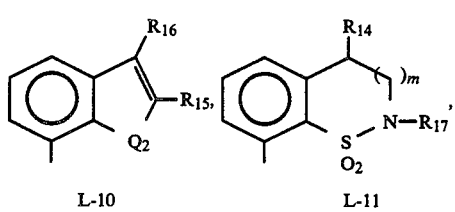

L-10, L-11

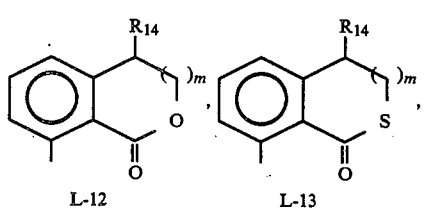

L-12, L-13

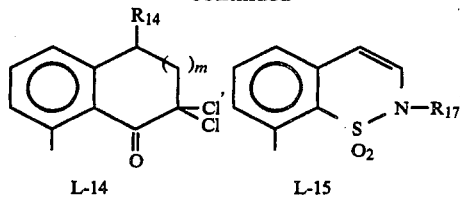

L-14, L-15

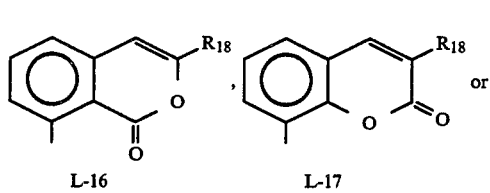

L-16, L-17

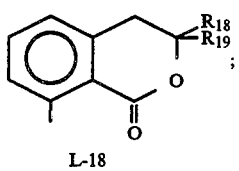

L-18

$R_5$ is $C_1$-$C_4$ alkyl, $C_1$-$C_4$ alkoxy, $OCH_2CH_2OCH_3$, $C_2$-$C_4$ haloalkenyloxy, F, Cl, Br, $NO_2$, $CF_3$, $CO_2R_{20}$, $SO_2NR_{21}R_{22}$, $SO_2N(OCH_3)CH_3$, $OSO_2R_{23}$, $S(O)_nR_{24}$, $WCF_3$, $WCHF_2$, $C_3$-$C_4$ alkenyloxy, $C_3$-$C_4$ alkynyloxy, $C_1$-$C_2$ alkyl substituted with $OCH_3$ or $OCH_2CH_3$, $C_6H_5$,

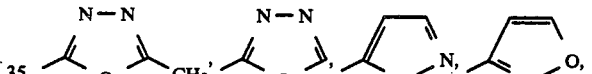

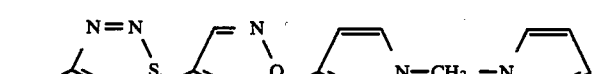

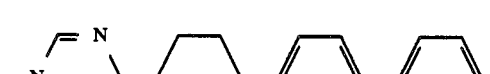

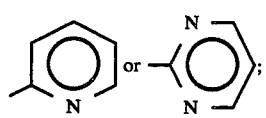

$R_6$ is H, $C_1$-$C_3$ alkyl, $C_1$-$C_3$ haloalkyl, halogen, nitro, $C_1$-$C_3$ alkoxy, $SO_2NR^IR^{II}$, $C_1$-$C_3$ alkylthio, $C_1$-$C_3$ alkylsulfinyl, $C_1$-$C_3$ alkylsulfonyl or $CO_2R^{III}$;

$R^I$ is H, $C_1$-$C_4$ alkyl, $C_2$-$C_3$ cyanoalkyl, methoxy or ethoxy;

$R^{II}$ is H, $C_1$-$C_4$ alkyl or $C_3$-$C_4$ alkenyl; or $R^I$ and $R^{II}$ may be taken together as $-(CH_2)_3-$, $-(CH_2)_4-$, $-(CH_2)_5-$ or $-CH_2CH_2OCH_2CH_2-$;

$R^{III}$ is $C_1$-$C_4$ alkyl, $C_3$-$C_4$ alkenyl, $C_3$-$C_4$ alkynyl, $C_2$-$C_4$ haloalkyl, $C_1$-$C_3$ cyanoalkyl, $C_5$-$C_6$ cycloalkyl, $C_4$-$C_7$ cycloalkylalkyl or $C_2$-$C_4$ alkoxyalkyl;

$R_7$ is H, $CH_3$, $OCH_3$, F, Cl, Br, $SO_2N(CH_3)_2$, $OSO_2CH_3$ or $S(O)_nCH_3$;

$R_8$ is $CH_3$, $CH_2CH_3$, $OCH_3$, $OCH_2CH_3$, F, Cl, Br, $SO_2NR_{21}R_{22}$, $SO_2N(OCH_3)CH_3$ or $S(O)_nR_{24}$;

$R_9$ is $C_1$-$C_3$ alkyl, F, Cl, Br, $NO_2$, $CO_2R_{20}$, $SO_2NR_{21}R_{22}$, $SO_2N(OCH_3)CH_3$ or $S(O)_nR_{24}$;

$R_{10}$ is Cl, $NO_2$, $CO_2CH_3$, $CO_2CH_2CH_3$, $SO_2N(CH_3)_2$, $OSO_2CH_3$, $SO_2CH_3$, $SO_2CH_2CH_3$, $OCH_3$ or $OCH_2CH_3$;

$R_{11}$ is Cl, Br, $NO_2$, $CH_3$, $CH_2CH_3$, $OCH_3$, $OCH_2CH_3$, $CO_2CH_3$, $CO_2CH_2CH_3$, $SO_2N(CH_3)_2$, $OSO_2R_{23}$, $SO_2CH_3$ or $SO_2CH_2CH_3$;

$R_{12}$ is H, $CH_3$ or $CH_2CH_3$;

$R_{13}$ is H, $CH_3$ or $CH_2CH_3$;

$R_{14}$ is H or $CH_3$;

$R_{15}$ is H or $CH_3$;

$R_{16}$ is H or $CH_3$;

$R_{17}$ is H or $C_1$–$C_4$ alkyl;

$R_{18}$ is H or $CH_3$;

$R_{19}$ is H or $CH_3$;

$R_{20}$ is $C_1$–$C_4$ alkyl, $CH_2CH_2OCH_3$, $CH_2CH_2Cl$ or $CH_2CH=CH_2$;

$R_{21}$ is $C_1$–$C_3$ alkyl;

$R_{22}$ is $C_1$–$C_3$ alkyl;

$R_{23}$ is $C_1$–$C_3$ alkyl or $N(CH_3)_2$;

$R_{24}$ is $C_1$–$C_3$ alkyl or $CH_2CH=CH_2$;

m is 0 or 1;

n is 0 or 2;

$Q_1$ is O, S, $SO_2$ or $NR_{18}$;

$Q_2$ is O, S, or $NR_{18}$; and

W is O, S or $SO_2$;

provided that (1) the total number of carbon atoms of $R_{21}$ and $R_{22}$ is less than or equal to four;

(2) when m is 1, then $R_{14}$ is H;

(3) when L is L-18, then $R_{18}$ and $R_{19}$ are not simultaneously H;

(4) when $R_4$ is $OCHF_2$ or Cl, then Z is CH; and (5) when $R_3$ is $CHF_2$, then Z is CH.

Preferred for their higher herbicidal activity and/or more favorable ease of synthesis are:

(1) Compounds of Formula I where:

$R_2$ is H, F, Cl, Br, $CH_3$, $CF_3$, $OCH_3$, $SCH_3$, $OCF_2H$ or $SCF_2H$;

X is $CH_3$, $OCH_3$, $OCH_2CH_3$, Cl, F, Br, $OCF_2H$, $CH_2F$ or $CF_3$; and

Y is H, $C_1$–$C_3$ alkyl, cyclopropyl, $OCH_3$, $OCH_2CH_3$, $CH_2OCH_3$, $SeCH_3$, $CH_2OCH_2CH_3$, $NH_2$, $NHCH_3$, $N(CH_3)_2$, $CF_3$, $SCH_3$, $OCH_2CH=CH_2$, $OCH_2C\equiv CH$, $OCH_2CF_3$, $OCH_2CH_2OCH_3$, $CH_2SCH_3$, $OCF_2H$, $SCF_2H$,

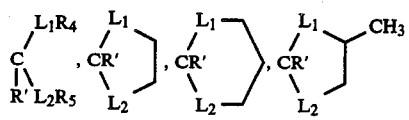

or $CR'(QCH_2CH_3)_2$;

(2) Compounds of Preferred 1 where A is A-1;

(3) Compounds of Preferred 2 where Y is $C_1$–$C_3$ alkyl, cyclopropyl, $OCH_3$, $OCH_2CH_3$, $CH_2OCH_3$, $CH_2OCH_2CH_3$, $OCH_2CF_3$ or $CH(OCH_3)_2$;

(4) Compounds of Preferred 3 where R is H and $R_1$ is $CH_3$ or $CH_2CH_3$;

(5) Compounds of Preferred 4 where J is J-1 and $R_2$ is H;

(6) Compounds of Formula II wherein $R_4$ is $CH_3$, $OCH_3$, $OCH_2CH_3$, $OCH_2CF_3$, $OCF_2H$, $CF_3$, $NHCH_3$ or $N(CH_3)_2$;

$R_6$ is H, F, Cl, Br, $CF_3$, $CH_3$, $OCH_3$, $SCH_3$ or $OCF_2H$; and $Q_2$ is O or S.

(7) Compounds of Preferred 6 where R is H, $R_3$ is $CH_3$ or $CH_2CH_3$, $R_4$ is $CH_3$, $OCH_3$ or $OCH_2CH_3$, and $R_6$ is H;

(8) Compounds of Preferred 7 where L is L-1, L-2, L-3, L-5, L-9, L-11, L-12, L-17 or L-18;

(9) Compounds of Preferred 8 where L is L-1;

$R_5$ is $OCH_3$, $OCH_2CH_3$, Cl, $NO_2$, $CF_3$, $CO_2CH_3$, $CO_2CH_2CH_3$, $SO_2N(CH_3)_2$, $SO_2N(OCH_3)CH_3$, $OSO_2R_{23}$, $S(O)_nR_{24}$, $OCF_2H$, $SCF_2H$, $OCH_2CH=CH_2$, $OCH_2C\equiv CH$,

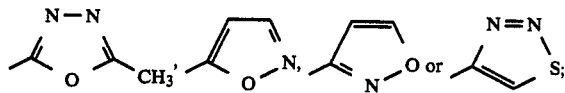

$R_{23}$ is $C_1$–$C_3$ alkyl;

$R_{24}$ is $CH_3$ or $CH_2CH_3$; and n is 2;

(10) Compounds of Preferred 8 where L is L-2 and $R_7$ is Cl, $CH_3$, $OCH_3$, $SCH_3$ or Br;

(11) Compounds of Preferred 8 where L is L-3 and $R_8$ is Cl, $SO_2CH_3$ or $SO_2N(CH_3)_2$;

(12) Compounds of Preferred 8 where L is L-5 and $R_9$ is $CO_2CH_3$ or $CO_2CH_2CH_3$;

(13) Compounds of Preferred 8 where L is L-9;

(14) Compounds of Preferred 8 where L is L-11;

(15) Compounds of Preferred 8 where L is L-12;

(16) Compounds of Preferred 8 where L is L-17; and

(17) Compounds of Preferred 8 where L is L-18.

Specifically Preferred for reasons of their highest herbicidal activity, greatest growth regulant activity and/or most favorable ease of synthesis are:

N-[[4-methoxy-6-(methylselenyl)pyrimidin-2-yl]aminocarbonyl]-2-(methylsulfonyl)benzenesulfonamide;

2-[[[4-methyl-6-(methylselenyl)pyrimidin-2-yl]aminocarbonyl]aminosulfonyl]benzoic acid, methyl ester;

2-[[[4-methoxy-6-(methylselenyl)-1,3,5-triazin-2-yl]aminocarbonyl]aminosulfonyl]benzoic acid, ethyl ester;

N-[(4,6-dimethoxypyrimidin-2-yl)aminocarbonyl]-2-methylselenylbenzenesulfonamide; and N-[(4-methoxy-6-methyl-1,3,5-triazin-2-yl)aminocarbonyl]-2-methylselenylbenzenesulfonamide.

DETAILED DESCRIPTION OF THE INVENTION

Synthesis

The compounds of Formula I and Formula II can be prepared by one or more of the following methods described below in Equations 1 to 4 and 26.

As shown in Equation 1a below, compounds of Formula I can be prepared by reacting an appropriately substituted sulfonyl isocyanate of Formula (1) with an appropriate amino or alkylamino heterocycle of Formula (2). Likewise, as shown in Equation 1b below, compounds of Formula II can be prepared by reacting an appropriately substituted sulfonyl isocyanate of Formula (3) with an appropriate 2-amino-4-selenylpyrimidine, 2-alkylamino-4-selenylpyrimidine, 2-amino-4-selenyl-1,3,5-triazine, or 2-alkylamino-4-selenyl-1,3,5-triazine of Formula (4). A, J, L, R, $R_3$ and $R_4$ are as previously defined.

Equation 1

$$JSO_2NCO + HN-A \xrightarrow{} I$$
$$\phantom{JSO_2NCO + H}|\phantom{N-A}$$
$$\phantom{JSO_2NCO + HN}R$$
$$(1) \phantom{JSO_2NCO +} (2)$$

(a)

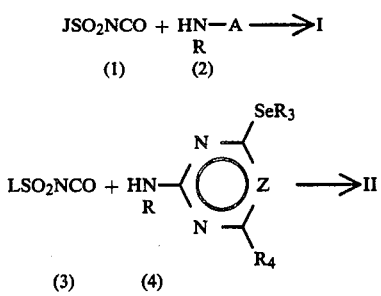

(b)

The reaction is best carried out in inert aprotic organic solvents such as dichloromethane, 1,2-dichloroethane, tetrahydrofuran, or acetonitrile, at a temperature between 20° and 85° C. The order of addition is not critical; however, it is often convenient to add the sulfonyl isocyanate or a solution of it in the reaction solvent to a stirred suspension of the amine.

Sulfonyl isocyanates (3) are generally prepared from the corresponding sulfonamides (7) (see Equations 24 and 25). In rare cases a sulfonamide may not be sufficiently stable to be useful as an intermediate. In these cases, as well as others, the requisite sulfonyl isocyanate (3) can be made and reacted with the heterocyclic amine (4) by treating the corresponding sulfonyl chloride with an isocyanate anion in the presence of the amine (see Equation 26 and accompanying discussion).

In some cases, the desired product is insoluble in the reaction solvent at ambient temperature and crystallizes from it in pure form. Products soluble in the reaction solvent are isolated by evaporation of the solvent. Compounds of Formula I and Formula II then may be purified by trituration of the evaporation residue with solvents such as 1-chlorobutane or ethyl ether and filtration, by recrystallization from mixtures of solvents such as 1,2-dichloroethane, 1-chlorobutane, and heptane or by chromatography on silica gel.

Some of the compounds of Formula I and Formula II can be prepared as shown in Equation 2a and Equation 2b respectively. Reaction of a sulfonamide of Formula (5) with an appropriate methylpyrimidinyl carbamate or methyltriazinyl carbamate of Formula (6) in the presence of at least an equimolar amount of trimethylaluminum leads to compounds of Formula I. Similarly, reaction of a sulfonamide of Formula (7) with an appropriate methylpyrimidinyl carbamate or methyltriazinyl carbamate of Formula (8) in the presence of at least an equimolar amount of trimethylaluminum leads to compounds of Formula II. A, J, L, R, R₃ and R₄ are as previously defined; however, for this method R₂ cannot be CO₂R$^{III}$, R₅ and R₉ cannot be CO₂R₂₀, R₁₀ cannot be either CO₂CH₃ or CO₂C₂H₅, and L cannot be L-8, L-12, L-16, L-17 or L-18.

Equation 2

$$JSO_2NH_2 + CH_3OCNA \xrightarrow{} I$$
$$\phantom{JSO_2NH_2 + CH_3OC}|$$
$$\phantom{JSO_2NH_2 + CH_3OCN}R$$
$$(5) \phantom{JSO_2NH_2 +} (6)$$

(a)

-continued
Equation 2

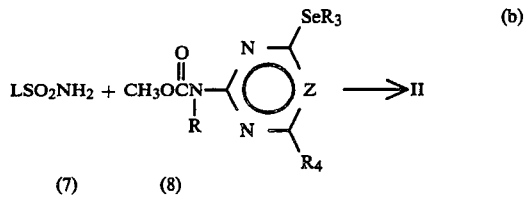

(b)

The reaction of Equation 2 is best run in either dichloromethane or 1,2-dichloroethane solution at 20° to 85° C. for 10 to 96 hours under a nitrogen or argon atmosphere. The product can be isolated by addition of an aqueous acetic acid solution followed by extraction of the product into dichloromethane, or by filtration of a product of low solubility. The product can be purified by trituration with solvents such as 1-chlorobutane or ethyl ether, by recrystallization from mixtures of solvents such as 1,2-dichloroethane, 1-chlorobutane, and heptane, or by column chromatography on silica gel.

Many of the compounds of Formula I and Formula II can be prepared by the procedures shown in Equations 3a and 3b, where A, J, L, R, R₃ and R₄ are as previously defined except that L cannot be L-8.

Equation 3

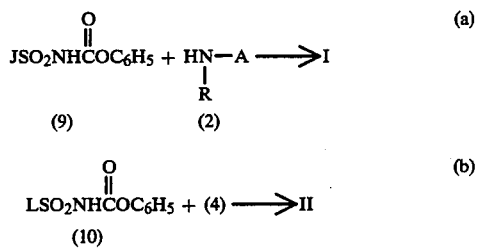

The reactions shown in Equation 3 are carried out by contacting phenylcarbamates of Formulas (9) and (10) with the aminoheterocycles of Formulas (2) and (4) in an inert organic solvent such as dioxane or tetrahydrofuran at temperatures of about 20°–100° C. for a period of about one-half to twenty-four hours. The product can be isolated by evaporation of the reaction solvent and purified by methods previously described.

Phenyl carbamates of Formulas (9) and (10) can be prepared by the methods described, or modifications thereof known to those skilled in the art, in European Patent Application No. 81810282.4 (Publ. No. 44,808), published Jan. 27, 1982; or South African Patent Application No. 825042.

Alternatively, many of the compounds of Formulas Ia and IIa can be prepared by the method described in Equations 4a and 4b, where J, L, A, R₃ and R₄ are as previously defined except that L cannot be L-8.

Equation 4

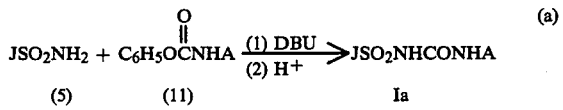

(a)

-continued
Equation 4

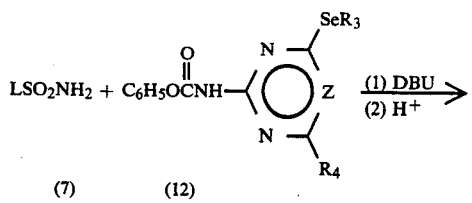
(b)

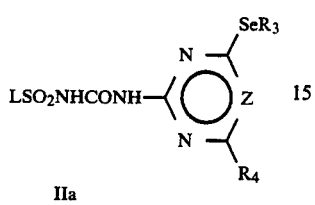
IIa

The reactions of Equations 4a and 4b can be carried out by contacting equimolar amounts of a sulfonamide of Formula (5) or (7) with a heterocyclic phenyl carbamate of Formula (11) or (12) in the presence of an equimolar amount of 1,8-diazabicyclo[5.4.0]undec-7-ene (DBU), by methods analogous to those described in South African Patent Application No. 830441. The phenyl carbamates of Formulas (11) and (12) can be prepared by methods, or modifications thereof known to those skilled in the art, described in South African Patent Application No. 825671 and South African Patent Application No. 825045.

The ortho-selenyl benzenesulfonamide intermediates (5a) can be prepared by one or more of the following general methods.

As shown in Equation 5, one highly useful general route involves aryl transmetallation-type reactions.

Equation 5

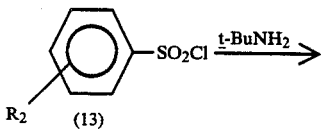
(a)

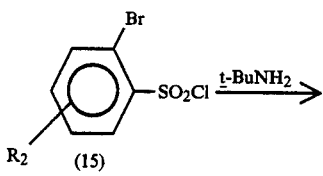
(b)

-continued
Equation 5

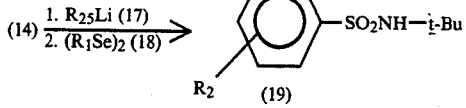
(c)

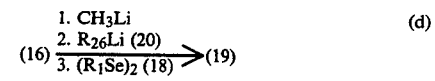
(d)

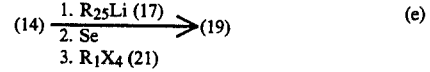
(e)

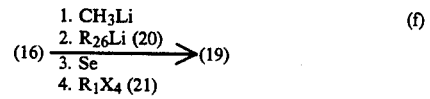
(f)

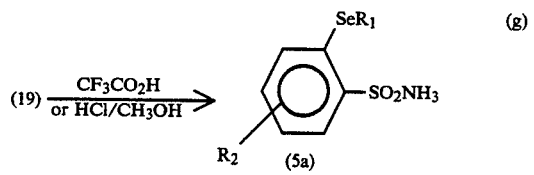
(g)

where
$R_1$ and $R_2$ are as previously defined; and
$R_{25}$ is n-Bu, t-Bu, $-N(i-C_3H_7)_2$ or

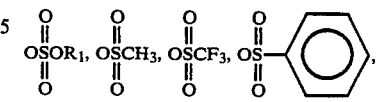

$R_{26}$ is n-Bu, s-Bu or t-Bu;
$X_4$ is Cl, Br, I,

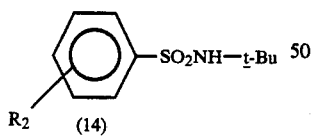

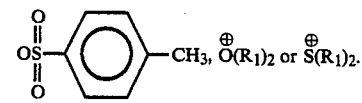

The benzenesulfonyl chlorides (13) and (15) are either known or can be prepared by a variety of obvious methods by one skilled in the art. These are converted to the corresponding N-t-butyl benzenesulfonamides (14) and (16) by treatment with at least two moles t-butylamine per mole of sulfonyl chloride in inert solvent using the general procedure described by J. G. Lombardino, *J. Org. Chem.* 36, 1843 (1971).

Benzenesulfonamide (14) is then ortholithiated according to the procedure reviewed by H. W. Gschwend and H. R. Rodriguez in *Org. React.*, 26, 1 (1979). Generally a solution of (14) in ethereal solvent, such as tetrahydrofuran or ethyl ether, at −78° C. under inert atmosphere is treated with two equivalents of $R_{25}Li$ (17)

then warmed to room temperature. The lithiated intermediate is then selenated with $(R_1Se)_2$ (18) (Equation 5c). The preparation of $(R_1Se)_2$ and use of such as a selenating agent has been reviewed (K. J. Irgolic, M. V. Kudchadker "Organic Chemistry of Selenium" in *Selenium*, R. A. Zingaro, W. C. Cooper ed., Van Nostrand Reinhold, New York, 1974).

Alternatively, the lithiated intermediate can be selenated with elemental selenium to give a lithium selenide salt which then is alkylated (Equation 5e). This selenation-alkylation sequence has been reviewed (L-B Agenas, "Selenides and their Derivatives" in *Organic Selenium Compounds, Their Chemistry and Biology*, D. L. Klayman, W. H. H. Gunther ed., Wiley-Interscience, New York, 1973).

In cases where $R_2$ is in the 3- or 5-position and lithiation of (14) gives rise to a isomeric mixture and in cases where the substituent $R_2$ itself can be lithiated, it may be more desirable to treat (16) with one equivalent of $CH_3Li$ to form the sulfonamide salt and then perform a regiospecific metal-halogen interchange using $R_{26}Li$ (20) as reviewed by B. J. Wakefield, *The Chemistry of Organolithium Compounds*, Pergamon, N.Y., 1974. The ortholithium reagent can then be either treated with $(R_1Se)_2$ (18) (Equation 5d) or with selenium followed by $R_1X_4$ (21) (Equation 5f) to give (19) as described above.

Finally the tert-butyl group of (19) is removed to give (5a) by stirring in trifluoroacetic acid or in methanol containing at least one equivalent of hydrogen chloride, followed by rotary evaporation (Equation 5g).

In a few cases obvious to those trained in the art, $R_2$ may be of a nature and/or be in a position to prevent the desired ortho-lithium reagent derived from (14) or (16) from being formed or to cause it to be unstable. In these cases, as well as others, sulfonamide (5a) can be prepared as depicted in Equation 6.

Equation 6

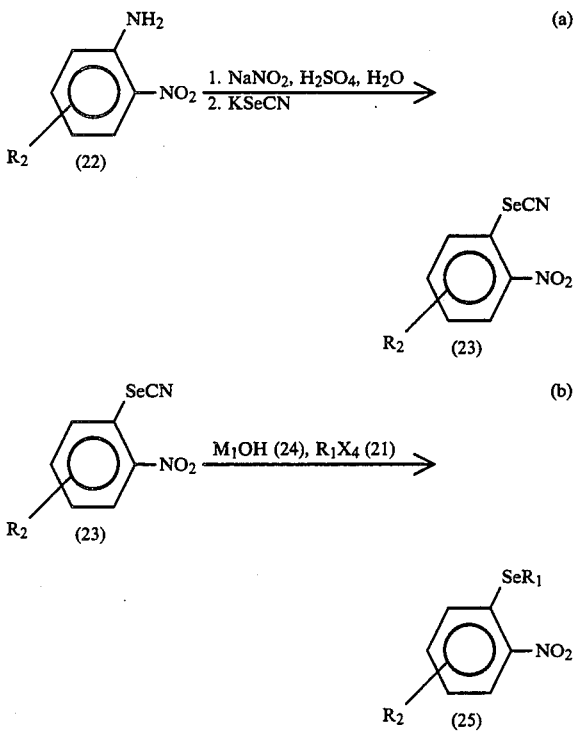

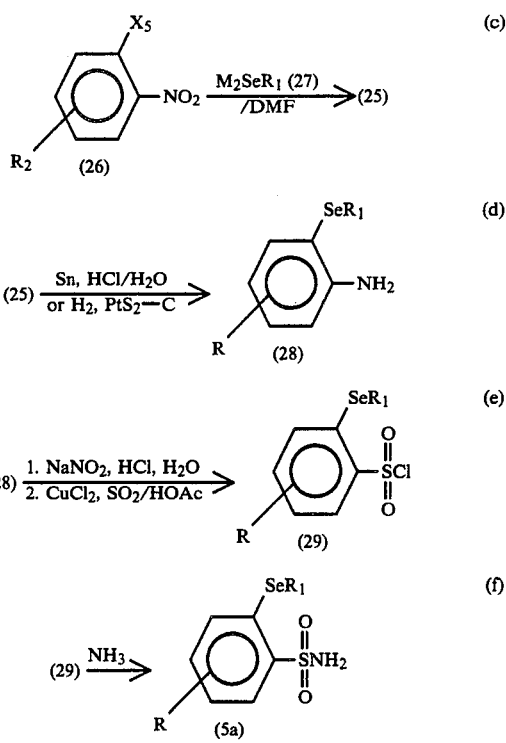

where
$R_1$, $R_2$ and $X_4$ are as previously defined,
$M_1$ is Na or K,
$M_2$ is Li, Na or K, and
$X_5$ is F, Cl or Br.

The nitroanilines (22) may be prepared by a wide variety of methods known in the art. These may be diazotized and the diazonium salts reacted with potassium selenocyanate to give (23) (Equation 6a) as has been reviewed (D. L. Klayman, "Selenols and their Derivatives" in *Organic Selenium Compounds: Their Chemistry and Biology*, D. L. Klayman, W. H. H. Gunther ed., New York, 1973). The selenocyanates (23) are then cleaved with base in the presence of $R_1X_4$ (21) as reviewed by L-B Agenas (op. cit.) to give (25) (Equation 6b).

Alternatively, the halonitro compounds (26), preferable by a wide variety of methods known in the art, may be selenated to give (25) where $R_1$ is not $CHF_2$ through the use of at least one equivalent of $M_2SeR_1$ (27) dissolved in a polar solvent such as N,N-dimethylformamide at a temperature between 20° and 150° C. (Equation 6c). The alkali metal selenides $M_2SeR_1$ (27) can be conveniently prepared by in situ combination of an alkyl metal tert-butoxide, $M_2O$-t-Bu, with the selenol $HSeR_1$ in the solvent to be used for the displacement reaction. The selenols $HSeR_1$ in turn can be prepared by a variety of methods reviewed by D. L. Klayman (op. cit.) and K. J. Irgolic and M. V. Kudchadker (op. cit.).

The nitrobenzene (25) is then reduced to the aniline (28) either by use of tin in hydrochloric acid as reviewed by K. J. Irgolic and M. V. Kudchadker (op. cit.) or by hydrogenation using platinum sulfide as catalyst and the conditions of F. S. Dovel and H. Greenfield, *J. Am. Chem. Soc.*, 87, 2767 (1965) (Equation 6d).

The aniline (28) is converted to the sulfonyl chloride (29) using the general procedures of H. Meerwein, G. Dittmar, R. Gollner, K. Hafner, F. Mensch, O. Steinfort, *Chem. Ber.*, 90 841 (1957) (Equation 6e). Finally the sulfonyl chloride (29) is aminated to give (5a) using at least two equivalents of ammonia in ether, tetrahydrofuran, or dichloromethane solution at a temperature between −30° and +30° C.

The ortho-selenyl naphthalenesulfonamide intermediates (5b) are prepared by the following method.

Equation 7

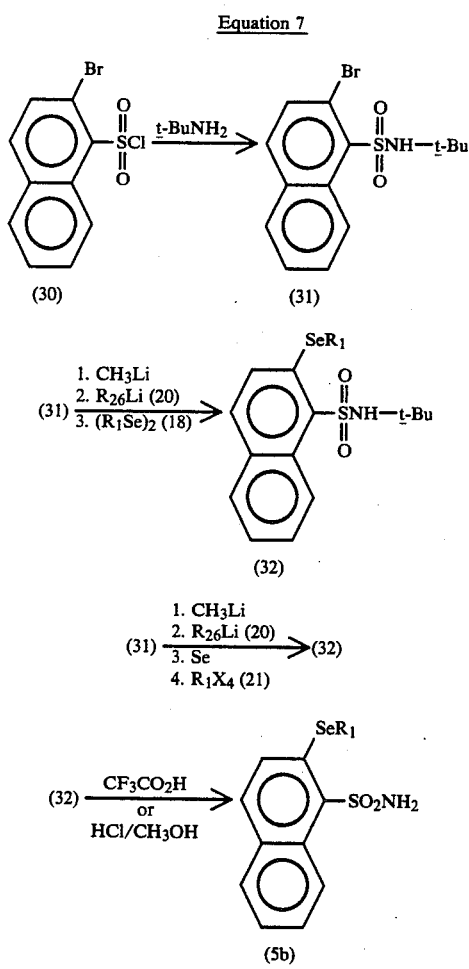

where $R_1$, $R_{26}$ and $X_4$ are as previously defined.

The sulfonyl chloride (30) (M. Janczewski, *Roczniki Chem.*, 39, 391 (1965); *Chem. Abst.*, 63, 16246c (1965)) is converted to the sulfonamide (31) by treatment with at least two equivalents of t-butylamine in inert solvent using the general procedure described by J. G. Lombardino (op. cit.) (Equation 7a).

The sulfonamide (31) is treated with one equivalent of $CH_3Li$ to form the sulfonamide salt, and then a regiospecific metal-halogen interchange is performed using $R_{26}Li$ (20) as reviewed by B. J. Wakefield (op. cit.). The organolithium reagent can then be either treated with $(R_1Se)_2$ (18) (Equation 7b) or with selenium followed by $R_1X_4$ (21) (Equation 7c) to give (32) analogous to the preparation of (19) via Equations 5d and 5f already described.

The tert-butyl group of (32) is removed to give (5b) by stirring in trifluoroacetic acid or in methanol containing at least one equivalent of hydrogen chloride, followed by rotary evaporation (Equation 7d).

The ortho-selenyl pyridinesulfonamide intermediates (5c) are prepared by one or more of the following general methods.

Equation 8

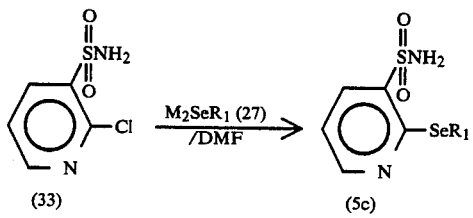

where $M_2$ and $R_1$ are as previously defined.

Sulfonamide (33) (well known in the art) is condensed with at least one equivalent of an alkali metal selenide $M_2SeR_1$ (27) in a polar solvent like N,N-dimethylformamide at 20° to 150° C. to give sulfonamide (5c). The selenides $M_2SeR_1$ (27) are prepared as has been previously described.

Alternatively the pyridinesulfonamide intermediates (5c) can be prepared by Equation 9.

Equation 9

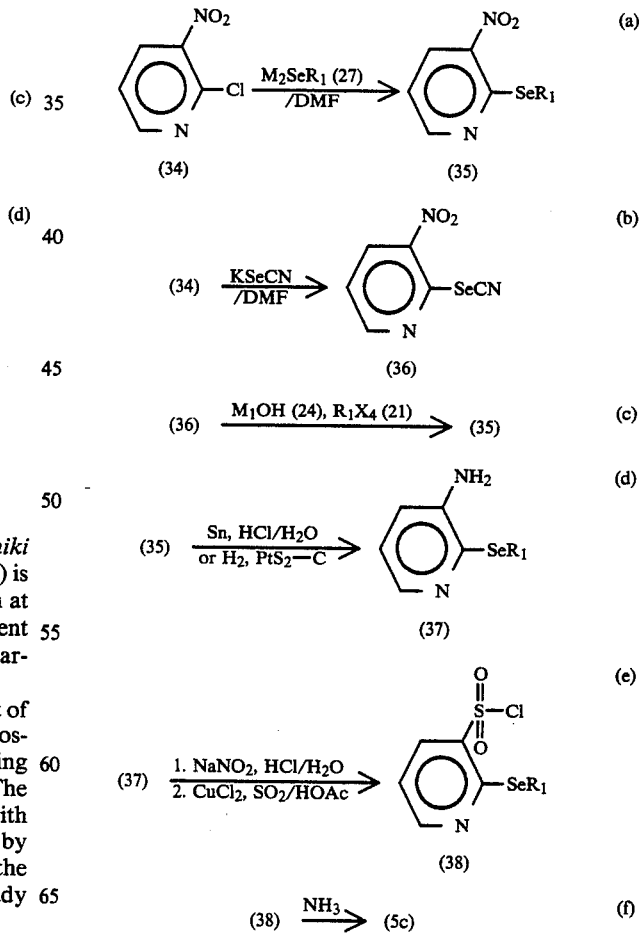

where $R_1$, $M_1$, $M_2$ and $X_4$ are as previously defined.

In Equation 9a, chloronitropyridine (34) (well known in the art) is treated with at least one equivalent of an alkali metal selenide $M_2SeR_1$ (27) in a polar solvent such as N,N-dimethylformamide at a temperature between 20° and 150° C. to give the selenyl compound (35).

Alternatively, (34) may be converted to the selenocyanate (36) through the use of at least one equivalent of potassium selenocyanate in a polar aprotic solvent such as N,N-dimethylformamide at 20°–150° C. (Equation 9b). The selenocyanate (36) is then cleaved with base in the presence of $R_1X_4$ (21) as reviewed by L-B. Agenas (op. cit.) to give (35) (Equation 9c). This alternative sequence is of special importance when $R_1$ is $CHF_2$, since $M_2SeCHF_2$ is unknown and probably unstable.

The nitro selenide (35) is then reduced to the amino derivative (37) (Equation 9d), converted to the sulfonyl chloride (38) (Equation 9e), and aminated to give sulfonamide (5c) (Equation 9f) using the same basic conditions already noted for Equations 6d, 6e and 6f respectively.

The ortho-selenyl thiophenesulfonamide intermediates (5d) are prepared by one or more of the following general methods.

Equation 10

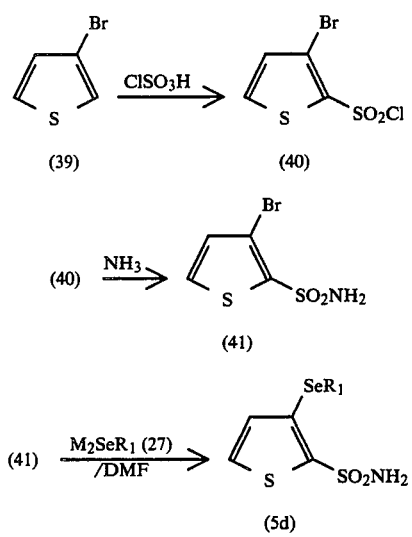

where $M_2$ and $R_1$ are as previously defined.

3-Bromothiophene (39), well known in the art, dissolved in a suitable unreactive solvent such as dichloromethane or tetrachloromethane at 0°–5° C. is treated with five equivalents of chlorosulfonic acid. After one hour the chlorosulfonation mixture is poured slowly into ice-water. The halocarbon layer is separated, washed with saturated aqueous sodium bicarbonate, dried over magnesium sulfate, and rotary evaporated to afford sulfonyl chloride (40) (Equation 10a). The sulfonyl chloride (40) is then aminated using at least two equivalents of ammonia in ether, tetrahydrofuran, or dichloromethane solution at a temperature between −30° and +30° C. to give sulfonamide (41). Finally, (41) is treated with at least one equivalent of an alkali metal selenide $M_2SeR_1$ (27) in a polar solvent such as N,N-dimethylformamide at a temperature between 20° and 150° C. to give the selenyl sulfonamide (5d) (Equation 10c).

Alternatively, in some cases the following route may be employed.

Equation 11

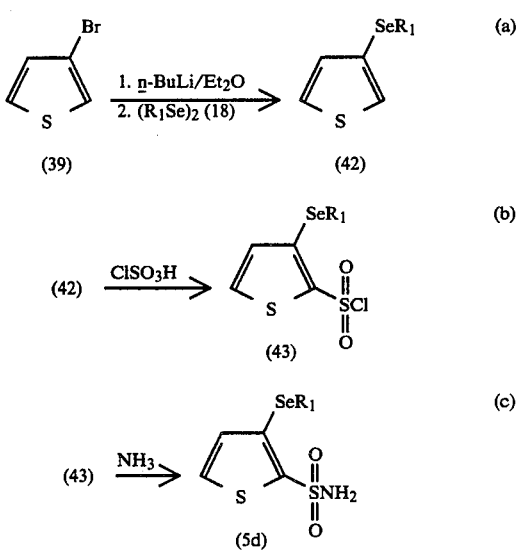

where $R_1$ is $C_1$–$C_4$ alkyl, $CF_2H$, and $CH_2CH_2OCH_3$.

A solution of 3-bromothiophene in ethyl ether at a temperature between −70° and −80° C. is treated with one equivalent of n-butyllithium followed by one equivalent of $(R_1Se)_2$ (18). The mixture is warmed to room temperature, washed with dilute aqueous hydrochloric acid, dried over magnesium sulfate, and rotary evaporated to afford (42) (Equation 11a).

A solution of (42) in dichloromethane at a temperature between −30° and +5° C. is treated with at least two equivalents of chlorosulfonic acid. After one hour the reaction mixture is poured into ice-water. The dichloromethane layer is separated, washed with aqueous sodium bicarbonate, dried over magnesium sulfate, and the solvent is evaporated to yield the sulfonyl chloride (43) (Equation 11b). This is aminated using at least two equivalents of ammonia in ether, tetrahydrofuran, or dichloromethane solution at a temperature between −30° and +30° C. to give sulfonamide (5d) (Equation 11c).

The ortho-selenyl thiophenesulfonamide intermediates (5e) are prepared by the following general method.

Equation 12

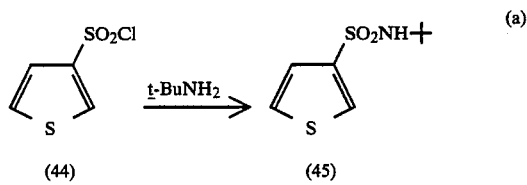

-continued
Equation 12

(b)
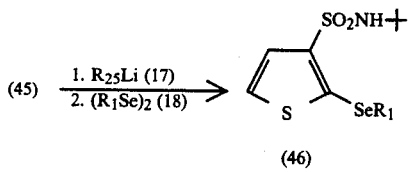

(c)
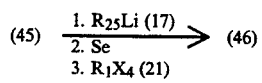

(d)
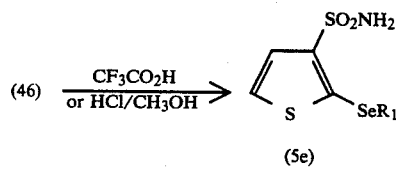

where
$R_1$, $R_{25}$ and $X_4$ are as previously defined.

The 3-thiophenesulfonyl chloride (44) is well known in the art. It is converted to the corresponding N-t-butyl sulfonamide (45) by treatment with at least two equivalents of tert-butylamine in inert solvent using the general procedure described by J. G. Lombardino (op. cit.) (Equation 12a).

Thiophenesulfonamide (45) is then lithiated at the 2-position and reacted either with $(R_1Se)_2$ (18) (Equation 12b) or with elemental selenium followed by the alkylating agent $R_1X_4$ (21) (Equation 12c) to give (46) according to the general procedure already discussed for the conversion of (14) to (19) (Equations 5c and 5e). Finally the t-butylsulfonamide (46) is stirred in either trifluoroacetic acid or in methanol containing at least one equivalent of hydrogen chloride, followed by rotary evaporation to afford the free sulfonamide (5e) (Equation 12d).

Sulfonyl isocyanates (1) are prepared from the corresponding sulfonamides (5) by one of the following two general methods.

Equation 13

$$JSO_2NH_2 \xrightarrow[COCl_2, \text{ cat}]{CH_3(CH_2)_3NCO} JSO_2NCO$$

(5) (1)

where
J is as previously defined and (5) is (5a), (5b), (5c), or (5d).

The sulfonamide (5) and an alkyl isocyanate (e.g., n-butyl isocyanate) in xylene or other solvent boiling above 135° C. are mixed in the presence or absence of a catalytic amount of 1,4-diaza[2.2.2]bicyclooctane (DABCO) and heated to 135°-140° C. After 5-60 minutes phosgene is slowly added to the heated mixture at such a rate that the temperature remains between 133° and 135° C. When the consumption of phosgene has ceased, the mixture is cooled and filtered to remove insoluble material. Finally, the solvent, alkyl isocyanate, and excess phosgene are evaporated, leaving the sulfonyl isocyanate (1).

If desired, the alkyl isocyanate-sulfonamide adduct can be made and isolated before reaction with the phosgene. In this case the sulfonamide (5), alkyl isocyanate, and anhydrous base (e.g., $K_2CO_3$) in a polar, aprotic solvent (e.g., acetone, butanone, or acetonitrile) are mixed and heated under reflux for 1 to 6 hours. The reaction mixture is then diluted with water, and the pH is adjusted to about 3 with acid (e.g. HCl, $H_2SO_4$). The adduct is filtered out and dried, and then reacted with phosgene as described above. This procedure modification is especially useful when sulfonamide (5) is high melting and has low solubility in the phosgenation solvent.

Sulfonyl isocyanates (1) can also be prepared by the following method.

Equation 14

$$JSO_2NH_2 \xrightarrow{SOCl_2} JSO_2NSO \quad (a)$$

(5) (47)

$$(47) \xrightarrow[\text{pyridine cat.}]{COCl_2,} JSO_2NCO \quad (b)$$

(1)

where
J is as previously defined and (5) is (5a), (5b), (5c), or (5d).

The sulfonamide (5) is heated at reflux in an excess of thionyl chloride. The reaction is continued until the sulfonamide protons are no longer detectable in the proton magnetic resonance spectrum. From 16 hours to 5 days is typically sufficient for complete conversion to the thionylamide (47) (Equation 14a).

The thionyl chloride is evaporated and the residue is treated with an inert solvent (e.g. toluene) containing at least one equivalent (typically 2-3 equivalents) of phosgene. A catalytic amount of pyridine (typically 0.1 equivalent) is added, and the mixture is heated to about 60°-140° C., with 80°-100° preferred. Conversion to the isocyanate (1) is usually substantially complete within 15 minutes to 3 hours (Equation 14b). The mixture is then cooled and filtered, and the solvent is evaporated, leaving the sulfonyl isocyanate (1).

Amino and methylamino pyrimidines and s-triazines of general structure (4) are made by one or more of the following general methods.

Equation 15

$$\underset{(48)}{\text{HN}(R)\text{-ring}(X_5, Z, R_4)} \xrightarrow{M_3SeR_3 \,(49)} \underset{(4)}{\text{HN}(R)\text{-ring}(SeR_3, Z, R_4)}$$

where
R, $R_3$, $R_4$ and Z are as previously defined, except that $R_3$ cannot be $CHF_2$, and where $M_3$ is Li, Na, or K and $X_5$ is F, Cl, Br or I.

The amino and methylamino pyrimidines and s-triazines (48) are either known or can be prepared via obvious methods by one skilled in the art. Many of the methods are reviewed in *The Chemistry of Heterocyclic Compounds,* Vol. 13 and 16, Wiley-Interscience, New York (1959 and 1962). For the preparation of amino and methylamino s-triazines the article of F. C. Schaefer and K. R. Huffman, *J. Org. Chem.*, 28, 1812 (1963) should also be consulted.

The heterocycle (48) is treated with at least one equivalent (only one equivalent if $R_4$ is displaceable) of $M_3SeR_3$ (49) in a suitable inert solvent (e.g. tetrahydrofuran, glyme, diglyme or N,N-dimethylformamide at a temperature between 20° and 80° C. for 1-18 hours. The reaction mixture is then poured into excess dichloromethane and filtered. The solvent is evaporated, leaving the heterocycle (4).

The alkali metal selenides $M_3SeR_3$ (49) can be prepared by reaction of the tert-butoxides $M_3O$-t-Bu with the appropriate selenols $HSeR_3$ in the solvent to be used for the displacement reaction. A particularly convenient preparation of $LiSeR_3$ involves the treatment of the diselenide $R_3SeSeR_3$ in tetrahydrofuran solution at 20°-30° C. with one equivalent of n-butyllithium. The selenols $HSeR_3$ and diselenides $R_3SeSeR_3$ can in turn be prepared by a variety of methods reviewed by K. J. Irgolic and M. V. Kudchaker (op. cit.) and D. J. Klayman (op. cit.).

Alternatively, the selenium-bearing substituent may be attached before the amino or methylamino substituent.

Equation 16

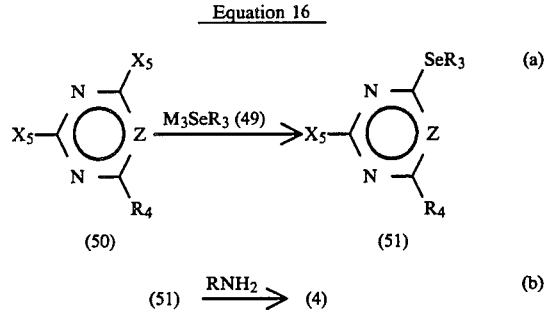

where $M_3$, R, $R_3$, $R_4$, $X_5$ and Z are as previously defined; and $R_3$ is not $CHF_2$.

When Z is CH this method may give isomeric mixtures, and so in this case the method depicted in Equation 15 is generally preferred.

The pyrimidines and s-triazines (50) are either known or can be prepared via obvious methods by one skilled in the art. For a review of many of the methods, one should consult *The Chemistry of Heterocyclic Compounds*, Vol. 13 and 16 (op. cit.) and F. C. Schaefer and K. R. Huffman (op. cit.).

The heterocycle (50) is treated with one equivalent of $M_3SeR_3$ (49) in a suitable inert solvent (e.g. tetrahydrofuran, glyme, diglyme, or N,N-dimethylformamide) at a temperature between 20° and 80° C. for 1-6 hours (Equation 16a). The reaction mixture is then poured into excess dichloromethane, washed with a little water, dried over magnesium sulfate, and filtered. The solvent is evaporated, leaving the selenide (51). Further purification may be accomplished by recrystallization or column chromatography on silica gel. The preparation of the alkali metal selenides $M_3SeR_3$ (49) has already been discussed with Equation 15.

The selenide (51) is then treated with at least two equivalents of ammonia (R=H) or methylamine (R=$CH_3$) in a suitable inert solvent (e.g. tetrahydrofuran, glyme, or diglyme) at a temperature between 20° and 80° C. for 1-18 hours (Equation 16b). The reaction mixture is then cooled and filtered.

Evaporation of the solvent leaves (4) contaminated with a little $RNH_3+$, $X_5-$ salt. The product may be purified by trituration with ice-water or by dissolution in dichloromethane, followed by washing with a small amount of water, drying, and evaporation of solvent. Further purification may be accomplished by recrystallization or column chromatography on silica gel.

Selenyl heterocycles of Formula (4) where $R_3$ is $CHF_2$ are made by one or more of the variations of the method depicted in Equation 17.

Equation 17

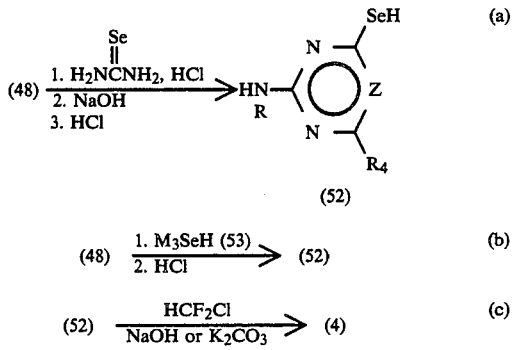

where

R, $R_4$, and $X_5$ are as previously defined;

$R_3$ is $CF_2H$; and $M_3$ is Li, Na, or K.

In Equation (17a) the heterocycle (48) is added to a solution of at least one equivalent of selenourea in aqueous hydrochloric acid. After stirring 1 day at 20°-30° C., the reaction solution is made strongly basic (pH greater than 12) with excess aqueous sodium hydroxide or potassium hydroxide solution. The reaction solution is filtered and then acidified to pH 4 with aqueous hydrochloric or sulfuric acid. If the selenyl heterocycle (52) precipitates, it is filtered out, washed with ice-water, and dried. If it does not precipitate, it is isolated by saturation of the aqueous medium with sodium chloride, thorough extraction with ethyl acetate, and evaporation of the solvent.

The method described in Equation (17a) is more generally useful when Z is CH than when Z is N. When Z is N better results are generally achieved using the method described in Equation (17b). The latter method is also frequently useful when Z is CH. In this method heterocycle (48) and at least two equivalents of $M_3SeH$ (53) in a suitable polar solvent (e.g. methanol, ethanol, N,N-dimethylformamide) are heated at 60°-70° for 30 minutes to 3 hours. The reaction mixture is then cooled, and the solvent is evaporated. The residue is dissolved in aqueous sodium carbonate solution (approximately 2 mL per mmol of (48)). The mixture is filtered, and the filtrate is acidified to pH 4 with aqueous acid (e.g. acetic, hydrochloric, sulfuric acids). If the selenyl heterocycle (52) precipitates it is filtered out, washed with ice-water, and dried. If it does not precipitate, it is isolated by saturation of the aqueous medium with sodium chloride, thorough extraction with ethyl acetate and evaporation of the solvent. Preparation of the reagent $M_3SeH$ (53) has been reviewed by W. H. H. Gunther (op. cit.).

In Equation (17c), when Z is CH, gaseous difluorochloromethane is bubbled through a mixture of selenol (52), dioxane, and concentrated aqueous sodium hydroxide or potassium hydroxide solution at 50° to 80° C. for 1 to 2 hours. The mixture is then cooled, diluted with water, and extracted with ethyl acetate. Evaporation of solvent leaves the selenyl heterocycle (4, $R_3 = CF_2H$). When Z is N, gaseous difluorochloromethane is bubbled through a mixture of selenyl heterocycle (52) and at least one (typically 2-5) equivalent of potassium carbonate in N,N-dimethylformamide at 70°-80° C. for 1-2 hours. The mixture is then cooled, and the solvent is evaporated. The residue is triturated with water. If the the selenyl heterocycle precipitates, it is filtered out, washed with ice-water, and dried. If it does not precipitate, it is isolated by saturation of the aqueous medium with sodium chloride, thorough extraction with ethyl acetate, and evaporation of the solvent.

Selenyl heterocyclic intermediates of Formula (8) are made from the corresponding free heterocycles (4, R=H) by the following method.

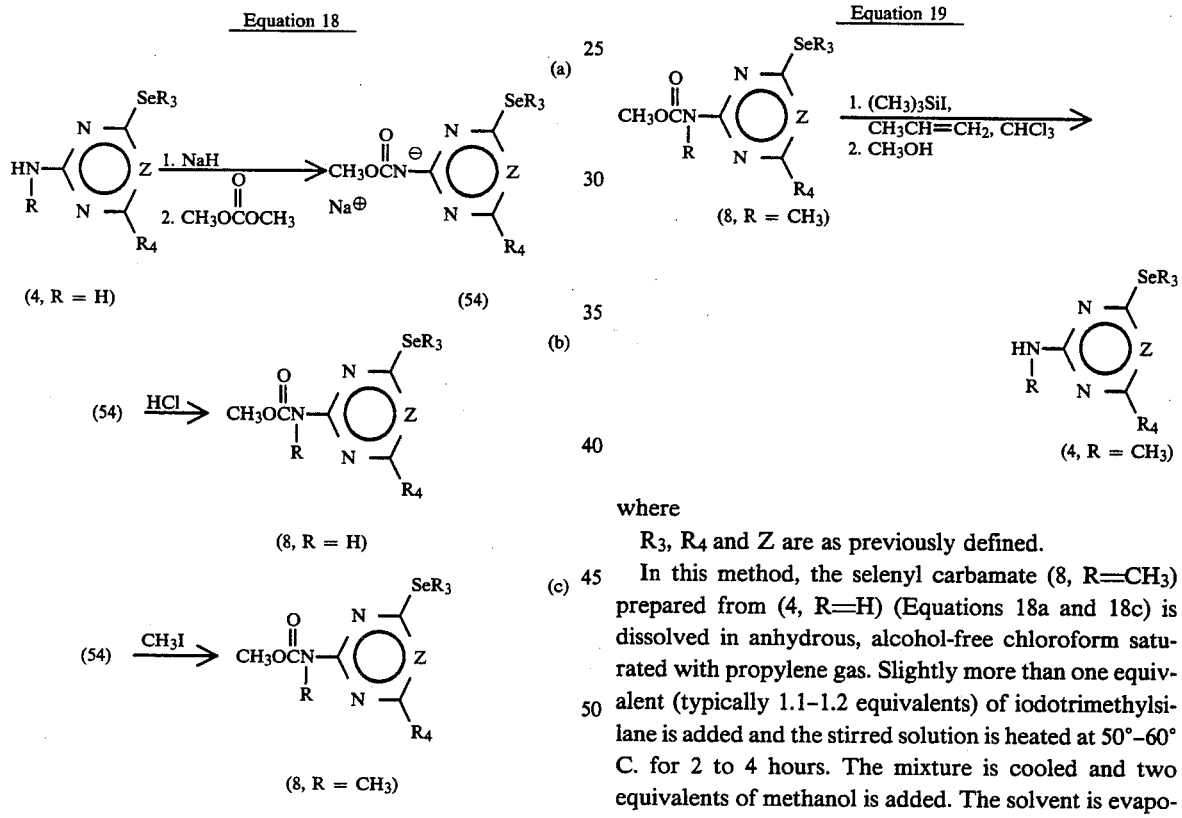

where $R_3$, $R_4$ and Z are as previously defined.

In this method, a solution or slurry of the appropriate selenyl heterocycle (4) in a suitable aprotic solvent (e.g., tetrahydrofuran, dioxane, glyme) at 0°-30° C. is treated with two equivalents of sodium hydride. After gas evolution ceases, the reaction mixture is treated with one equivalent of dimethyl carbonate and stirred at 20°-30° C. for 8 to 24 hours to provide a suspension of the sodium salt (54) (Equation 18a).

Sufficient concentrated hydrochloric acid is then added to bring the pH to 4. The mixture is saturated with sodium chloride and filtered. The organic layer is separated away from the aqueous layer, dried over magnesium sulfate, and filtered. Evaporation of the solvent leaves the selenyl carbamate (8, R=H) (Equation 18b).

Alternatively, the reaction mixture containing (54) formed in Equation 18a is treated with at least two equivalents of iodomethane and then heated at 60°-80° C. for 8 to 24 hours. The mixture is cooled and filtered, and the solvent is evaporated. The residue is taken up in dichloromethane, washed with water, and the solvent is evaporated, leaving the selenyl N-methyl carbamate (8, R=CH$_3$) (Equation 18c).

In some cases selenyl heterocycles of Formula (4) may be more easily prepared with R being H than with R being CH$_3$. Many selenyl heterocycles (4, R=CH$_3$) can be prepared from the corresponding selenyl heterocycles (8, R=CH$_3$) by one or more of the following two methods.

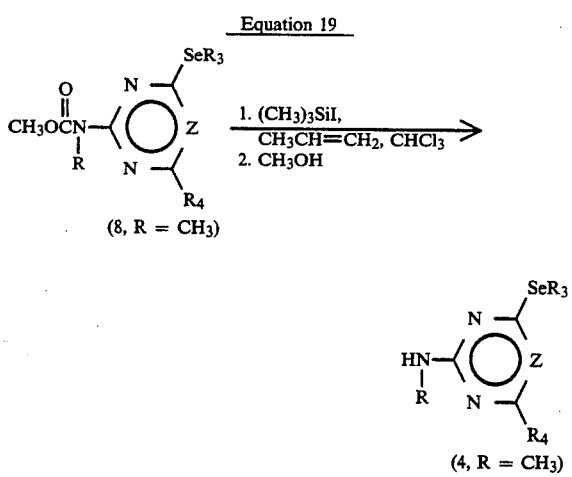

where $R_3$, $R_4$ and Z are as previously defined.

In this method, the selenyl carbamate (8, R=CH$_3$) prepared from (4, R=H) (Equations 18a and 18c) is dissolved in anhydrous, alcohol-free chloroform saturated with propylene gas. Slightly more than one equivalent (typically 1.1-1.2 equivalents) of iodotrimethylsilane is added and the stirred solution is heated at 50°-60° C. for 2 to 4 hours. The mixture is cooled and two equivalents of methanol is added. The solvent is evaporated and the residue is taken up in methanol. The mixture is carefully neutralized with 10% sodium methoxide in methanol, and then the solvent is evaporated. The residue is triturated with ice-water. If a precipitate forms, it is filtered out, rinsed with ice-water and dried to provide (4, R=CH$_3$). If no precipitate forms, the solution is saturated with sodium chloride and extracted with ethyl acetate. Evaporation of the solvent leaves the selenyl heterocycle (4, R=CH$_3$).

Many of the selenyl heterocycles (4, R=CH$_3$) can be prepared from the corresponding selenyl heterocycles (4, R=H) by the method described below.

Equation 20

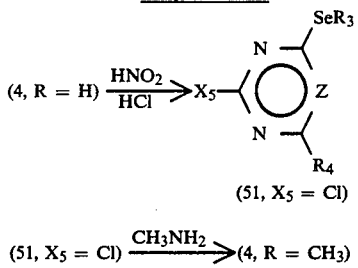

where
R₃, R₄ and Z are as previously defined.

A solution of the amine (4, R=H) in concentrated hydrochloric acid is treated with sodium nitrite solution and the chloro compound (51, X₅=Cl) is isolated in the usual manner by filtration of the acidic solution. A representative procedure is described by Bee and Rose in *J. Chem. Soc. C.*, 2031 (1966), for the case in which Z=CH, and X=Y=OCH₃. The displacement of the chlorine in (51, X₅=Cl) with methylamine is accomplished as already described for Equation 16b.

The heterocyclic amines of Formula (2a) to (2f) below are either known, disclosed in this application, or can be prepared by obvious methods by one skilled in the art.

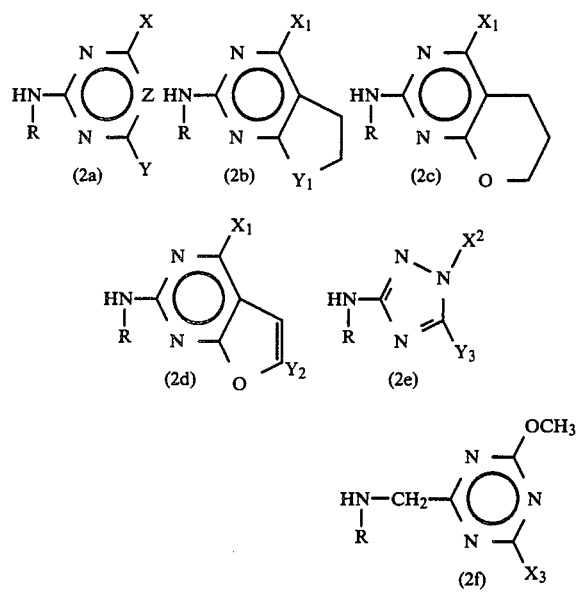

For a review of the synthesis and reactions of 2-amino- and 2-methylaminopyrimidines (2a, Z=CH) see *The Chemistry of Heterocyclic Compounds*, Vol. 16, Wiley-Interscience, New York (1962). For a review of the synthesis and reactions 2-amino- and 2-methylamino-s-triazines (2a, Z=N) see *The Chemistry of Heterocyclic Compounds*, Vol. 13, Wiley-Interscience, New York (1959), F. C. Schaefer, U.S. Pat. No. 3,154,537 and F. C. Schaefer and K. R. Huffman *J. Org. Chem.*, 28, 1812 (1963). The synthesis of the bicyclic amines (2b) and (2c) is taught in European Patent Application No. 80300505.7. The synthesis of bicyclic amines (2d) is taught in European Patent Publication No. 46,677.

The amines of Formula (2) where X or X₁ is OCF₂H and/or Y is OCF₂H or SCF₂H can be prepared by methods taught in South African Patent Application No. 825,045, or by suitable modifications that would be obvious to one skilled in the art.

The pyrimidines of Formula (2a) (Z=CH) where Y is CR'(QCH₃)₂, CR'(QCH₂CH₃)₂,

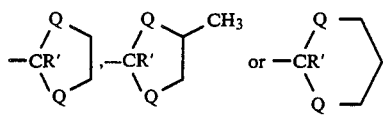

can be prepared according to the methods taught in European Patent Application No. 82306492.8 or suitable modifications thereof known to one skilled in the art.

The triazoles of Formula (2e) can be prepared according to the methods taught in European Patent Application No. 82303611.6 (Publication No. 73,562). The triazine amines of Formula (2f) can be prepared according to the teachings of U.S. Ser. No. 472,879, filed Mar. 14, 1983.

The carbamate intermediates (6) are prepared by the following method.

Equation 21

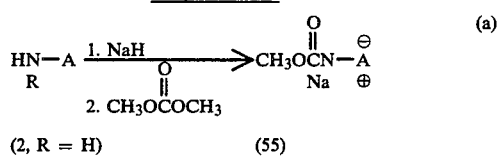

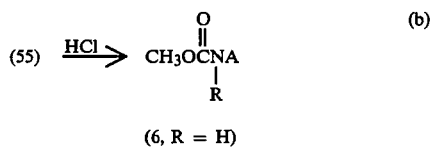

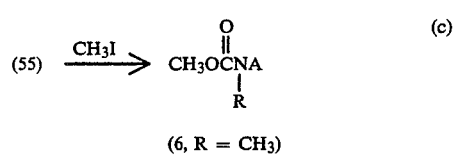

where
A is as previously defined.

The conversion of (2, R=H) to (55) (Equation 21a) is accomplished by the method already described for the conversion of (4, R=H) to (54) (Equation 18a). The conversion of (55) to (6, R=H) (Equation 21b) is accomplished by the method already described for the conversion of (54) to (8, R=H) (Equation 18b). The conversion of (55) to (6, R=CH₃) (Equation 21c) is accomplished by the method already described for the conversion of (54) to (8, R=CH₃) (Equation 18c).

Many of the methylamino heterocyclic intermediates of Formula (2, R=CH₃) may be prepared by one or more of the following two methods from the corresponding amino heterocyclic intermediates of Formula (2, R=H).

Equation 22

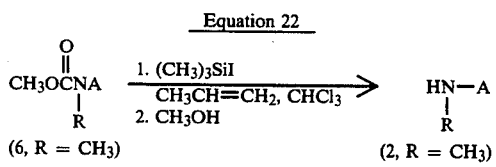

(6, R = CH₃)  (2, R = CH₃)

where

A is as previously defined.

The conversion of (6, R=CH₃) to (2, R=CH₃) is accomplished by the method already described for the conversion of (8, R=CH₃) to (4, R=CH₃) (Equation 19).

Alternatively, the following two-step procedure is useful in many cases.

Equation 23

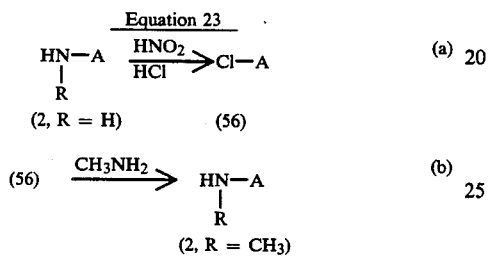

where

A is has been previously defined except that structures relating to (2f) are excluded.

The conversion of (2, R=H) to (2, R=CH₃) is accomplished by the methods already described for the conversion of (4, R=H) to (4, R=CH₃) (Equation 20).

The sulfonyl isocyanates (3) are prepared in most cases from the corresponding sulfonamides (7) by one or more of the following two general methods.

Equation 24

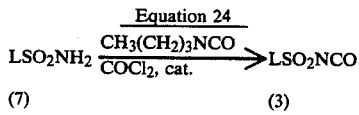

where

L is as previously defined.

The conversion of sulfonamide (7) to sulfonyl isocyanate (3) in Equation 24 is accomplished by the method already described for the conversion of sulfonamide (5) to sulfonyl isocyanate (1) in Equation 13.

Equation 25

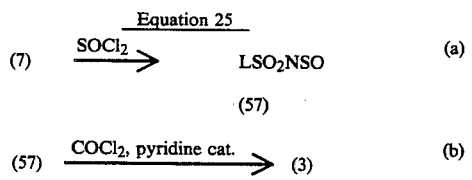

where

L is as previously defined.

The conversion of sulfonamide (7) to sulfonyl isocyanate (3) in Equation 25 is accomplished by the method already described for the conversion of sulfonamide (5) to sulfonyl isocyanate (1) in Equation 14.

The preparation of sulfonamides from ammonia and sulfonyl chlorides is widely reported in the literature, e.g. Crossley et al., *J. Am. Chem. Soc.*, 60, 2223 (1938).

Rarely sulfonamides (5) and (7) may not be of sufficient stability to be useful as starting materials in Equations 13, 14, 24 and 25. In these cases, as well as others, the sulfonyl isocyanates (1) and (3) can be made as an unisolated intermediates by treating the corresponding sulfonyl chlorides (58) and (59) with isocyanate anion in the presence of the heterocyclic amines (2) and (4) respectively. The amines react with the sulfonyl isocyanates as they are formed to give the desired corresponding compounds of Formulae I and II (Equation 26).

Equation 26

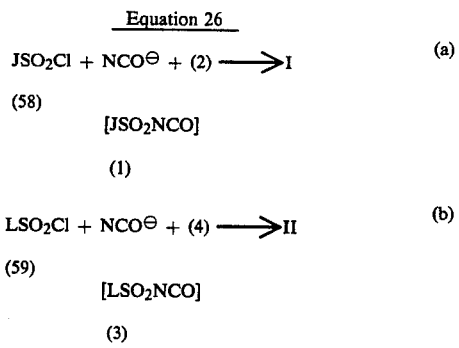

where

J, L, (2), and (4) are as previously defined.

The reaction is best carried out by adding over one to six hours a solution of at least one equivalent of a tetraalkylammonium isocyanate, such as tetra-n-butylammonium isocyanate, in a suitable aprotic organic solvent, such as dichloromethane or tetrahydrofuran, to a well-stirred mixture of one equivalent of sulfonyl chloride (58) or (59) and at least one equivalent of heterocyclic amine (3) or (4) respectively, in a similar suitable organic solvent at 20°–40° C. The reaction mixture is then diluted with dichloromethane, washed with 1N sulfuric acid, and dried over sodium sulfate. Rotary evaporation of the solvent leaves the corresponding product of Formula I or II in crude form. This may be purified as has already been described for Equation 1.

Certain sulfonyl chlorides are best prepared by chlorosulfonation of a substituted benzene, naphthalene, or thiophene in tetrachloromethane according to the teachings of H. T. Clarke et al., *Org. Synth. Coll.*, Vol. 1, 2nd Ed. 1941, p. 85. Other sulfonyl chlorides can be made by diazotization of the appropriate amine with sodium nitrite in hydrochloric acid, followed by reaction of the diazonium salt with sulfur dioxide and cuprous or cupric chloride in acetic acid according to the teachings of H. L. Yale and F. Sowinski, *J. Org. Chem.*, 25, 1824 (1960) and of H. Meerwein et al., *Chem. Ber.*, 90, 841 (1957).

Reference to the following patents is suggested for further details regarding the preparation of the sulfonamides (7) and sulfonyl isocyanates (3): U.S. Pat. No. 4,169,719; U.S. Pat. No. 4,127,405; and U.S. Pat. No. 4,394,506.

The following examples further illustrate the synthesis of this invention.

EXAMPLE 1

N-(1,1-dimethylethyl)-2-(methylselenyl)benzenesulfonamide

Under nitrogen a stirred solution of N-(1,1-dimethylethyl)benzenesulfonamide (25.5 g, 0.120 mmol) in anhydrous tetrahydrofuran (350 mL) was cooled to −45° C. A hexane solution of n-butyllithium (1.44M, 184 mL, 0.264 mmol) was added to give a yellow orange solution. The solution was warmed to room temperature. A thick suspension gradually developed.

After stirring two hours at room temperature, the mixture was cooled to 0° C., and dimethyl diselenide (25.0 g, 0.133 mmol) was added slowly. Gradually the solid dissolved. The reaction solution was stirred at room temperature overnight, and then was treated with aqueous ammonium sulfate (33 g/100 mL $H_2O$). The organic layer was dried ($Na_2SO_4$) and rotary evaporated to give a yellow oil. This was dissolved in toluene and rotary evaporated. The process was repeated to give 40.2 g of yellow solid. This was recrystallized from hot n-heptane (5 mL/g) plus enough benzene (approx. 2 mL/g) to prevent oiling out. After cooling in an ice bath, the N-(1,1-dimethylethyl)-2-(methylselenyl)benzenesulfonamide was collected, washed with hexanes and dried. The yield was 34.6 g of product melting at 113°–117° C. PMR(CDCl$_3$, 200 MHz): δ 8.04 (dd, 1H, Ar-H); 7.52 (dd, 1H, Ar-H); 7.43 (td, 1H, Ar-H); 7.31 (td, 1H, Ar-H); 5.45 (br s, 1H, NH); 2.40 (s, w/satellites, 3H, SeCH$_3$); 1.18 (s, 9H, t-Bu). IR(Nujol): 3270 (m, NH) cm$^{-1}$.

EXAMPLE 2

2-(Methylselenyl)benzenesulfonamide

Under nitrogen a solution of N-(1,1-dimethylethyl)-2-(methylselenyl)benzenesulfonamide (34.5 g, 0.113 mmol) in trifluoroacetic acid (100 mL) was stirred at room temperature overnight. The solvent was then rotary evaporated to leave an amber solid. This was again treated with trifluoroacetic acid (100 mL) at room temperature overnight. The mixture was concentrated in vacuo, then poured into ice-water. The solid was collected, rinsed with ice-water, and dried in vacuo. The crude product was recrystallized from hot benzene (5 mL/g), collected at room temperature, rinsed with benzene and hexanes, and dried. The 2-(methylselenyl)-benzenesulfonamide (23.1 g) obtained melted at 119°–121° C.

PMR(CDCl$_3$, 80 MHz): δ 8.01 (dd, 1H, Ar-H); 7.15–7.60 (m, 3H, Ar-H); 5.30 (br s, 2H, NH$_2$); 2.41 (s, w/satellites, SeCH$_3$). IR(Nujol): 3355 (m, NH$_2$); 3255 (m, NH$_2$) cm$^{-1}$.

EXAMPLE 3

2-(Methylselenyl)benzenesulfonyl isocyanate

A solution of 2-(methylselenyl)benzenesulfonamide (6.25 g, 25.0 mmol), n-butyl isocyanate (2.81 mL, 25.0 mmol), and 1,4-diaza[2.2.2]bicyclooctane (0.1 g, 1 mmol) in mixed xylenes was heated at reflux for 0.5 hours. Phosgene was then added at such a rate that the internal temperature stayed at 133° C. or above. When consumption of phosgene ceased, the solution was cooled to room temperature and then filtered under nitrogen. Rotary evaporation gave 2-(methylselenyl)-benzenesulfonyl isocyanate as a brown oil (8.8 g). This was used immediately without further purification or characterization.

EXAMPLE 4

N-[(4,6-Dimethylpyrimidin-2-yl)aminocarbonyl]-2-(methylselenyl)benzenesulfonamide To a slurry of 4,6-dimethyl-2-pyrimidinamine (0.36 g, 29 mmol) in dry dichloromethane (5 mL) was added a solution of 2-(methylselenyl)benzenesulfonyl isocyanate (1.5 g, crude, 4.2 mmol) in dichloromethane (5 mL). The heterocycle dissolved. The solution was heated at reflux for two hours and stirred at room temperature overnight. The solution was filtered and rotary evaporated to give 1.7 g of yellow solid. This was dissolved in dichloromethane and chromatographed on a column of silica gel using as eluant 320 mL of 15:1, 220 mL of 10:1, 230 mL of 7.5:1, and finally 240 mL of 5:1 dichloromethane-ether, all with 2 mL/L acetic acid. The appropriate fractions were diluted with toluene and rotary evaporated. The residue was dissolved in dichloromethane, diluted with 1-chlorobutane, and rotary evaporated to give a white crystalline solid. This was slurried in hexanes, collected, rinsed with 1-chlorobutane, 1:1 1-chlorobutanehexanes, and hexanes and air dried. The product was isolated as 1.03 g of small white crystalline plates, melting at 205°–207° C. with decomposition.

PMR(CDCl$_3$, 80 MHz); δ 13.26 (br s, 1H, SO$_2$NHCO); 8.27 (sl br d, 1H, Ar-H); 7.56 (br s, 1H, CONH-Het); 7.30–7.55 (m, 3H, Ar-H); 6.76 (s, 1H, Het 5-H); 2.47 (s, 6H, Het-CH$_3$); 2.30 (s, w/sattellites, 3H, SeCH$_3$). IR(Nujol): 1689 (s, C=O) cm$^{-1}$.

EXAMPLE 5

4-Methoxy-6-(methylselenyl)-2-pyrimidinamine

A solution of dimethyl diselenide (5.0 g, 26.6 mmol) in anhydrous tetrahydrofuran (46 mL) under nitrogen was cooled in an ice-bath. To this stirred solution was added dropwise a hexane solution of n-butyllithium (1.44M, 17.7 mL, 25.5 mmol). The orange color of the diselenide faded away. 4-Chloro-6-methoxy-2-pyrimidinamine (3.7 g, 23.2 mmol) was added in one portion. The mixture was heated at reflux for two hours, then cooled, filtered, and rotary evaporated to give a solid (5.8 g).

This was dissolved in dichloromethane containing tetrahydrofuran and absorbed on silica gel (3 g/g). This was loaded on a column of same mesh silica gel and eluted with 3300 mL of 10:1 followed by 1200 mL of 5:1 dichloromethane-ether. Fractions containing product (R$_f$=0.34, 10:1 CH$_2$Cl$_2$-Et$_2$O, UV) were rotary evaporated to give an oil. This was dissolved in dichloromethane, diluted with hexanes, and rotary evaporated to give a crystalline solid. This was slurried in hexanes, collected, washed with hexanes and dried. 4-Methoxy-6-(methylselenyl)-2-pyrimidinamine was obtained as a white crystalline powder (3.6 g) melting at 98°–100° C.

PMR(CDCl$_3$, 90 MHz): δ 6.15 (s, 1H, 5-H); 5.09 (br s, 2H, NH$_2$); 3.88 (s, 3H, OCH$_3$); 2.37 (s, w/satellites, 3H, SeCH$_3$). IR(Nujol): 3330 (m, NH$_2$); 3220 (m, NH$_2$) cm$^{-1}$.

EXAMPLE 6

Methyl 2-[[[4-methoxy-6-(methylselenyl)pyrimidin-2-yl]-aminocarbonyl]aminosulfonyl]benzoate To a mixture of 4-methoxy-6-methylselenyl-2-pyrimidinamine (0.63 g, 2.9 mmol) and 2-carbomethoxybenzenesulfonyl isocyanate (1.00 g, 4.1 mmol) under nitrogen atmosphere was added dry dichloromethane (10 mL). The stirred mixture was warmed, and the solid dissolved. The solution was stirred at room temperature overnight and then filtered and rotary evaporated to give a solid (1.6 g).

The crude product was dissolved in dichloromethane and chromatographed on a column of silica gel using as eluant 525 mL of 20:1, 267 mL of 15:1, and finally 275 mL of 10:1 dichloromethane-ether, all with 2 mL/L acetic acid. The appropriate fractions were diluted with toluene and rotary evaporated. The residue was dissolved in dichloromethane, diluted with 1-chlorobutane, and rotary evaporated to give a crystalline solid. This was slurried in hexanes, collected, washed with 1:1 1-chlorobutane-hexanes and hexanes, and dried. The product was obtained as a white crystalline powder (1.2 g) melting at 165°–168° C.

PMR(CDCl$_3$, 80 MHz): δ 12.49 (br s, 1H, SO$_2$NHCO); 8.30–8.55 (m, 1H, Ar-H); 7.55–7.80 (m, 3H, Ar-H); 7.32 (br s, 1H, CONH-Het); 6.47 (s, 1H, Het 5-H); 3.99 (s, 3H, Het-OCH$_3$); 3.92 (s, 3H, CO$_2$CH$_3$); 2.49 (s, w/satellites, 3H, SeCH$_3$).

Also evident in the PMR spectrum is 3.5 wt. % 1-chlorobutane.

IR(Nujol): 1734 (s, ester C=O); 1719 (s, urea C=O) cm$^{-1}$.

Using the procedures and examples shown above, the compounds in Tables 1–16 can be prepared.

TABLE 1

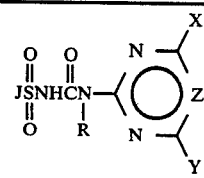

| J | R | R$_1$ | R$_2$ | X | Y | Z | m.p. (°C.) |
|---|---|---|---|---|---|---|---|
| J-1 | H | CH$_3$ | H | CH$_3$ | CH$_3$ | CH | 205–207 |
| J-1 | H | CH$_3$ | H | CH$_3$ | OCH$_3$ | CH | 207–210 (d) |
| J-1 | H | CH$_3$ | H | OCH$_3$ | OCH$_3$ | CH | 199–204 (d) |
| J-1 | H | CH$_3$ | H | CH$_3$ | CH$_3$ | N | 186–189 (d) |
| J-1 | H | CH$_3$ | H | CH$_3$ | OCH$_3$ | N | 178–184 (d) |
| J-1 | H | CH$_3$ | H | OCH$_3$ | OCH$_3$ | N | 177–181 |
| J-1 | CH$_3$ | CH$_3$ | H | CH$_3$ | OCH$_3$ | CH | |
| J-1 | CH$_3$ | CH$_3$ | H | OCH$_3$ | OCH$_3$ | CH | |
| J-1 | CH$_3$ | CH$_3$ | H | CH$_3$ | OCH$_3$ | N | |
| J-1 | CH$_3$ | CH$_3$ | H | OCH$_3$ | OCH$_3$ | N | |
| J-1 | H | CH$_2$CH$_3$ | H | CH$_3$ | CH$_3$ | CH | 193–194 (d) |
| J-1 | H | CH$_2$CH$_3$ | H | CH$_3$ | OCH$_3$ | CH | 191–194 (d) |
| J-1 | H | CH$_2$CH$_3$ | H | OCH$_3$ | OCH$_3$ | CH | 190–192 |
| J-1 | H | CH$_2$CH$_3$ | H | CH$_3$ | CH$_3$ | N | 175–177 |
| J-1 | H | CH$_2$CH$_3$ | H | CH$_3$ | OCH$_3$ | N | 163–164 |
| J-1 | H | CH$_2$CH$_3$ | H | OCH$_3$ | OCH$_3$ | N | 173–175 |
| J-1 | CH$_3$ | CH$_2$CH$_3$ | H | CH$_3$ | OCH$_3$ | CH | |
| J-1 | CH$_3$ | CH$_2$CH$_3$ | H | OCH$_3$ | OCH$_3$ | CH | |
| J-1 | CH$_3$ | CH$_2$CH$_3$ | H | CH$_3$ | OCH$_3$ | N | |
| J-1 | CH$_3$ | CH$_2$CH$_3$ | H | OCH$_3$ | OCH$_3$ | N | |
| J-1 | H | (CH$_2$)$_2$CH$_3$ | H | CH$_3$ | CH$_3$ | CH | |
| J-1 | H | (CH$_2$)$_2$CH$_3$ | H | CH$_3$ | OCH$_3$ | CH | |
| J-1 | H | (CH$_2$)$_2$CH$_3$ | H | OCH$_3$ | OCH$_3$ | CH | |
| J-1 | H | (CH$_2$)$_2$CH$_3$ | H | CH$_3$ | CH$_3$ | N | |
| J-1 | H | (CH$_2$)$_2$CH$_3$ | H | CH$_3$ | OCH$_3$ | N | |
| J-1 | H | (CH$_2$)$_2$CH$_3$ | H | OCH$_3$ | OCH$_3$ | N | |
| J-1 | CH$_3$ | (CH$_2$)$_2$CH$_3$ | H | CH$_3$ | OCH$_3$ | CH | |
| J-1 | CH$_3$ | (CH$_2$)$_2$CH$_3$ | H | OCH$_3$ | OCH$_3$ | CH | |
| J-1 | CH$_3$ | (CH$_2$)$_2$CH$_3$ | H | CH$_3$ | OCH$_3$ | N | |
| J-1 | CH$_3$ | (CH$_2$)$_2$CH$_3$ | H | OCH$_3$ | OCH$_3$ | N | |
| J-1 | H | CH$_2$CH=CH$_2$ | H | CH$_3$ | CH$_3$ | CH | |
| J-1 | H | CH$_2$CH=CH$_2$ | H | CH$_3$ | OCH$_3$ | CH | |
| J-1 | H | CH$_2$CH=CH$_2$ | H | OCH$_3$ | OCH$_3$ | CH | |
| J-1 | H | CH$_2$CH=CH$_2$ | H | CH$_3$ | CH$_3$ | N | |
| J-1 | H | CH$_2$CH=CH$_2$ | H | CH$_3$ | OCH$_3$ | N | |
| J-1 | H | CH$_2$CH=CH$_2$ | H | OCH$_3$ | OCH$_3$ | N | |
| J-1 | CH$_3$ | CH$_2$CH=CH$_2$ | H | CH$_3$ | OCH$_3$ | CH | |
| J-1 | CH$_3$ | CH$_2$CH=CH$_2$ | H | OCH$_3$ | OCH$_3$ | CH | |
| J-1 | CH$_3$ | CH$_2$CH=CH$_2$ | H | CH$_3$ | OCH$_3$ | N | |
| J-1 | CH$_3$ | CH$_2$CH=CH$_2$ | H | OCH$_3$ | OCH$_3$ | N | |
| J-1 | H | CH$_2$C≡CH | H | CH$_3$ | CH$_3$ | CH | |
| J-1 | H | CH$_2$C≡CH | H | CH$_3$ | OCH$_3$ | CH | |
| J-1 | H | CH$_2$C≡CH | H | OCH$_3$ | OCH$_3$ | CH | |
| J-1 | H | CH$_2$C≡CH | H | CH$_3$ | CH$_3$ | N | |
| J-1 | H | CH$_2$C≡CH | H | CH$_3$ | OCH$_3$ | N | |
| J-1 | H | CH$_2$C≡CH | H | OCH$_3$ | OCH$_3$ | N | |
| J-1 | CH$_3$ | CH$_2$C≡CH | H | CH$_3$ | OCH$_3$ | CH | |
| J-1 | CH$_3$ | CH$_2$C≡CH | H | OCH$_3$ | OCH$_3$ | CH | |
| J-1 | CH$_3$ | CH$_2$C≡CH | H | CH$_3$ | OCH$_3$ | N | |
| J-1 | CH$_3$ | CH$_2$C≡CH | H | OCH$_3$ | OCH$_3$ | N | |
| J-1 | H | CH(CH$_3$)$_2$ | H | CH$_3$ | CH$_3$ | CH | |
| J-1 | H | CH(CH$_3$)$_2$ | H | CH$_3$ | OCH$_3$ | CH | |
| J-1 | H | CH(CH$_3$)$_2$ | H | OCH$_3$ | OCH$_3$ | CH | |
| J-1 | H | CH(CH$_3$)$_2$ | H | CH$_3$ | CH$_3$ | N | |
| J-1 | H | CH(CH$_3$)$_2$ | H | CH$_3$ | OCH$_3$ | N | |
| J-1 | H | CH(CH$_3$)$_2$ | H | OCH$_3$ | OCH$_3$ | N | |
| J-1 | CH$_3$ | CH(CH$_3$)$_2$ | H | CH$_3$ | OCH$_3$ | CH | |
| J-1 | CH$_3$ | CH(CH$_3$)$_2$ | H | OCH$_3$ | OCH$_3$ | CH | |

TABLE 1-continued

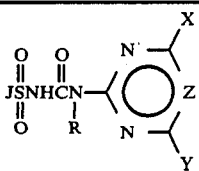

| J | R | R₁ | R₂ | X | Y | Z | m.p. (°C.) |
|---|---|---|---|---|---|---|---|
| J-1 | CH₃ | CH(CH₃)₂ | H | CH₃ | OCH₃ | N | |
| J-1 | CH₃ | CH(CH₃)₂ | H | OCH₃ | OCH₃ | N | |
| J-1 | H | C(CH₃)₃ | H | CH₃ | CH₃ | CH | |
| J-1 | H | C(CH₃)₃ | H | CH₃ | OCH₃ | CH | |
| J-1 | H | C(CH₃)₃ | H | OCH₃ | OCH₃ | CH | |
| J-1 | H | C(CH₃)₃ | H | CH₃ | CH₃ | N | |
| J-1 | H | C(CH₃)₃ | H | CH₃ | OCH₃ | N | |
| J-1 | H | C(CH₃)₃ | H | OCH₃ | OCH₃ | N | |
| J-1 | CH₃ | C(CH₃)₃ | H | CH₃ | OCH₃ | CH | |
| J-1 | CH₃ | C(CH₃)₃ | H | OCH₃ | OCH₃ | CH | |
| J-1 | CH₃ | C(CH₃)₃ | H | CH₃ | OCH₃ | N | |
| J-1 | CH₃ | C(CH₃)₃ | H | OCH₃ | OCH₃ | N | |
| J-1 | H | CF₂H | H | CH₃ | CH₃ | CH | |
| J-1 | H | CF₂H | H | CH₃ | OCH₃ | CH | |
| J-1 | H | CF₂H | H | OCH₃ | OCH₃ | CH | |
| J-1 | H | CF₂H | H | CH₃ | CH₃ | N | |
| J-1 | H | CF₂H | H | CH₃ | OCH₃ | N | |
| J-1 | H | CF₂H | H | OCH₃ | OCH₃ | N | |
| J-1 | CH₃ | CF₂H | H | CH₃ | OCH₃ | CH | |
| J-1 | CH₃ | CF₂H | H | OCH₃ | OCH₃ | CH | |
| J-1 | CH₃ | CF₂H | H | CH₃ | OCH₃ | N | |
| J-1 | CH₃ | CF₂H | H | OCH₃ | OCH₃ | N | |
| J-1 | H | CH₂CH(CH₃)₂ | H | OCH₃ | OCH₃ | CH | |
| J-1 | H | CH(CH₃)₂ | H | Cl | OCH₃ | CH | |
| J-1 | H | (CH₂)₃CH₃ | H | CH₃ | CH₃ | N | |
| J-1 | H | CH(CH₃)(CH₂CH₃) | H | CH₃ | OCH₃ | N | |
| J-1 | H | C(CH₃)₃ | H | Cl | OCH₃ | CH | |
| J-1 | H | CH₂CH=CH₂ | H | Cl | OCH₃ | CH | |
| J-1 | H | CH₂C(CH₃)=CH₂ | H | CH | OCH₃ | CH₃ | |
| J-1 | H | CH₂CH=CHCH₃ | H | OCH₃ | OCH₃ | N | |
| J-1 | H | CH₂C≡CH | H | Cl | OCH₃ | CH | |
| J-1 | H | CH₂C≡CCH₃ | H | OCH₃ | OCH₃ | N | |
| J-1 | H | CF₂H | H | Cl | OCH₃ | CH | |
| J-1 | H | CH₂CH₂OCH₃ | H | OCH₃ | OCH₃ | N | |
| J-1 | H | CH(CH₃)CH=CH₂ | H | CH₃ | OCH₃ | CH | |
| J-1 | H | CH(CH₃)C≡CH | H | CH₃ | OCH₃ | N | |
| J-1 | H | CH₃ | 3-F | OCH₃ | OCH₃ | CH | |
| J-1 | H | CH₃ | 3-Cl | CH₃ | CH₃ | CH | |
| J-1 | H | CH₃ | 3-CH₃ | CH₃ | CH₃ | N | |
| J-1 | H | CH₃ | 3-OCH₃ | CH₃ | OCH₃ | N | |
| J-1 | H | CH₃ | 5-F | CH₃ | CH₃ | N | |
| J-1 | H | CH₃ | 5-Cl | CH₃ | CH₃ | CH | |
| J-1 | H | CH₃ | 5-Br | OCH₃ | OCH₃ | N | |
| J-1 | H | CH₃ | 5-CH₃ | CH₃ | OCH₃ | N | |
| J-1 | H | CH₃ | 5-CF₃ | CH₃ | OCH₃ | CH | |
| J-1 | H | CH₃ | 5-OCH₃ | CH₃ | CH₃ | N | |
| J-1 | H | CH₃ | 5-SCH₃ | OCH₃ | OCH₃ | CH | |
| J-1 | H | CH₃ | 5-OCF₂H | CH₃ | OCH₃ | N | |
| J-1 | H | CH₃ | 5-SCF₂H | OCH₃ | OCH₃ | CH | |
| J-1 | H | CH₃ | 6-F | CH₃ | OCH₃ | N | |
| J-1 | H | CH₃ | 6-Cl | OCH₃ | OCH₃ | N | |
| J-1 | H | CH₃ | 6-OCH₃ | CH₃ | CH₃ | N | |
| J-1 | H | CH₃ | 6-SCH₃ | CH₃ | OCH₃ | CH | |
| J-1 | H | CH₂CH₃ | 5-Cl | CH₃ | CH₃ | CH | |
| J-1 | H | CH₂CH₃ | 5-OCH₃ | OCH₃ | OCH₃ | N | |
| J-1 | H | CH₂CH₃ | 6-Cl | CH₃ | CH₃ | N | |
| J-1 | H | CH₂CH₃ | 6-OCH₃ | OCH₃ | OCH₃ | CH | |
| J-1 | H | CH₃ | 6-Se(CH₂)₂CH₃ | CH₃ | OCH₃ | CH | |
| J-1 | H | CH₂CH₃ | 6-SeCH₂CH₃ | OCH₃ | OCH₃ | CH | 153–156 |
| J-1 | H | CH₂CH₃ | 6-SeCH₂CH₃ | OCH₃ | OCH₃ | N | 169–170 |
| J-2 | H | CH₃ | — | CH₃ | CH₃ | N | |
| J-2 | H | CH₂CH₃ | — | OCH₃ | OCH₃ | CH | |
| J-2 | H | (CH₂)₂CH₃ | — | CH₃ | CH₃ | CH | |
| J-2 | H | CH(CH₃)₂ | — | OCH₃ | OCH₃ | CH | |
| J-2 | H | C(CH₃)₃ | — | OCH₃ | OCH₃ | N | |
| J-2 | H | CH₂CH=CH₂ | — | CH₃ | CH₃ | N | |
| J-2 | H | CH₂CH=CHCH₃ | — | CH₃ | OCH₃ | N | |
| J-2 | H | CH₂C≡CH | — | CH₃ | CH₃ | CH | |
| J-2 | H | CH₂C≡CCH₃ | — | CH₃ | OCH₃ | N | |
| J-2 | CH₃ | CH₃ | — | OCH₃ | OCH₃ | CH | |
| J-3 | H | CH₃ | — | CH₃ | OCH₃ | N | |

TABLE 1-continued

| J | R | R₁ | R₂ | X | Y | Z | m.p. (°C.) |
|---|---|---|---|---|---|---|---|
| J-3 | H | CH₂CH₃ | — | CH₃ | OCH₃ | N | |
| J-3 | H | (CH₂)₂CH₃ | — | OCH₃ | OCH₃ | CH | |
| J-3 | H | CH(CH₃)₂ | — | CH₃ | OCH₃ | N | |
| J-3 | H | C(CH₃)₃ | — | CH₃ | OCH₃ | CH | |
| J-3 | H | CH₂CH=CH₂ | — | CH₃ | CH₃ | CH | |
| J-3 | H | CH₂CH=$^t$CHCH₃ | — | OCH₃ | OCH₃ | N | |
| J-3 | H | CH₂C≡CH | — | OCH₃ | OCH₃ | N | |
| J-3 | H | CH₂C≡CCH₃ | — | OCH₃ | OCH₃ | CH | |
| J-3 | CH₃ | CH₃ | — | CH₃ | CH₃ | CH | |
| J-4 | H | CH₃ | — | CH₃ | OCH₃ | CH | |
| J-4 | H | CH₂CH₃ | — | OCH₃ | OCH₃ | N | |
| J-4 | H | (CH₂)₂CH₃ | — | CH₃ | OCH₃ | N | |
| J-4 | H | CH(CH₃)₂ | — | CH₃ | CH₃ | N | |
| J-4 | H | C(CH₃)₃ | — | CH₃ | CH₃ | CH | |
| J-4 | H | CH₂CH=CH₂ | — | OCH₃ | OCH₃ | N | |
| J-4 | H | CH₂CH=$^t$CHCH₃ | — | OCH₃ | OCH₃ | CH | |
| J-4 | H | CH₂C≡CH | — | CH₃ | OCH₃ | CH | |
| J-4 | H | CH₂C≡CCH₃ | — | OCH₃ | OCH₃ | CH | |
| J-4 | CH₃ | CH₃ | — | CH₃ | OCH₃ | N | |
| J-5 | H | CH₃ | — | CH₃ | OCH₃ | CH | |
| J-5 | H | CH₂CH₃ | — | OCH₃ | OCH₃ | N | |
| J-5 | H | (CH₂)₂CH₃ | — | CH₃ | CH₃ | CH | |
| J-5 | H | CH(CH₃)₂ | — | CH₃ | OCH₃ | CH | |
| J-5 | H | C(CH₃)₃ | — | OCH₃ | OCH₃ | CH | |
| J-5 | H | CH₂CH=CH₂ | — | OCH₃ | OCH₃ | N | |
| J-5 | H | CH₂CH=$^t$CHCH₃ | — | CH₃ | OCH₃ | CH | |
| J-5 | H | CH₂C≡CH | — | CH₃ | OCH₃ | N | |
| J-5 | H | CH₂C≡CCH₃ | — | OCH₃ | OCH₃ | CH | |
| J-5 | CH₃ | CH₃ | — | CH₃ | OCH₃ | CH | |
| J-2 | H | CF₂H | — | OCH₃ | OCH₃ | N | |
| J-2 | H | CH₂CH₂OCH₃ | — | CH₃ | OCH₃ | N | |
| J-3 | H | CF₂H | — | CH₃ | CH₃ | CH | |
| J-3 | H | CH₂CH₂OCH₃ | — | OCH₃ | OCH₃ | CH | |
| J-4 | H | CF₂H | — | CH₃ | OCH₃ | N | |
| J-4 | H | CH₂CH₂OCH₃ | — | CH₃ | OCH₃ | CH | |
| J-5 | H | CF₂H | — | CH₃ | CH₃ | CH | |
| J-5 | H | CH₂CH₂OCH₃ | — | OCH₃ | OCH₃ | N | |
| J-1 | H | CH₃ | H | CH₃ | OCH₂CH₃ | N | |
| J-1 | H | CH₃ | H | Cl | OCH₃ | CH | 198–200 |
| J-1 | H | CH₃ | H | F | OCH₃ | CH | |
| J-1 | H | CH₃ | H | Br | OCH₃ | CH | 190–192 |
| J-1 | H | CH₃ | H | CH₃ | OCF₂H | CH | |
| J-1 | H | CH₃ | H | CH₂F | CH₃ | CH | |
| J-1 | H | CH₃ | H | CH₃ | CF₃ | CH | 160–162 |
| J-1 | H | CH₃ | H | OCH₃ | H | CH | |
| J-1 | H | CH₃ | H | CH₃ | OCH₂CH₃ | CH | |
| J-1 | H | CH₃ | H | OCH₃ | OCH₂CH₃ | N | |
| J-1 | H | CH₃ | H | OCH₂CH₃ | OCH₂CH₃ | N | |
| J-1 | H | CH₃ | H | OCH₃ | CH₂OCH₃ | N | |
| J-1 | H | CH₃ | H | OCH₃ | SeCH₃ | CH | |
| J-1 | H | CH₃ | H | CH₃ | CH₂OCH₂CH₃ | CH | |
| J-1 | H | CH₃ | H | OCH₃ | NH₂ | N | |
| J-1 | H | CH₃ | H | OCH₃ | NHCH₃ | N | |
| J-1 | H | CH₃ | H | OCH₃ | N(CH₃)₂ | CH | 225–227 (d) |
| J-1 | H | CH₃ | H | CH₃ | CH₂CH₃ | CH | |
| J-1 | H | CH₃ | H | OCH₃ | CF₃ | CH | |
| J-1 | H | CH₃ | H | OCH₃ | SCH₃ | CH | |
| J-1 | H | CH₃ | H | CH₃ | OCH₂CH=CH₂ | N | |
| J-1 | H | CH₃ | H | CH₃ | OCH₂C≡CH | N | |
| J-1 | H | CH₃ | H | OCH₃ | OCH₂CF₃ | CH | |
| J-1 | H | CH₃ | H | CH₃ | OCH₂CH₂OCH₃ | N | |
| J-1 | H | CH₃ | H | OCH₃ | CH₂SCH₃ | CH | |
| J-1 | H | CH₃ | H | OCH₃ | OCF₂H | CH | |
| J-1 | H | CH₃ | H | OCH₃ | SCF₂H | CH | |
| J-1 | H | CH₃ | H | CH₃ | CH(OCH₃)₂ | N | |
| J-1 | H | CH₃ | H | OCH₃ | CCH₃(OCH₃)₂ | CH | |
| J-1 | H | CH₃ | H | OCH₃ | CH(SCH₃)₂ | CH | |
| J-1 | H | CH₃ | H | OCH₃ | CH(SCH₃)₂ | CH | |

TABLE 1-continued
| J | R | R₁ | R₂ | X | Y | Z | m.p. (°C.) |
|---|---|---|---|---|---|---|---|
| J-1 | H | CH₃ | H | OCH₃ |  | N | |
| J-1 | H | CH₃ | H | CH₃ |  | CH | |
| J-1 | H | CH₃ | H | OCH₃ |  | CH | |
| J-1 | H | CH₃ | H | OCH₃ |  | CH | |
| J-1 | H | CH₃ | H | CH₃ |  | N | |
| J-1 | H | CH₃ | H | OCH₃ |  | CH | |
| J-1 | H | CH₃ | H | OCH₃ |  | CH | |
| J-1 | H | CH₃ | H | OCH₃ |  | CH | |
| J-1 | H | CH₃ | H | CH₃ |  | CH | |
| J-1 | H | CH₃ | H | OCH₃ |  | CH | |
| J-1 | H | CH₃ | H | OCH₃ |  | CH | |

TABLE 1-continued

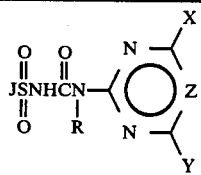

| J | R | R₁ | R₂ | X | Y | Z | m.p. (°C.) |
|---|---|---|---|---|---|---|---|
| J-1 | H | CH₃ | H | OCH₃ | (thiophene ring with CH₃, CCH₃, S) | CH | |
| J-1 | H | CH₃ | H | CH₃ | CH(OCH₂CH₃)₂ | CH | |
| J-1 | H | CH₃ | H | OCH₃ | CCH₃(OCH₂CH₃)₂ | CH | |
| J-1 | H | CH₃ | H | OCH₃ | CH(SCH₂CH₃)₂ | CH | |
| J-1 | H | CH₃ | H | OCH₃ | CCH₃(SCH₂CH₃)₂ | CH | |
| J-1 | H | CH₃ | H | OCH₂CH₃ | OCH₂CH₃ | CH | |
| J-1 | H | CH₃ | H | OCF₂H | OCF₂H | CH | |
| J-1 | H | CH₃ | H | CF₃ | CF₃ | CH | |
| J-1 | H | CH₃ | H | CH₃ | SeCH₃ | CH | |
| J-1 | H | CH₃ | H | OCH₃ | SeCH₃ | N | |
| J-1 | H | CH₃ | H | OCH₂CH₃ | SeCH₃ | N | |
| J-1 | H | CH₃ | H | OCF₂H | SeCH₃ | CH | |
| J-1 | H | CH₃ | H | CF₃ | SeCH₃ | CH | |
| J-1 | H | CH₂CH₃ | H | Cl | OCH₃ | CH | 187–188 |
| J-1 | H | CH₂CH₃ | H | Br | OCH₃ | CH | |
| J-1 | H | CH₂CH₃ | H | CH₃ | CF₃ | CH | |
| J-1 | H | CH₃ | H | CH₃ | CH(OCH₃)₂ | CH | |
| J-1 | H | CH₂CH₃ | H | CH₃ | CH(OCH₃)₂ | CH | |
| J-1 | H | CH₃ | H | OCH₃ | CH(OCH₃)₂ | CH | 158–160 |
| J-1 | H | CH₂CH₃ | H | OCH₃ | CH(OCH₃)₂ | CH | |
| J-1 | H | CH₃ | H | CH₃ | OCH₂CF₃ | N | |
| J-1 | H | CH₂CH₃ | H | CH₃ | OCH₂CF₃ | N | |
| J-1 | H | CH₂CH₃ | H | OCH₃ | N(CH₃)₂ | CH | |
| J-1 | H | CH₃ | H | OCH₃ | N(CH₃)₂ | N | 195–196 |
| J-1 | H | CH₂CH₃ | H | OCH₃ | N(CH₃)₂ | N | |
| J-1 | H | CH₂CH₃ | H | CH₃ | OCH₂CH₃ | CH | |
| J-1 | H | CH₃ | H | OCH₃ | OCH₂CF₃ | N | 188–189 |
| J-1 | H | CH₂CH₃ | H | OCH₃ | OCH₂CF₃ | N | |
| J-1 | H | CH₂CH₃ | H | CH₃ | OCH₂CH₃ | N | |
| J-1 | H | CH₃ | H | OCF₂H | OCF₂H | CH | |
| J-1 | H | CH₃ | H | CF₃ | CF₃ | CH | |
| J-1 | H | (CH₂)₂CH₃ | H | Cl | OCH₃ | CH | |
| J-1 | H | CH₃ | H | OCH₃ | N(CH₃)₂ | CH | |
| J-1 | H | CH₃ | H | CH₃ | CH₂OCH₃ | CH | 187–188 (d) |

TABLE 2 / TABLE 2-continued

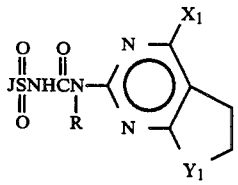
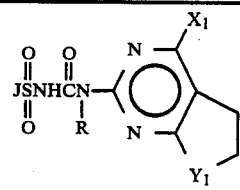

| J | R | R₁ | R₂ | X₁ | Y₁ | m.p. (°C.) | J | R | R₁ | R₂ | X₁ | Y₁ | m.p. (°C.) |
|---|---|---|---|---|---|---|---|---|---|---|---|---|---|
| J-1 | H | CH₃ | H | CH₃ | CH₂ | | J-1 | H | CH₂CH₃ | H | OCH₃ | CH₂ | |
| J-1 | H | CH₃ | H | CH₃ | O | 201–204 | J-1 | H | CH₂CH₃ | H | OCH₃ | O | |
| J-1 | H | CH₃ | H | OCH₃ | CH₂ | | J-2 | H | CH₃ | — | CH₃ | CH₂ | |
| J-1 | H | CH₃ | H | OCH₃ | O | | J-2 | H | CH₃ | — | CH₃ | O | |
| J-1 | H | CH₃ | H | OCH₂CH₃ | CH₂ | | J-2 | H | CH₃ | — | OCH₃ | CH₂ | |
| J-1 | H | CH₃ | H | OCH₂CH₃ | O | | J-2 | H | CH₃ | — | OCH₃ | O | |
| J-1 | H | CH₃ | H | OCF₂H | CH₂ | | J-3 | H | CH₃ | — | CH₃ | CH₂ | |
| J-1 | H | CH₃ | H | OCF₂H | O | | J-3 | H | CH₃ | — | CH₃ | O | |
| J-1 | CH₃ | CH₃ | H | CH₃ | O | | J-3 | H | CH₃ | — | OCH₃ | CH₂ | |
| J-1 | H | CH₃ | 3-OCH₃ | CH₃ | CH₂ | | J-3 | H | CH₃ | — | OCH₃ | O | |
| J-1 | H | CH₃ | 5-Cl | CH₃ | O | | J-4 | H | CH₃ | — | CH₃ | CH₂ | |
| J-1 | H | CH₃ | 5-OCH₃ | OCH₃ | CH₂ | | J-4 | H | CH₃ | — | CH₃ | O | |
| J-1 | H | CH₃ | 6-SCH₃ | OCH₃ | O | | J-4 | H | CH₃ | — | OCH₃ | CH₂ | |
| J-1 | H | CH₂CH₃ | H | CH₃ | CH₂ | | J-4 | H | CH₃ | — | OCH₃ | O | |
| J-1 | H | CH₂CH₃ | H | CH₃ | O | | J-5 | H | CH₃ | — | CH₃ | CH₂ | |
| | | | | | | | J-5 | H | CH₃ | — | CH₃ | O | |

TABLE 2-continued

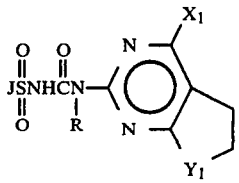

| J | R | R₁ | R₂ | X₁ | Y₁ | m.p. (°C.) |
|---|---|---|---|---|---|---|
| J-5 | H | CH₃ | — | OCH₃ | CH₂ | |
| J-5 | H | CH₃ | — | OCH₃ | O | |
| J-1 | H | (CH₂)₂CH₃ | — | CH₃ | O | |
| J-1 | H | CH₂CH=CH₂ | — | CH₃ | O | |

TABLE 3

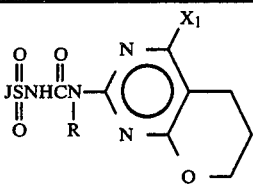

| J | R | R₁ | R₂ | X₁ | m.p. (°C.) |
|---|---|---|---|---|---|
| J-1 | H | CH₃ | H | CH₃ | |
| J-1 | H | CH₃ | H | OCH₃ | |
| J-1 | H | CH₃ | H | OCH₂CH₃ | |
| J-1 | H | CH₃ | H | OCF₂H | |
| J-1 | CH₃ | CH₃ | H | CH₃ | |
| J-1 | H | CH₃ | 3-OCH₃ | CH₃ | |
| J-1 | H | CH₃ | 3-F | OCH₃ | |
| J-1 | H | CH₃ | 5-Cl | CH₃ | |
| J-1 | H | CH₃ | 5-OCH₃ | OCH₃ | |
| J-1 | H | CH₃ | 6-Cl | CH₃ | |
| J-1 | H | CH₃ | 6-SCH₃ | OCH₃ | |
| J-1 | H | C(CH₃)₃ | H | CH₃ | |
| J-1 | H | CH₂CH=CH₂ | H | OCH₃ | |
| J-1 | H | CH₂CH₃ | H | OCH₂CH₃ | |
| J-1 | H | CH₂CH₃ | H | OCF₂H | |
| J-2 | H | CH₃ | — | CH₃ | |
| J-2 | H | CH₃ | — | OCH₃ | |
| J-2 | H | CH₃ | — | OCH₂CH₃ | |
| J-2 | H | CH₃ | — | OCF₂H | |
| J-3 | H | CH₃ | — | CH₃ | |
| J-3 | H | CH₃ | — | OCH₃ | |
| J-4 | H | CH₃ | — | CH₃ | |
| J-4 | H | CH₃ | — | OCH₃ | |
| J-5 | H | CH₃ | — | CH₃ | |
| J-5 | H | CH₃ | — | OCH₃ | |
| J-5 | H | CH₃ | — | OCH₂CH₃ | |
| J-5 | H | CH₃ | — | OCF₂H | |

TABLE 4

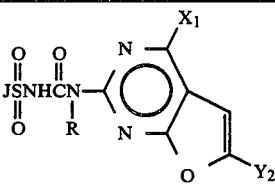

| J | R | R₁ | R₂ | X₁ | Y₂ | m.p. (°C.) |
|---|---|---|---|---|---|---|
| J-1 | H | CH₃ | H | CH₃ | H | |
| J-1 | H | CH₃ | H | CH₃ | CH₃ | |
| J-1 | H | CH₃ | H | OCH₃ | H | |
| J-1 | H | CH₃ | H | OCH₃ | CH₃ | |
| J-1 | H | CH₃ | H | OCH₂CH₃ | H | |
| J-1 | H | CH₃ | H | OCH₂CH₃ | CH₃ | |
| J-1 | H | CH₃ | H | OCF₂H | H | |
| J-1 | H | CH₃ | H | OCF₂H | CH₃ | |
| J-1 | CH₃ | CH₃ | H | CH₃ | CH₃ | |

TABLE 4-continued

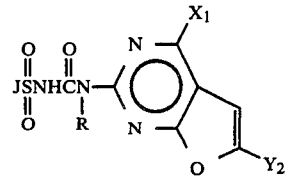

| J | R | R₁ | R₂ | X₁ | Y₂ | m.p. (°C.) |
|---|---|---|---|---|---|---|
| J-1 | H | CH₃ | 3-OCH₃ | CH₃ | H | |
| J-1 | H | CH₃ | 5-Cl | CH₃ | CH₃ | |
| J-1 | H | CH₃ | 5-OCH₃ | OCH₃ | H | |
| J-1 | H | CH₃ | 6-SCH₃ | OCH₃ | CH₃ | |
| J-1 | H | CH₂CH₃ | H | CH₃ | H | |
| J-1 | H | CH₂CH₃ | H | CH₃ | CH₃ | |
| J-1 | H | CH₂CH₃ | H | OCH₃ | H | |
| J-1 | H | CH₂CH₃ | H | OCH₃ | CH₃ | |
| J-2 | H | CH₃ | — | CH₃ | H | |
| J-2 | H | CH₃ | — | CH₃ | CH₃ | |
| J-2 | H | CH₃ | — | OCH₃ | H | |
| J-2 | H | CH₃ | — | OCH₃ | CH₃ | |
| J-3 | H | CH₃ | — | CH₃ | H | |
| J-3 | H | CH₃ | — | CH₃ | CH₃ | |
| J-3 | H | CH₃ | — | OCH₃ | H | |
| J-3 | H | CH₃ | — | OCH₃ | CH₃ | |
| J-4 | H | CH₃ | — | CH₃ | H | |
| J-4 | H | CH₃ | — | CH₃ | CH₃ | |
| J-4 | H | CH₃ | — | OCH₃ | H | |
| J-4 | H | CH₃ | — | OCH₃ | CH₃ | |
| J-5 | H | CH₃ | — | CH₃ | H | |
| J-5 | H | CH₃ | — | CH₃ | CH₃ | |
| J-5 | H | CH₃ | — | OCH₃ | H | |
| J-5 | H | CH₃ | — | OCH₃ | CH₃ | |

TABLE 5

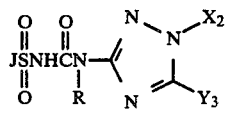

| J | R | R₁ | R₂ | X₂ | Y₃ | m.p. (°C.) |
|---|---|---|---|---|---|---|
| J-1 | H | CH₃ | H | CH₃ | OCH₃ | |
| J-1 | H | CH₃ | H | CH₃ | OCH₂CH₃ | |
| J-1 | H | CH₃ | H | CH₃ | SCH₃ | |
| J-1 | H | CH₃ | H | CH₃ | CH₃ | |
| J-1 | H | CH₃ | H | CH₃ | CH₂CH₃ | |
| J-1 | H | CH₃ | H | CH₂CH₃ | OCH₃ | |
| J-1 | H | CH₃ | H | CH₂CH₃ | OCH₂CH₃ | |
| J-1 | H | CH₃ | H | CH₂CH₃ | SCH₃ | |
| J-1 | H | CH₃ | H | CH₂CH₃ | CH₃ | |
| J-1 | H | CH₃ | H | CH₂CH₃ | CH₂CH₃ | |
| J-1 | H | CH₃ | H | CH₂CF₃ | OCH₃ | |
| J-1 | H | CH₃ | H | CH₂CF₃ | OCH₂CH₃ | |
| J-1 | H | CH₃ | H | CH₂CF₃ | SCH₃ | |
| J-1 | H | CH₃ | H | CH₂CF₃ | CH₃ | |
| J-1 | H | CH₃ | H | CH₂CF₃ | CH₂CH₃ | |
| J-1 | CH₃ | CH₃ | H | CH₃ | OCH₃ | |
| J-1 | H | CH₃ | 3-SCH₃ | CH₃ | CH₃ | |
| J-1 | H | CH₃ | 5-CH₃ | CH₂CH₃ | OCH₃ | |
| J-1 | H | CH₃ | 6-OCH₃ | CH₃ | OCH₂CH₃ | |
| J-1 | H | CH₂CH₃ | H | CH₃ | CH₃ | |
| J-1 | H | CH₂CH₃ | H | CH₃ | OCH₃ | |
| J-1 | H | CH₂CH₃ | H | CH₃ | OCH₂CH₃ | |
| J-1 | H | CH₂CH₃ | H | CH₂CH₃ | OCH₃ | |
| J-2 | H | CH₃ | — | CH₃ | CH₃ | |
| J-2 | H | CH₃ | — | CH₂CF₃ | OCH₃ | |
| J-2 | H | CH₃ | — | CH₃ | OCH₂CH₃ | |
| J-2 | H | CH₃ | — | CH₃ | SCH₃ | |
| J-2 | H | CH₃ | — | CH₃ | CH₂CH₃ | |
| J-3 | H | CH₃ | — | CH₃ | CH₃ | |
| J-3 | H | CH₃ | — | CH₂CF₃ | OCH₃ | |
| J-3 | H | CH₃ | — | CH₃ | OCH₂CH₃ | |
| J-3 | H | CH₃ | — | CH₃ | SCH₃ | |
| J-3 | H | CH₃ | — | CH₃ | CH₂CH₃ | |
| J-4 | H | CH₃ | — | CH₃ | CH₃ | |
| J-4 | H | CH₃ | — | CH₂CF₃ | OCH₃ | |
| J-4 | H | CH₃ | — | CH₃ | OCH₂CH₃ | |

TABLE 5-continued

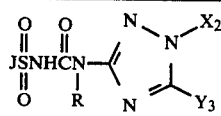

| J | R | R₁ | R₂ | X₂ | Y₃ | m.p. (°C.) |
|---|---|---|---|---|---|---|
| J-4 | H | CH₃ | — | CH₃ | SCH₃ | |
| J-4 | H | CH₃ | — | CH₃ | CH₂CH₃ | |
| J-5 | H | CH₃ | — | CH₃ | CH₃ | |
| J-5 | H | CH₃ | — | CH₂CF₃ | OCH₃ | |
| J-5 | H | CH₃ | — | CH₃ | OCH₂CH₃ | |
| J-5 | H | CH₃ | — | CH₃ | SCH₃ | |
| J-5 | H | CH₃ | — | CH₃ | CH₂CH₃ | |

TABLE 6

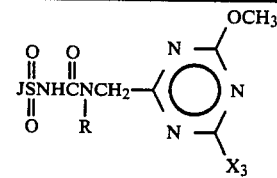

| J | R | R₁ | R₂ | X₃ | m.p. (°C.) |
|---|---|---|---|---|---|
| J-1 | H | CH₃ | H | CH₃ | |
| J-1 | H | CH₃ | H | OCH₃ | |
| J-1 | CH₃ | CH₃ | H | CH₃ | |
| J-1 | CH₃ | CH₃ | H | OCH₃ | |
| J-1 | H | CH₃ | 3-SCH₃ | CH₃ | |
| J-1 | H | CH₃ | 5-CH₃ | OCH₃ | |
| J-1 | H | CH₃ | 6-OCH₃ | OCH₃ | |
| J-1 | H | CH₃CH₂ | H | CH₃ | |
| J-1 | H | CH₃CH₂ | H | OCH₃ | |
| J-2 | H | CH₃ | H | CH₃ | |
| J-2 | H | CH₃ | H | OCH₃ | |
| J-3 | H | CH₃ | H | CH₃ | |
| J-3 | H | CH₃ | H | OCH₃ | |
| J-4 | H | CH₃ | H | CH₃ | |
| J-4 | H | CH₃ | H | OCH₃ | |
| J-5 | H | CH₃ | H | CH₃ | |
| J-5 | H | CH₃ | H | OCH₃ | |

TABLE 7

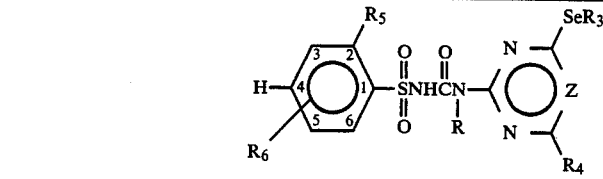

| R | R₅ | R₆ | R₃ | R₄ | Z | m.p. (°C.) |
|---|---|---|---|---|---|---|
| H | CH₃ | H | CH₃ | OCH₃ | CH | |
| H | (CH₂)₃CH₃ | H | CH₃ | CH₃ | CH | |
| H | OCH₃ | H | CH₃ | CH₃ | N | |
| H | O(CH₂)₃CH₃ | H | CH₃ | OCH₃ | N | |
| H | OCH₃ | 6-OCH₃ | CH₃ | OCH₃ | CH | |
| H | OCH₃ | 5-F | CH₃ | CH₃ | N | |
| H | OCH₂CH₂OCH₃ | H | CH₃ | OCH₃ | N | |
| H | F | H | CH₃ | CH₃ | CH | |
| H | Br | H | CH₃ | OCH₃ | CH | |
| H | CF₃ | H | CH₃ | CH₃ | CH | |
| H | CF₃ | H | CH₃ | OCH₃ | CH | |
| H | CF₃ | H | CH₃ | CH₃ | N | |
| H | CF₃ | H | CH₃ | OCH₃ | N | |
| CH₃ | CO₂CH₃ | H | CH₃ | OCH₃ | N | |
| H | CO₂(CH₂)₃CH₃ | H | CH₃ | CH₃ | CH | |
| H | CO₂CH₂CH₂OCH₃ | H | CH₃ | OCH₃ | N | |
| H | CO₂CH₂CH₂Cl | H | CH₃ | OCH₃ | CH | |
| H | CO₂CH₂CH=CH₂ | H | CH₃ | CH₃ | CH | |
| H | CO₂CH₃ | 3-F | CH₃ | OCH₃ | CH | |
| H | CO₂CH₃ | 3-Cl | CH₃ | OCH₃ | N | |
| H | CO₂CH₃ | 3-CH₃ | CH₃ | CH₃ | CH | |
| H | CO₂CH₃ | 3-CH₃ | CH₃ | OCH₃ | CH | |
| H | CO₂CH₃ | 3-CH₃ | CH₃ | OCH₃ | N | |
| H | CO₂CH₃ | 3-OCH₃ | CH₃ | OCH₃ | CH | |
| H | CO₂CH₃ | 3-SCH₃ | CH₃ | OCH₃ | CH | |
| H | CO₂CH₃ | 5-F | CH₃ | CH₃ | CH | |
| H | CO₂CH₃ | 5-F | CH₃ | OCH₃ | CH | |
| H | CO₂CH₃ | 5-F | CH₃ | CH₃ | N | |
| H | CO₂CH₃ | 5-F | CH₃ | OCH₃ | N | |
| H | CO₂CH₃ | 5-Cl | CH₃ | OCH₃ | CH | |
| H | CO₂CH₃ | 5-Br | CH₃ | OCH₃ | CH | |
| H | CO₂CH₃ | 5-CF₃ | CH₃ | CH₃ | CH | 158–162 (d) |
| H | CO₂CH₃ | 5-CF₃ | CH₃ | OCH₃ | CH | 173–175 |
| H | CO₂CH₃ | 5-CF₃ | CH₃ | CH₃ | N | |
| H | CO₂CH₃ | 5-CF₃ | CH₃ | OCH₃ | N | 153–155 |
| H | CO₂CH₃ | 5-CH₃ | CH₃ | CH₃ | CH | |
| H | CO₂CH₃ | 5-CH₃ | CH₃ | OCH₃ | CH | 183–185 |
| H | CO₂CH₃ | 5-CH₃ | CH₃ | CH₃ | N | |
| H | CO₂CH₃ | 5-CH₃ | CH₃ | OCH₃ | N | |
| H | CO₂CH₃ | 5-OCH₃ | CH₃ | CH₃ | CH | |

TABLE 7-continued

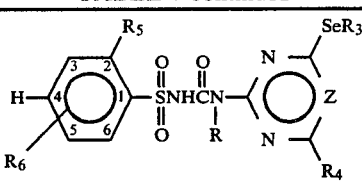

| R | $R_5$ | $R_6$ | $R_3$ | $R_4$ | Z | m.p. (°C.) |
|---|---|---|---|---|---|---|
| H | $CO_2CH_3$ | 5-$OCH_3$ | $CH_3$ | $OCH_3$ | CH | |
| H | $CO_2CH_3$ | 5-$OCH_3$ | $CH_3$ | $CH_3$ | N | |
| H | $CO_2CH_3$ | 5-$OCH_3$ | $CH_3$ | $OCH_3$ | N | |
| H | $CO_2CH_3$ | 5-$SCH_3$ | $CH_3$ | $OCH_3$ | CH | |
| H | $CO_2CH_3$ | 5-$OCF_2H$ | $CH_3$ | $OCH_3$ | CH | |
| H | $CO_2CH_3$ | 6-F | $CH_3$ | $CH_3$ | CH | |
| H | $CO_2CH_3$ | 6-Cl | $CH_3$ | $CH_3$ | CH | |
| H | $CO_2CH_3$ | 6-Cl | $CH_3$ | $OCH_3$ | CH | |
| H | $CO_2CH_3$ | 6-$CH_3$ | $CH_3$ | $OCH_3$ | CH | |
| H | $CO_2CH_3$ | 6-$CH_3$ | $CH_3$ | $OCH_3$ | N | |
| H | $CO_2CH_3$ | 6-$OCH_3$ | $CH_3$ | $CH_3$ | CH | |
| H | $CO_2CH_3$ | 6-$OCH_3$ | $CH_3$ | $OCH_3$ | CH | |
| H | Cl | 5-Cl | $CH_3$ | $OCH_3$ | CH | |
| H | Cl | H | $CH_3$ | $CH_3$ | CH | |
| H | Cl | H | $CH_3$ | $OCH_3$ | CH | 194–196 |
| H | Cl | H | $CH_3$ | $CH_3$ | N | |
| H | Cl | H | $CH_3$ | $OCH_3$ | N | 170–180 |
| H | $NO_2$ | H | $CH_3$ | $CH_3$ | CH | |
| H | $NO_2$ | H | $CH_3$ | $OCH_3$ | CH | 198–200 |
| H | $NO_2$ | H | $CH_3$ | $CH_3$ | N | |
| H | $NO_2$ | H | $CH_3$ | $OCH_3$ | N | |
| H | $CO_2CH_3$ | H | $CH_3$ | $CH_3$ | CH | 185–188 (d) |
| H | $CO_2CH_3$ | H | $CH_3$ | $OCH_3$ | CH | 165–168 |
| H | $CO_2CH_3$ | H | $CH_3$ | $CH_3$ | N | |
| H | $CO_2CH_3$ | H | $CH_3$ | $OCH_3$ | N | 179–181 |
| H | $CO_2CH_2CH_3$ | H | $CH_3$ | $CH_3$ | CH | 165–167 |
| H | $CO_2CH_2CH_3$ | H | $CH_3$ | $OCH_3$ | CH | 172–175 |
| H | $CO_2CH_2CH_3$ | H | $CH_3$ | $CH_3$ | N | |
| H | $CO_2CH_2CH_3$ | H | $CH_3$ | $OCH_3$ | N | 186–188 |
| H | $SO_2N(CH_3)_2$ | H | $CH_3$ | $CH_3$ | CH | |
| H | $SO_2N(CH_3)_2$ | H | $CH_3$ | $OCH_3$ | CH | 208–211 |
| H | $SO_2N(CH_3)_2$ | H | $CH_3$ | $CH_3$ | N | |
| H | $SO_2N(CH_3)_2$ | H | $CH_3$ | $OCH_3$ | N | |
| H | $SO_2N(CH_3)(CH_2CH_2CH_3)$ | H | $CH_3$ | $OCH_3$ | CH | |
| H | $SO_2N(OCH_3)CH_3$ | H | $CH_3$ | $OCH_3$ | CH | |
| H | $OSO_2CH_3$ | H | $CH_3$ | $CH_3$ | CH | 207–210 (d) |
| H | $OSO_2CH_3$ | H | $CH_3$ | $OCH_3$ | CH | 175–180 |
| H | $OSO_2CH_3$ | H | $CH_3$ | $CH_3$ | N | |
| H | $OSO_2CH_3$ | H | $CH_3$ | $OCH_3$ | N | 180–184 |
| H | $OSO_2CH_3$ | $CH_3$ | $CH_3$ | $OCH_3$ | CH | |
| $CH_3$ | $OSO_2CH_3$ | H | $CH_3$ | $OCH_3$ | N | |
| H | $OSO_2CH(CH_3)_2$ | H | $CH_3$ | $CH_3$ | CH | |
| H | $OSO_2(CH_2)_2CH_3$ | H | $CH_3$ | $OCH_3$ | CH | |
| H | $OSO_2N(CH_3)_2$ | H | $CH_3$ | $CH_3$ | N | |
| H | $SCH_3$ | H | $CH_3$ | $OCH_3$ | CH | |
| H | $S(CH_2)_2CH_3$ | H | $CH_3$ | $OCH_3$ | N | |
| H | $SCH_2CH=CH_2$ | H | $CH_3$ | $OCH_3$ | CH | |
| H | $SO_2CH_3$ | H | $CH_3$ | $CH_3$ | CH | 212–215 (d) |
| H | $SO_2CH_3$ | H | $CH_3$ | $OCH_3$ | CH | 207–210 |
| H | $SO_2CH_3$ | H | $CH_3$ | $CH_3$ | N | |
| H | $SO_2CH_3$ | H | $CH_3$ | $OCH_3$ | N | |
| H | $SO_2CH_3$ | 3-$CH_3$ | $CH_3$ | $CH_3$ | N | |
| H | $SO_2CH_3$ | 3-$OCH_3$ | $CH_3$ | $OCH_3$ | CH | |
| H | $SO_2CH_3$ | 5-$CF_3$ | $CH_3$ | $OCH_3$ | N | |
| $CH_3$ | $SO_2CH_3$ | H | $CH_3$ | $OCH_3$ | N | |
| H | $SO_2(CH_2)_2CH_3$ | H | $CH_3$ | $CH_3$ | CH | |
| H | $SO_2(CH_2)_2CH_3$ | H | $CH_3$ | $OCH_3$ | CH | 180–185 |
| H | $SO_2(CH_2)_2CH_3$ | H | $CH_3$ | $CH_3$ | N | |
| H | $SO_2(CH_2)_2CH_3$ | H | $CH_3$ | $OCH_3$ | N | |
| H | $SO_2CH_2CH=CH_2$ | H | $CH_3$ | $OCH_3$ | CH | |
| H | $OCF_3$ | H | $CH_3$ | $CH_3$ | CH | |
| H | $SCF_3$ | H | $CH_3$ | $OCH_3$ | N | |
| H | $SO_2CF_3$ | H | $CH_3$ | $CH_3$ | N | |
| H | $OCHF_2$ | H | $CH_3$ | $OCH_3$ | CH | |
| H | $SCHF_2$ | H | $CH_3$ | $CH_3$ | CH | |
| H | $SO_2CHF_2$ | H | $CH_3$ | $OCH_3$ | N | |
| H | $OCH_2CH=CH_2$ | H | $CH_3$ | $OCH_3$ | CH | |
| H | $OCH_2CH=CHCH_2$ | H | $CH_3$ | $OCH_3$ | CH | |
| H | $OCH_2C\equiv CH$ | H | $CH_3$ | $OCH_3$ | N | |
| H | $OCH_2C\equiv CCH_3$ | H | $CH_3$ | $CH_3$ | CH | |
| H | $CH_2OCH_3$ | H | $CH_3$ | $CH_3$ | N | |
| H | $CH_2CH_2OCH_3$ | H | $CH_3$ | $OCH_3$ | N | |

TABLE 7-continued

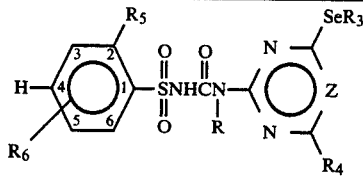

| R | R5 | R6 | R3 | R4 | Z | m.p. (°C.) |
|---|---|---|---|---|---|---|
| H | CH2OCH2CH3 | H | CH3 | OCH3 | CH | |
| H | CH2CH2OCH2CH3 | H | CH3 | CH3 | CH | |
| H | C6H5 | H | CH3 | OCH3 | N | |
| H | 3,5-dimethyl-1,2,4-oxadiazol-yl | H | CH3 | OCH3 | CH | |
| H | 3-methyl-1,2,4-oxadiazol-5-yl | H | CH3 | CH3 | CH | |
| H | 5-methylisoxazol-3-yl | H | CH3 | OCH3 | CH | |
| H | 3-methylisoxazol-5-yl | H | CH3 | OCH3 | N | |
| H | 4-methyl-1,2,3-thiadiazol-5-yl | H | CH3 | OCH3 | CH | |
| H | 4-methylisoxazol-5-yl | H | CH3 | CH3 | N | |
| H | 1,3-dimethylpyrazol-5-yl | H | CH3 | OCH3 | N | |
| H | 1,3-dimethylpyrazol-5-yl | H | CH3 | CH3 | CH | |
| H | pyrazol-1-yl | H | CH3 | OCH3 | N | |
| H | 1,2,4-triazol-1-yl | H | CH3 | OCH3 | CH | |
| H | tetrahydrofuran-2-yl | H | CH3 | OCH3 | CH | |
| H | 5-methylfuran-2-yl | H | CH3 | CH3 | CH | |
| H | 5-methylthien-2-yl | H | CH3 | OCH3 | N | |

TABLE 7-continued

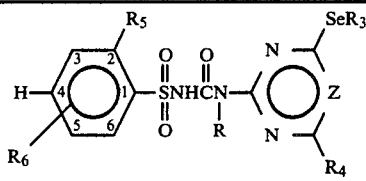

| R | R5 | R6 | R3 | R4 | Z | m.p. (°C.) |
|---|---|---|---|---|---|---|
| H | 2-furyl | H | CH3 | CH3 | N | |
| H | 2-pyrimidinyl | H | CH3 | OCH3 | CH | |
| H | CO2CH2CH3 | 3-CH3 | CH3 | OCH2CH3 | N | |
| H | CO2CH3 | H | CH3 | OCH2CH3 | CH | |
| H | CO2CH3 | H | CH3 | OCH2CH3 | N | |
| H | CO2CH3 | H | CH3 | OCH2CF3 | CH | |
| H | CO2CH3 | H | CH3 | OCH2CF3 | N | |
| H | CO2CH3 | H | CH3 | OCF2H | CH | |
| H | CO2CH3 | H | CH3 | CF3 | CH | |
| H | CO2CH3 | H | CH3 | CF3 | N | |
| H | CO2CH3 | H | CH3 | NHCH3 | CH | |
| H | CO2CH3 | H | CH3 | NHCH3 | N | |
| H | CO2CH3 | H | CH3 | N(CH3)2 | CH | |
| H | CO2CH3 | H | CH3 | N(CH3)2 | N | |
| H | CO2CH3 | H | CH2CH3 | CH3 | CH | |
| H | CO2CH3 | H | CH2CH3 | CH3 | N | |
| H | CO2CH3 | H | CH2CH3 | OCH3 | CH | |
| H | CO2CH3 | H | CH2CH3 | OCH3 | N | |
| H | CO2CH3 | H | CH2CH3 | OCH2CH3 | CH | |
| H | CO2CH3 | H | CH2CH3 | OCH2CH3 | N | |
| H | CO2CH3 | H | CH2CH3 | OCH2CF3 | CH | |
| H | CO2CH3 | H | CH2CH3 | OCH2CF3 | N | |
| H | CO2CH3 | H | CH2CH3 | OCF2H | CH | |
| H | CO2CH3 | H | CH2CH3 | CF3 | CH | |
| H | CO2CH3 | H | CH2CH3 | CF3 | N | |
| H | CO2CH3 | H | CH2CH3 | NHCH3 | CH | |
| H | CO2CH3 | H | CH2CH3 | NHCH3 | N | |
| H | CO2CH3 | H | CH2CH3 | N(CH3)2 | CH | |
| H | CO2CH3 | H | CH2CH3 | N(CH3)2 | N | |
| H | CO2CH3 | H | CF2H | CH3 | CH | |
| H | CO2CH3 | H | CF2H | CH3 | N | |
| H | CO2CH3 | H | CF2H | OCH3 | CH | |
| H | CO2CH3 | H | CF2H | OCH3 | N | |
| H | CO2CH3 | H | CF2H | OCH2CH3 | CH | |
| H | CO2CH3 | H | CF2H | OCH2CH3 | N | |
| H | CO2CH3 | H | CF2H | OCH2CF3 | CH | |
| H | CO2CH3 | H | CF2H | OCH2CF3 | N | |
| H | CO2CH3 | H | CF2H | OCF2H | CH | |
| H | CO2CH3 | H | CF2H | CF3 | CH | |
| H | CO2CH3 | H | CF2H | CF3 | N | |
| H | CO2CH3 | H | CF2H | NHCH3 | CH | |
| H | CO2CH3 | H | CF2H | NHCH3 | N | |
| H | CO2CH3 | H | CF2H | N(CH3)2 | CH | |
| H | CO2CH3 | H | CF2H | N(CH3)2 | N | |
| H | CO2CH2CH3 | H | CH3 | OCH2CH3 | CH | |
| H | CO2CH2CH3 | H | CH3 | OCH2CH3 | N | |
| H | CO2CH2CH3 | H | CH3 | OCH2CF3 | CH | |
| H | CO2CH2CH3 | H | CH3 | OCH2CF3 | N | |
| H | CO2CH2CH3 | H | CH3 | OCF2H | CH | |
| H | CO2CH2CH3 | H | CH3 | CF3 | CH | |
| H | CO2CH2CH3 | H | CH3 | CF3 | N | |
| H | CO2CH2CH3 | H | CH3 | NHCH3 | CH | |
| H | CO2CH2CH3 | H | CH3 | NHCH3 | N | |
| H | CO2CH2CH3 | H | CH3 | N(CH3)2 | CH | |
| H | CO2CH2CH3 | H | CH3 | N(CH3)2 | N | |
| H | CO2CH2CH3 | H | CH2CH3 | CH3 | CH | |
| H | CO2CH2CH3 | H | CH2CH3 | CH3 | N | |
| H | CO2CH2CH3 | H | CH2CH3 | OCH3 | CH | |
| H | CO2CH2CH3 | H | CH2CH3 | OCH3 | N | |
| H | CO2CH2CH3 | H | CH2CH3 | OCH2CH3 | CH | |
| H | CO2CH2CH3 | H | CH2CH3 | OCH2CH3 | N | |

TABLE 7-continued

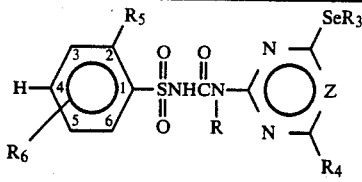

| R | R5 | R6 | R3 | R4 | Z | m.p. (°C.) |
|---|---|---|---|---|---|---|
| H | CO2CH2CH3 | H | CH2CH3 | OCH2CF3 | CH | |
| H | CO2CH2CH3 | H | CH2CH3 | OCH2CF3 | N | |
| H | CO2CH2CH3 | H | CH2CH3 | OCF2H | CH | |
| H | CO2CH2CH3 | H | CH2CH3 | CF3 | CH | |
| H | CO2CH2CH3 | H | CH2CH3 | CF3 | N | |
| H | CO2CH2CH3 | H | CH2CH3 | NHCH3 | CH | |
| H | CO2CH2CH3 | H | CH2CH3 | NHCH3 | N | |
| H | CO2CH2CH3 | H | CH2CH3 | N(CH3)2 | CH | |
| H | CO2CH2CH3 | H | CH2CH3 | N(CH3)2 | N | |
| H | CO2CH2CH3 | H | CF2H | CH3 | CH | |
| H | CO2CH2CH3 | H | CF2H | CH3 | N | |
| H | CO2CH2CH3 | H | CF2H | OCH3 | CH | |
| H | CO2CH2CH3 | H | CF2H | OCH3 | N | |
| H | CO2CH2CH3 | H | CF2H | OCH2CH3 | CH | |
| H | CO2CH2CH3 | H | CF2H | OCH2CH3 | N | |
| H | CO2CH2CH3 | H | CF2H | OCH2CF3 | CH | |
| H | CO2CH2CH3 | H | CF2H | OCH2CF3 | N | |
| H | CO2CH2CH3 | H | CF2H | OCF2H | CH | |
| H | CO2CH2CH3 | H | CF2H | CF3 | CH | |
| H | CO2CH2CH3 | H | CF2H | CF3 | N | |
| H | CO2CH2CH3 | H | CF2H | NHCH3 | CH | |
| H | CO2CH2CH3 | H | CF2H | NHCH3 | N | |
| H | CO2CH2CH3 | H | CF2H | N(CH3)2 | CH | |
| H | CO2CH2CH3 | H | CF2H | N(CH3)2 | N | |
| H | SO2N(CH3)2 | H | CH3 | OCH2CH3 | CH | |
| H | SO2N(CH3)2 | H | CH3 | OCH2CH3 | N | |
| H | SO2N(CH3)2 | H | CH3 | OCH2CF3 | CH | |
| H | SO2N(CH3)2 | H | CH3 | OCH2CF3 | N | |
| H | SO2N(CH3)2 | H | CH3 | OCF2H | CH | |
| H | SO2N(CH3)2 | H | CH3 | CF3 | CH | |
| H | SO2N(CH3)2 | H | CH3 | CF3 | N | |
| H | SO2N(CH3)2 | H | CH3 | NHCH3 | CH | |
| H | SO2N(CH3)2 | H | CH3 | NHCH3 | N | |
| H | SO2N(CH3)2 | H | CH3 | N(CH3)2 | CH | |
| H | SO2N(CH3)2 | H | CH3 | N(CH3)2 | N | |
| H | SO2N(CH3)2 | H | CH2CH3 | CH3 | CH | |
| H | SO2N(CH3)2 | H | CH2CH3 | CH3 | N | |
| H | SO2N(CH3)2 | H | CH2CH3 | OCH3 | CH | |
| H | SO2N(CH3)2 | H | CH2CH3 | OCH3 | N | |
| H | SO2N(CH3)2 | H | CH2CH3 | OCH2CH3 | CH | |
| H | SO2N(CH3)2 | H | CH2CH3 | OCH2CH3 | N | |
| H | SO2N(CH3)2 | H | CH2CH3 | OCH2CF3 | CH | |
| H | SO2N(CH3)2 | H | CH2CH3 | OCH2CF3 | N | |
| H | SO2N(CH3)2 | H | CH2CH3 | OCF2H | CH | |
| H | SO2N(CH3)2 | H | CH2CH3 | CF3 | CH | |
| H | SO2N(CH3)2 | H | CH2CH3 | CF3 | N | |
| H | SO2N(CH3)2 | H | CH2CH3 | NHCH3 | CH | |
| H | SO2N(CH3)2 | H | CH2CH3 | NHCH3 | N | |
| H | SO2N(CH3)2 | H | CH2CH3 | N(CH3)2 | CH | |
| H | SO2N(CH3)2 | H | CH2CH3 | N(CH3)2 | N | |
| H | SO2N(CH3)2 | H | CF2H | CH3 | CH | |
| H | SO2N(CH3)2 | H | CF2H | CH3 | N | |
| H | SO2N(CH3)2 | H | CF2H | OCH3 | CH | |
| H | SO2N(CH3)2 | H | CF2H | OCH3 | N | |
| H | SO2N(CH3)2 | H | CF2H | OCH2CH3 | CH | |
| H | SO2N(CH3)2 | H | CF2H | OCH2CH3 | N | |
| H | SO2N(CH3)2 | H | CF2H | OCH2CF3 | CH | |
| H | SO2N(CH3)2 | H | CF2H | OCH2CF3 | N | |
| H | SO2N(CH3)2 | H | CF2H | OCF2H | CH | |
| H | SO2N(CH3)2 | H | CF2H | CF3 | CH | |
| H | SO2N(CH3)2 | H | CF2H | CF3 | N | |
| H | SO2N(CH3)2 | H | CF2H | NHCH3 | CH | |
| H | SO2N(CH3)2 | H | CF2H | NHCH3 | N | |
| H | SO2N(CH3)2 | H | CF2H | N(CH3)2 | CH | |
| H | SO2N(CH3)2 | H | CF2H | N(CH3)2 | N | |
| H | SO2CH3 | H | CH3 | OCH2CH3 | CH | |
| H | SO2CH3 | H | CH3 | OCH2CH3 | N | |
| H | SO2CH3 | H | CH3 | OCH2CF3 | CH | |
| H | SO2CH3 | H | CH3 | OCH2CF3 | N | |
| H | SO2CH3 | H | CH3 | OCF2H | CH | |
| H | SO2CH3 | H | CH3 | CF3 | CH | |
| H | SO2CH3 | H | CH3 | CF3 | N | |

TABLE 7-continued

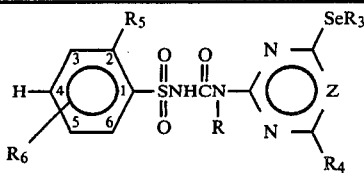

| R | $R_5$ | $R_6$ | $R_3$ | $R_4$ | Z | m.p. (°C.) |
|---|---|---|---|---|---|---|
| H | $SO_2CH_3$ | H | $CH_3$ | $NHCH_3$ | CH | |
| H | $SO_2CH_3$ | H | $CH_3$ | $NHCH_3$ | N | |
| H | $SO_2CH_3$ | H | $CH_3$ | $N(CH_3)_2$ | CH | |
| H | $SO_2CH_3$ | H | $CH_3$ | $N(CH_3)_2$ | N | |
| H | $SO_2CH_3$ | H | $CH_2CH_3$ | $CH_3$ | CH | |
| H | $SO_2CH_3$ | H | $CH_2CH_3$ | $CH_3$ | N | |
| H | $SO_2CH_3$ | H | $CH_2CH_3$ | $OCH_3$ | CH | |
| H | $SO_2CH_3$ | H | $CH_2CH_3$ | $OCH_3$ | N | |
| H | $SO_2CH_3$ | H | $CH_2CH_3$ | $OCH_2CH_3$ | CH | |
| H | $SO_2CH_3$ | H | $CH_2CH_3$ | $OCH_2CH_3$ | N | |
| H | $SO_2CH_3$ | H | $CH_2CH_3$ | $OCH_2CF_3$ | CH | |
| H | $SO_2CH_3$ | H | $CH_2CH_3$ | $OCH_2CF_3$ | N | |
| H | $SO_2CH_3$ | H | $CH_2CH_3$ | $OCF_2H$ | CH | |
| H | $SO_2CH_3$ | H | $CH_2CH_3$ | $CF_3$ | CH | |
| H | $SO_2CH_3$ | H | $CH_2CH_3$ | $CF_3$ | N | |
| H | $SO_2CH_3$ | H | $CH_2CH_3$ | $NHCH_3$ | CH | |
| H | $SO_2CH_3$ | H | $CH_2CH_3$ | $NHCH_3$ | N | |
| H | $SO_2CH_3$ | H | $CH_2CH_3$ | $N(CH_3)_2$ | CH | |
| H | $SO_2CH_3$ | H | $CH_2CH_3$ | $N(CH_3)_2$ | N | |
| H | $SO_2CH_3$ | H | $CF_2H$ | $CH_3$ | CH | |
| H | $SO_2CH_3$ | H | $CF_2H$ | $CH_3$ | N | |
| H | $SO_2CH_3$ | H | $CF_2H$ | $OCH_3$ | CH | |
| H | $SO_2CH_3$ | H | $CF_2H$ | $OCH_3$ | N | |
| H | $SO_2CH_3$ | H | $CF_2H$ | $OCH_2CH_3$ | CH | |
| H | $SO_2CH_3$ | H | $CF_2H$ | $OCH_2CH_3$ | N | |
| H | $SO_2CH_3$ | H | $CF_2H$ | $OCH_2CF_3$ | CH | |
| H | $SO_2CH_3$ | H | $CF_2H$ | $OCH_2CF_3$ | N | |
| H | $SO_2CH_3$ | H | $CF_2H$ | $OCF_2H$ | CH | |
| H | $SO_2CH_3$ | H | $CF_2H$ | $CF_3$ | CH | |
| H | $SO_2CH_3$ | H | $CF_2H$ | $CF_3$ | N | |
| H | $SO_2CH_3$ | H | $CF_2H$ | $NHCH_3$ | CH | |
| H | $SO_2CH_3$ | H | $CF_2H$ | $NHCH_3$ | N | |
| H | $SO_2CH_3$ | H | $CF_2H$ | $N(CH_3)_2$ | CH | |
| H | $SO_2CH_3$ | H | $CF_2H$ | $N(CH_3)_2$ | N | |
| H | $OSO_2CH_3$ | H | $CH_3$ | $OCH_2CH_3$ | CH | |
| H | $OSO_2CH_3$ | H | $CH_3$ | $OCH_2CH_3$ | N | |
| H | $OSO_2CH_3$ | H | $CH_3$ | $OCH_2CF_3$ | CH | |
| H | $OSO_2CH_3$ | H | $CH_3$ | $OCH_2CF_3$ | N | |
| H | $OSO_2CH_3$ | H | $CH_3$ | $OCF_2H$ | CH | |
| H | $OSO_2CH_3$ | H | $CH_3$ | $CF_3$ | CH | |
| H | $OSO_2CH_3$ | H | $CH_3$ | $CF_3$ | N | |
| H | $OSO_2CH_3$ | H | $CH_3$ | $NHCH_3$ | CH | |
| H | $OSO_2CH_3$ | H | $CH_3$ | $NHCH_3$ | N | |
| H | $OSO_2CH_3$ | H | $CH_3$ | $N(CH_3)_2$ | CH | |
| H | $OSO_2CH_3$ | H | $CH_3$ | $N(CH_3)_2$ | N | |
| H | $OSO_2CH_3$ | H | $CH_2CH_3$ | $CH_3$ | CH | |
| H | $OSO_2CH_3$ | H | $CH_2CH_3$ | $CH_3$ | N | |
| H | $OSO_2CH_3$ | H | $CH_2CH_3$ | $OCH_3$ | CH | |
| H | $OSO_2CH_3$ | H | $CH_2CH_3$ | $OCH_3$ | N | |
| H | $OSO_2CH_3$ | H | $CH_2CH_3$ | $OCH_2CH_3$ | CH | |
| H | $OSO_2CH_3$ | H | $CH_2CH_3$ | $OCH_2CH_3$ | N | |
| H | $OSO_2CH_3$ | H | $CH_2CH_3$ | $OCH_2CF_3$ | CH | |
| H | $OSO_2CH_3$ | H | $CH_2CH_3$ | $OCH_2CF_3$ | N | |
| H | $OSO_2CH_3$ | H | $CH_2CH_3$ | $OCF_2H$ | CH | |
| H | $OSO_2CH_3$ | H | $CH_2CH_3$ | $CF_3$ | CH | |
| H | $OSO_2CH_3$ | H | $CH_2CH_3$ | $CF_3$ | N | |
| H | $OSO_2CH_3$ | H | $CH_2CH_3$ | $NHCH_3$ | CH | |
| H | $OSO_2CH_3$ | H | $CH_2CH_3$ | $NHCH_3$ | N | |
| H | $OSO_2CH_3$ | H | $CH_2CH_3$ | $N(CH_3)_2$ | CH | |
| H | $OSO_2CH_3$ | H | $CH_2CH_3$ | $N(CH_3)_2$ | N | |
| H | $OSO_2CH_3$ | H | $CF_2H$ | $CH_3$ | CH | |
| H | $OSO_2CH_3$ | H | $CF_2H$ | $CH_3$ | N | |
| H | $OSO_2CH_3$ | H | $CF_2H$ | $OCH_3$ | CH | |
| H | $OSO_2CH_3$ | H | $CF_2H$ | $OCH_3$ | N | |
| H | $OSO_2CH_3$ | H | $CF_2H$ | $OCH_2CH_3$ | CH | |
| H | $OSO_2CH_3$ | H | $CF_2H$ | $OCH_2CH_3$ | N | |
| H | $OSO_2CH_3$ | H | $CF_2H$ | $OCH_2CF_3$ | CH | |
| H | $OSO_2CH_3$ | H | $CF_2H$ | $OCH_2CF_3$ | N | |
| H | $OSO_2CH_3$ | H | $CF_2H$ | $OCF_2H$ | CH | |
| H | $OSO_2CH_3$ | H | $CF_2H$ | $CF_3$ | CH | |
| H | $OSO_2CH_3$ | H | $CF_2H$ | $CF_3$ | N | |
| H | $OSO_2CH_3$ | H | $CF_2H$ | $NHCH_3$ | CH | |

TABLE 7-continued

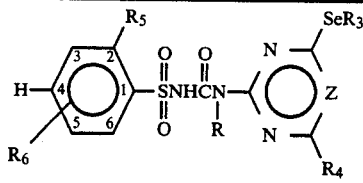

| R | R5 | R6 | R3 | R4 | Z | m.p. (°C.) |
|---|---|---|---|---|---|---|
| H | OSO2CH3 | H | CF2H | NHCH3 | N | |
| H | OSO2CH3 | H | CF2H | N(CH3)2 | CH | |
| H | OSO2CH3 | H | CF2H | N(CH3)2 | N | |

TABLE 8

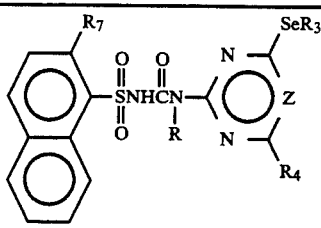

| R | R7 | R3 | R4 | Z | m.p. (°C.) |
|---|---|---|---|---|---|
| H | H | CH3 | OCH3 | CH | |
| H | CH3 | CH3 | CH3 | CH | |
| H | CH3 | CH3 | OCH3 | CH | |
| H | CH3 | CH3 | CH3 | N | |
| H | CH3 | CH3 | OCH3 | N | |
| H | F | CH3 | OCH3 | N | |
| H | Cl | CH3 | CH3 | CH | |
| H | Cl | CH3 | OCH3 | CH | |
| H | Cl | CH3 | CH3 | N | |
| H | Cl | CH3 | OCH3 | N | |
| H | Cl | CH3 | OCH2CH3 | CH | |
| H | Cl | CH3 | OCH2CF3 | N | |
| H | Cl | CH3 | OCF2H | CH | |
| H | Cl | CH3 | CF3 | CH | |
| H | Cl | CH3 | NHCH3 | N | |
| H | Cl | CH3 | N(CH3)2 | CH | |
| H | Cl | CH2CH3 | OCH3 | N | |
| H | Cl | CHF2 | CH3 | CH | |
| H | Cl | CHF2 | OCH3 | CH | |
| CH3 | Cl | CH3 | OCH3 | N | |
| H | Br | CH3 | CH3 | CH | |
| H | OCH3 | CH3 | CH3 | CH | |
| H | OCH3 | CH3 | OCH3 | CH | |
| H | OCH3 | CH3 | CH3 | N | |
| H | OCH3 | CH3 | OCH3 | N | |
| H | OCH3 | CH3 | OCH2CH3 | N | |
| H | SO2N(CH3)2 | CH3 | CH3 | CH | |
| H | OSO2CH3 | CH3 | OCH3 | N | |
| H | SCH3 | CH3 | CH3 | CH | |
| H | SCH3 | CH3 | OCH3 | CH | |
| H | SCH3 | CH3 | CH3 | N | |
| H | SCH3 | CH3 | OCH3 | N | |
| H | SCH3 | CH2CH3 | OCH3 | CH | |
| H | SO2CH3 | CH3 | OCH3 | N | |
| CH3 | SO2CH3 | CH3 | OCH3 | CH | |

TABLE 9

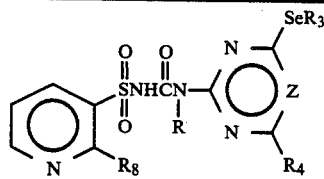

| R | R8 | R3 | R4 | Z | m.p. (°C.) |
|---|---|---|---|---|---|
| H | CH3 | CH3 | CH3 | CH | |
| H | CH2CH3 | CH3 | OCH3 | N | |
| H | OCH3 | CH3 | CH3 | N | |
| H | OCH2CH3 | CH3 | OCH3 | CH | |
| H | F | CH3 | OCH3 | N | |
| H | Cl | CH3 | CH3 | CH | |
| H | Cl | CH3 | OCH3 | CH | |
| H | Cl | CH3 | CH3 | N | |
| H | Cl | CH3 | OCH3 | N | |
| H | Br | CH3 | CH3 | CH | |
| H | SO2N(CH3)2 | CH3 | CH3 | CH | |
| H | SO2N(CH3)2 | CH3 | OCH3 | CH | |
| H | SO2N(CH3)2 | CH3 | CH3 | N | |
| H | SO2N(CH3)2 | CH3 | OCH3 | N | |
| H | SO2N(CH3)2 | CH3 | OCH2CH3 | N | |
| H | SO2N(CH3)2 | CH3 | OCH2CF3 | CH | |
| H | SO2N(CH3)2 | CH3 | OCF2H | CH | |
| H | SO2N(CH3)2 | CH3 | CF3 | CH | |
| H | SO2N(CH3)2 | CH3 | NHCH3 | CH | |
| H | SO2N(CH3)2 | CH3 | N(CH3)2 | N | |
| H | SO2N(CH3)2 | CH2CH3 | OCH3 | N | |
| H | SO2N(CH3)2 | CH2CH3 | OCF2H | CH | |
| H | SO2N(CH3)2 | CHF2 | OCH3 | CH | |
| H | SO2N(CH3)2 | CHF2 | OCH2CF3 | CH | |
| CH3 | SO2N(CH3)2 | CH3 | OCH3 | CH | |
| H | SO2N(CH2CH3)2 | CH3 | OCH3 | N | |
| H | SO2N(CH3)(CH2)2CH3 | CH3 | CH3 | CH | |
| H | SO2N(OCH3)CH3 | CH3 | CH3 | CH | |
| H | SO2N(OCH3)CH3 | CH3 | OCH3 | CH | |
| H | SO2N(OCH3)CH3 | CH3 | CH3 | N | |
| H | SO2N(OCH3)CH3 | CH3 | OCH3 | N | |
| H | SO2CH3 | CH3 | CH3 | CH | |
| H | SO2CH3 | CH3 | OCH3 | CH | |
| H | SO2CH3 | CH3 | CH3 | N | |
| H | SO2CH3 | CH3 | OCH3 | N | |
| H | SO2CH3 | CH2CH3 | OCH3 | N | |
| H | SO2CH3 | CH3 | OCF2H | CH | |
| CH3 | SO2CH3 | CH3 | CH3 | CH | |
| H | SO2CH2CH3 | CH3 | CH3 | N | |
| H | SO2(CH2)2CH3 | CH3 | OCH3 | N | |
| H | SO2CH(CH3)2 | CH3 | OCH3 | CH | |
| H | SO2CH2CH=CH2 | CH3 | OCH3 | N | |

TABLE 10

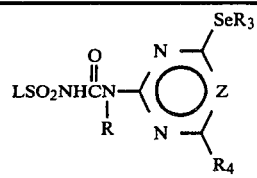

| L | R | R9 | R3 | R4 | Z | m.p. (°C.) |
|---|---|---|---|---|---|---|
| L-4 | H | CH3 | CH3 | CH3 | CH | |
| L-4 | H | (CH2)2CH3 | CH3 | OCH3 | N | |
| L-4 | H | F | CH3 | OCH3 | CH | |
| L-4 | H | Cl | CH3 | CH3 | CH | |
| L-4 | H | Br | CH3 | CH3 | N | |
| L-4 | H | NO2 | CH3 | OCH3 | N | |
| L-4 | H | CO2CH3 | CH3 | CH3 | CH | |
| L-4 | H | CO2CH3 | CH3 | OCH3 | CH | |
| L-4 | H | CO2CH3 | CH3 | CH3 | N | |
| L-4 | H | CO2CH3 | CH3 | OCH3 | N | |
| L-4 | H | CO2CH3 | CH2CH3 | OCH3 | CH | |
| L-4 | CH3 | CO2CH3 | CH3 | OCH3 | CH | |
| L-4 | H | CO2CH2CH3 | CH3 | OCH3 | CH | |
| L-4 | H | CO2CH2CH3 | CH3 | OCH3 | N | |
| L-4 | H | CO2(CH2)3CH3 | CH3 | CH3 | CH | |
| L-4 | H | CO2(CH2)2OCH3 | CH3 | OCH3 | CH | |
| L-4 | H | CO2(CH2)2Cl | CH3 | OCH3 | N | |
| L-4 | H | CO2CH2CH=CH2 | CH3 | CH3 | CH | |
| L-4 | H | SO2N(CH3)2 | CH3 | OCH3 | CH | |
| L-4 | H | SO2N(CH3)2 | CH3 | OCH3 | N | |
| L-4 | H | SO2N(CH3)(CH2)2CH3 | CH3 | CH3 | CH | |
| L-4 | H | SO2N(CH2CH3)2 | CH3 | OCH3 | N | |
| L-4 | H | SO2N(OCH3)CH3 | CH3 | CH3 | N | |
| L-4 | H | SCH3 | CH3 | OCH3 | N | |
| L-4 | H | SCH2CH2CH3 | CH3 | OCH3 | CH | |
| L-4 | H | SCH2CH=CH2 | CH3 | CH3 | CH | |
| L-4 | H | SO2CH3 | CH3 | OCH3 | N | |
| L-4 | H | SO2CH(CH3)2 | CH3 | OCH3 | CH | |
| L-4 | H | SO2CH2CH=CH2 | CH3 | OCH3 | N | |
| L-5 | H | CH3 | CH3 | CH3 | CH | |
| L-5 | H | CH(CH3)2 | CH3 | OCH3 | CH | |
| L-5 | H | F | CH3 | OCH3 | N | |
| L-5 | H | Cl | CH3 | CH3 | CH | |
| L-5 | H | Br | CH3 | CH3 | N | |
| L-5 | H | NO2 | CH3 | OCH3 | N | |
| L-5 | H | CO2CH3 | CH3 | CH3 | CH | |
| L-5 | H | CO2CH3 | CH3 | OCH3 | CH | 182–184 |
| L-5 | H | CO2CH3 | CH3 | CH3 | N | |
| L-5 | H | CO2CH3 | CH3 | OCH3 | N | |
| L-5 | H | CO2CH3 | CH3 | OCH2CH3 | CH | |
| L-5 | H | CO2CH3 | CH3 | OCH2CF3 | N | |
| L-5 | H | CO2CH3 | CH3 | OCF2H | CH | |
| L-5 | H | CO2CH3 | CH3 | CF3 | CH | |
| L-5 | H | CO2CH3 | CH3 | NHCH3 | N | |
| L-5 | H | CO2CH3 | CH3 | N(CH3)2 | CH | |
| L-5 | H | CO2CH3 | CH2CH3 | OCH3 | CH | |
| L-5 | H | CO2CH3 | CH2CH3 | CF3 | N | |
| L-5 | H | CO2CH3 | CHF2 | OCH3 | CH | |
| L-5 | CH3 | CO2CH3 | CH3 | OCH3 | N | |
| L-5 | H | CO2CH2CH3 | CH3 | CH3 | CH | |
| L-5 | H | CO2CH2CH3 | CH3 | OCH3 | CH | |
| L-5 | H | CO2CH2CH3 | CH3 | CH3 | N | |
| L-5 | H | CO2CH2CH3 | CH3 | OCH3 | N | |
| L-5 | H | CO2CH2CH3 | CHF2 | OCH3 | CH | |
| L-5 | H | CO2(CH2)3CH3 | CH3 | OCH3 | N | |
| L-5 | H | CO2(CH2)2OCH3 | CH3 | OCH3 | CH | |
| L-5 | H | CO2(CH2)2Cl | CH3 | CH3 | CH | |
| L-5 | H | CO2CH2CH=CH2 | CH3 | OCH3 | N | |
| L-5 | H | SO2N(CH3)2 | CH3 | OCH3 | CH | |
| L-5 | H | SO2N(CH3)2 | CH3 | OCH3 | N | |
| L-5 | H | SO2N(CH3)(CH2)2CH3 | CH3 | CH3 | CH | |
| L-5 | H | SO2N(CH2CH3)2 | CH3 | OCH3 | N | |
| L-5 | H | SO2N(OCH3)CH3 | CH3 | OCH3 | N | |
| L-5 | H | SCH3 | CH3 | CH3 | CH | |
| L-5 | H | SCH(CH3)2 | CH3 | OCH3 | N | |
| L-5 | H | SCH2CH=CH2 | CH3 | OCH3 | CH | |
| L-5 | H | SO2CH3 | CH3 | CH3 | CH | |
| L-5 | H | SO2(CH2)2CH3 | CH3 | OCH3 | N | |
| L-5 | H | SO2CH2CH=CH2 | CH3 | OCH3 | CH | |
| L-5 | CH3 | SO2N(CH3)2 | CH3 | OCH3 | CH | |
| L-6 | H | CH3 | CH3 | CH3 | N | |
| L-6 | H | (CH2)2CH3 | CH3 | OCH3 | CH | |

TABLE 10-continued

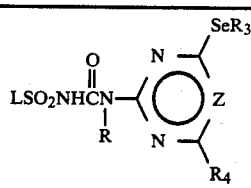

| L | R | R9 | R3 | R4 | Z | m.p. (°C.) |
|---|---|---|---|---|---|---|
| L-6 | H | F | CH3 | OCH3 | N | |
| L-6 | H | Cl | CH3 | CH3 | CH | |
| L-6 | H | Br | CH3 | OCH3 | N | |
| L-6 | H | NO2 | CH3 | OCH3 | CH | |
| L-6 | H | CO2CH3 | CH3 | CH3 | CH | |
| L-6 | H | CO2CH3 | CH3 | OCH3 | CH | |
| L-6 | H | CO2CH3 | CH3 | CH3 | N | |
| L-6 | H | CO2CH3 | CH3 | OCH3 | N | |
| L-6 | H | CO2CH3 | CH3 | OCF2H | CH | |
| L-6 | CH3 | CO2CH3 | CH3 | CH3 | CH | |
| L-6 | H | CO2CH2CH3 | CH3 | OCH3 | CH | |
| L-6 | H | CO2CH2CH3 | CH3 | OCH3 | N | |
| L-6 | H | CO2(CH2)3CH3 | CH3 | OCH3 | CH | |
| L-6 | H | CO2(CH2)2OCH3 | CH3 | CH3 | CH | |
| L-6 | H | CO2(CH2)2Cl | CH3 | OCH3 | N | |
| L-6 | H | CO2CH2CH=CH2 | CH3 | OCH3 | CH | |
| L-6 | H | SO2N(CH3)2 | CH3 | OCH3 | N | |
| L-6 | H | SO2N(CH3)(CH2)2CH3 | CH3 | OCH3 | CH | |
| L-6 | H | SO2N(OCH3)CH3 | CH3 | CH3 | CH | |
| L-6 | H | SCH3 | CH3 | OCH3 | N | |
| L-6 | H | S(CH2)2CH3 | CH3 | OCH3 | CH | |
| L-6 | H | SCH2CH=CH2 | CH3 | OCH3 | N | |
| L-6 | H | SO2CH3 | CH3 | OCH3 | CH | |
| L-6 | H | SO2CH(CH3)2 | CH3 | CH3 | CH | |
| L-6 | H | SO2CH2CH=CH2 | CH3 | OCH3 | N | |

TABLE 11

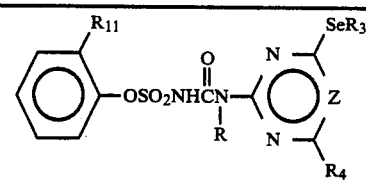

| R | R10 | R3 | R4 | Z | m.p. (°C.) |
|---|---|---|---|---|---|
| H | Cl | CH3 | OCH3 | CH | |
| H | NO2 | CH3 | OCH3 | N | |
| H | CO2CH3 | CH3 | CH3 | CH | |
| H | CO2CH3 | CH3 | OCH3 | CH | |
| H | CO2CH3 | CH3 | CH3 | N | |
| H | CO2CH3 | CH3 | OCH3 | N | |
| H | CO2CH3 | CH3 | OCH2CH3 | CH | |
| H | CO2CH3 | CH3 | OCH2CF3 | N | |
| H | CO2CH3 | CH3 | OCF2H | CH | |
| H | CO2CH3 | CH3 | CF3 | CH | |
| H | CO2CH3 | CH3 | NHCH3 | N | |
| H | CO2CH3 | CH3 | N(CH3)2 | CH | |
| H | CO2CH3 | CH2CH3 | OCH3 | CH | |
| H | CO2CH3 | CH2CH3 | OCH3 | N | |
| H | CO2CH3 | CHF2 | OCH3 | CH | |
| CH3 | CO2CH3 | CH3 | OCH3 | CH | |
| H | CO2CH2CH3 | CH3 | CH3 | CH | |
| H | SO2N(CH3)2 | CH3 | CH3 | N | |
| H | OSO2CH3 | CH3 | OCH3 | N | |
| H | SO2CH3 | CH3 | OCH3 | CH | |
| H | SO2CH2CH3 | CH3 | OCH3 | N | |
| H | OCH3 | CH3 | OCH3 | CH | |
| H | OCH2CH3 | CH3 | OCH3 | N | |

TABLE 12

| R | R11 | R3 | R4 | Z | m.p. (°C.) |
|---|---|---|---|---|---|
| H | Cl | CH3 | CH3 | CH | |
| H | Br | CH3 | OCH3 | N | |
| H | NO2 | CH3 | CH3 | N | |
| H | CH3 | CH3 | OCH3 | N | |
| H | CH2CH3 | CH3 | OCH3 | CH | |
| H | OCH3 | CH3 | CH3 | CH | |
| H | OCH2CH3 | CH3 | OCH3 | N | |
| H | CO2CH3 | CH3 | CH3 | CH | |
| H | CO2CH3 | CH3 | OCH3 | CH | |
| H | CO2CH3 | CH3 | CH3 | N | |
| H | CO2CH3 | CH3 | OCH3 | N | |
| H | CO2CH3 | CH3 | OCH2CH3 | CH | |
| H | CO2CH3 | CH3 | OCH2CF3 | N | |
| H | CO2CH3 | CH3 | OCF2H | CH | |
| H | CO2CH3 | CH3 | CF3 | N | |
| H | CO2CH3 | CH3 | NHCH3 | CH | |
| H | CO2CH3 | CH3 | N(CH3)2 | N | |
| H | CO2CH3 | CH2CH3 | OCH3 | N | |
| H | CO2CH3 | CH2CH3 | OCF2H | CH | |
| H | CO2CH3 | CHF2 | CH3 | CH | |
| CH3 | CO2CH3 | CH3 | OCH3 | N | |
| H | CO2CH2CH3 | CH3 | CH3 | N | |
| H | SO2N(CH3)2 | CH3 | CH3 | CH | |
| H | OSO2CH3 | CH3 | CH3 | N | |
| H | OSO2(CH2)2CH3 | CH3 | OCH3 | CH | |
| H | OSO2N(CH3)2 | CH3 | OCH3 | N | |
| H | SO2CH3 | CH3 | CH3 | CH | |
| H | SO2CH2CH3 | CH3 | OCH3 | N | |

TABLE 13

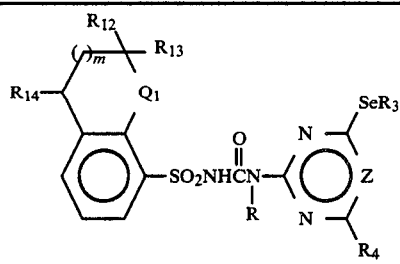

| $Q_1$ | m | R | $R_{12}$ | $R_{13}$ | $R_{14}$ | $R_3$ | $R_4$ | Z | m.p. (°C.) |
|---|---|---|---|---|---|---|---|---|---|
| O | 0 | H | H | H | H | $CH_3$ | $OCH_3$ | CH | |
| O | 0 | H | H | H | H | $CH_3$ | $OCH_3$ | N | |
| O | 0 | H | $CH_3$ | H | H | $CH_3$ | $CH_3$ | CH | |
| O | 0 | H | $CH_2CH_3$ | $CH_3$ | H | $CH_3$ | $CH_3$ | N | |
| O | 0 | H | $CH_2CH_3$ | $CH_2CH_3$ | H | $CH_3$ | $OCH_3$ | CH | |
| O | 0 | H | H | H | $CH_3$ | $CH_3$ | $CH_3$ | CH | |
| O | 1 | H | H | H | H | $CH_3$ | $OCH_3$ | CH | |
| O | 1 | H | H | H | H | $CH_3$ | $OCH_3$ | N | |
| O | 1 | H | $CH_3$ | H | H | $CH_3$ | $OCH_3$ | CH | |
| O | 1 | H | $CH_3$ | $CH_3$ | H | $CH_3$ | $CH_3$ | N | |
| O | 1 | H | $CH_2CH_3$ | $CH_2CH_3$ | H | $CH_3$ | $OCH_3$ | CH | |
| O | 1 | $CH_3$ | H | H | H | $CH_3$ | $OCH_3$ | CH | |
| O | 1 | H | $CH_3$ | H | H | $CH_2CH_3$ | $OCH_2CH_3$ | CH | |
| S | 0 | H | H | H | H | $CH_3$ | $OCH_3$ | CH | |
| S | 0 | H | H | H | H | $CH_3$ | $OCH_3$ | N | |
| S | 0 | H | $CH_3$ | H | H | $CH_3$ | $CH_3$ | CH | |
| S | 0 | H | $CH_3$ | H | H | $CF_2H$ | $OCH_3$ | CH | |
| S | 0 | H | $CH_3$ | $CH_3$ | H | $CH_3$ | $CH_3$ | CH | |
| S | 0 | H | $CH_2CH_3$ | $CH_2CH_3$ | H | $CH_3$ | $OCH_3$ | N | |
| S | 0 | $CH_3$ | H | H | H | $CH_3$ | $OCH_3$ | N | |
| S | 0 | H | $CH_3$ | H | $CH_3$ | $CH_3$ | $OCH_3$ | CH | |
| S | 1 | H | H | H | H | $CH_3$ | $OCH_3$ | CH | |
| S | 1 | H | H | H | H | $CH_3$ | $OCH_3$ | N | |
| S | 1 | H | $CH_3$ | H | H | $CH_3$ | $CH_3$ | N | |
| S | 1 | H | $CH_2CH_3$ | $CH_3$ | H | $CH_3$ | $OCH_3$ | CH | |
| S | 1 | H | $CH_2CH_3$ | $CH_2CH_3$ | H | $CH_3$ | $OCH_3$ | N | |
| S | 1 | $CH_3$ | H | H | H | $CH_3$ | $OCH_3$ | CH | |
| $SO_2$ | 0 | H | H | H | H | $CH_3$ | $CH_3$ | CH | |
| $SO_2$ | 0 | H | H | H | H | $CH_3$ | $OCH_3$ | CH | |
| $SO_2$ | 0 | H | H | H | H | $CH_3$ | $CH_3$ | N | |
| $SO_2$ | 0 | H | H | H | H | $CH_3$ | $OCH_3$ | N | |
| $SO_2$ | 0 | H | H | H | H | $CH_3$ | $OCH_2CH_3$ | CH | |
| $SO_2$ | 0 | H | H | H | H | $CH_3$ | $OCH_2CF_3$ | N | |
| $SO_2$ | 0 | H | H | H | H | $CH_3$ | $OCF_2H$ | CH | |
| $SO_2$ | 0 | H | H | H | H | $CH_3$ | $CF_3$ | CH | |
| $SO_2$ | 0 | H | H | H | H | $CH_3$ | $NHCH_3$ | N | |
| $SO_2$ | 0 | H | H | H | H | $CH_3$ | $N(CH_3)_2$ | CH | |
| $SO_2$ | 0 | H | H | H | H | $CH_2CH_3$ | $CH_3$ | N | |
| $SO_2$ | 0 | H | H | H | H | $CHF_2$ | $OCH_3$ | CH | |
| $SO_2$ | 0 | $CH_3$ | H | H | H | $CH_3$ | $OCH_3$ | N | |
| $SO_2$ | 0 | H | $CH_3$ | H | H | $CH_3$ | $CH_3$ | N | |
| $SO_2$ | 0 | H | $CH_2CH_3$ | $CH_3$ | H | $CH_3$ | $CH_3$ | CH | |
| $SO_2$ | 0 | H | $CH_2CH_3$ | $CH_2CH_3$ | H | $CH_3$ | $OCH_3$ | CH | |
| $SO_2$ | 0 | H | $CH_3$ | H | $CH_3$ | $CH_3$ | $OCH_3$ | N | |
| $SO_2$ | 1 | H | H | H | H | $CH_3$ | $OCH_3$ | CH | |
| $SO_2$ | 1 | H | $CH_3$ | H | H | $CH_3$ | $CH_3$ | N | |
| $SO_2$ | 1 | H | $CH_2CH_3$ | $CH_3$ | H | $CH_3$ | $CH_3$ | CH | |
| $SO_2$ | 1 | H | $CH_2CH_3$ | $CH_2CH_3$ | H | $CH_3$ | $OCH_3$ | CH | |
| $SO_2$ | 1 | $CH_3$ | H | H | H | $CH_3$ | $CH_3$ | CH | |
| $SO_2$ | 1 | H | $CH_3$ | H | H | $CH_2CH_3$ | $OCH_3$ | N | |
| NH | 0 | H | H | H | H | $CH_3$ | $CH_3$ | N | |
| NH | 0 | H | $CH_3$ | H | H | $CH_3$ | $OCH_3$ | CH | |
| NH | 0 | H | $CH_3$ | $CH_3$ | H | $CH_3$ | $CH_3$ | CH | |
| NH | 0 | H | $CH_2CH_3$ | $CH_2CH_3$ | H | $CH_3$ | $OCH_3$ | N | |
| NH | 0 | H | H | H | $CH_3$ | $CH_3$ | $CH_3$ | CH | |
| NH | 0 | $CH_3$ | $CH_3$ | H | H | $CH_3$ | $OCH_3$ | CH | |
| NH | 0 | H | $CH_3$ | $CH_3$ | H | $CHF_2$ | $OCH_3$ | CH | |
| NH | 1 | H | H | H | H | $CH_3$ | $CH_3$ | CH | |
| NH | 1 | H | $CH_3$ | H | H | $CH_3$ | $OCH_3$ | N | |
| NH | 1 | H | $CH_3$ | $CH_3$ | H | $CH_3$ | $OCH_3$ | CH | |
| NH | 1 | H | $CH_2CH_3$ | H | H | $CH_3$ | $CH_3$ | CH | |
| NH | 1 | H | $CH_2CH_3$ | $CH_2CH_3$ | H | $CH_3$ | $OCH_3$ | N | |
| NH | 1 | $CH_3$ | H | H | H | $CH_3$ | $CH_3$ | CH | |
| $NCH_3$ | 0 | H | H | H | H | $CH_3$ | $OCH_3$ | CH | |
| $NCH_3$ | 0 | H | $CH_3$ | H | H | $CH_3$ | $CH_3$ | N | |
| $NCH_3$ | 0 | H | $CH_2CH_3$ | $CH_3$ | H | $CH_3$ | $OCH_3$ | N | |
| $NCH_3$ | 0 | H | $CH_2CH_3$ | $CH_2CH_3$ | H | $CH_3$ | $OCH_3$ | CH | |

TABLE 13-continued

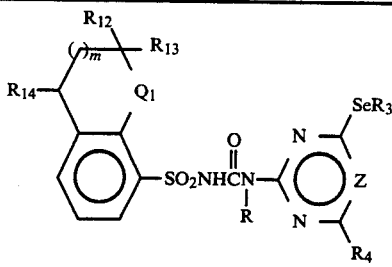

| Q1 | m | R | R12 | R13 | R14 | R3 | R4 | Z | m.p. (°C.) |
|---|---|---|---|---|---|---|---|---|---|
| NCH3 | 0 | H | CH3 | H | CH3 | CH3 | CH3 | CH | |
| NCH3 | 0 | CH3 | H | H | H | CH3 | OCH3 | N | |
| NCH3 | 1 | H | H | H | H | CH3 | CH3 | N | |
| NCH3 | 1 | H | CH3 | H | H | CH3 | OCH3 | CH | |
| NCH3 | 1 | H | CH2CH3 | H | H | CH3 | OCH3 | CH | |
| NCH3 | 1 | H | CH2CH3 | CH2CH3 | H | CH3 | OCH3 | N | |
| NCH3 | 1 | CH3 | CH3 | H | H | CH3 | CH3 | CH | |
| NCH3 | 1 | H | CH3 | H | H | CH2CH3 | OCH2CH3 | CH | |

TABLE 14

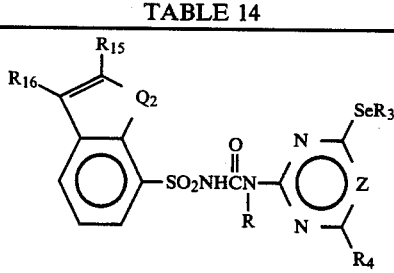

| Q2 | R | R15 | R16 | R3 | R4 | Z | m.p. (°C.) |
|---|---|---|---|---|---|---|---|
| O | H | H | H | CH3 | CH3 | CH | |
| O | H | H | H | CH3 | OCH3 | CH | |
| O | H | H | H | CH3 | CH3 | N | |
| O | H | H | H | CH3 | OCH3 | N | |
| O | H | H | H | CH3 | OCH2CH3 | CH | |
| O | H | H | H | CH3 | OCH2CF3 | N | |
| O | H | H | H | CH3 | OCF2H | CH | |
| O | H | H | H | CH3 | CF3 | CH | |
| O | H | H | H | CH3 | NHCH3 | N | |
| O | H | H | H | CH3 | N(CH3)2 | CH | |
| O | H | H | H | CH2CH3 | OCH3 | N | |
| O | H | H | H | CHF2 | CH3 | CH | |
| O | H | CH3 | H | CH3 | OCH3 | CH | |
| O | H | H | CH3 | CH3 | CH3 | CH | |
| O | H | CH3 | CH3 | CH3 | OCH3 | N | |
| O | CH3 | CH3 | H | CH3 | OCH3 | N | |
| S | H | H | H | CH3 | CH3 | N | |
| S | H | CH3 | H | CH3 | OCH3 | CH | |
| S | H | H | CH3 | CH3 | OCH3 | N | |
| S | H | CH3 | CH3 | CH3 | CH3 | CH | |
| S | CH3 | H | H | CH3 | OCH3 | N | |
| S | H | CH3 | H | CH2CH3 | OCH3 | N | |
| NH | H | H | H | CH3 | CH3 | CH | |
| NH | H | CH3 | H | CH3 | OCH3 | N | |
| NH | H | H | CH3 | CH3 | OCH3 | CH | |
| NH | H | CH3 | CH3 | CH3 | CH3 | N | |
| NH | CH3 | H | H | CH3 | OCH3 | CH | |
| NCH3 | H | H | H | CH3 | OCH3 | N | |
| NCH3 | H | CH3 | H | CH3 | CH3 | N | |
| NCH3 | H | CH3 | CH3 | CH3 | OCH3 | CH | |
| NCH3 | H | H | CH3 | CH3 | OCH3 | N | |
| NCH3 | CH3 | CH3 | H | CH3 | CH3 | CH | |
| NCH3 | H | CH3 | H | CHF2 | OCH2CH3 | CH | |

TABLE 15

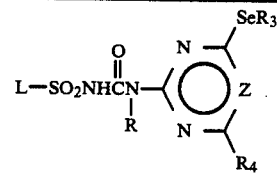

| L | m | R | R14 | R17 | R3 | R4 | Z | m.p. (°C.) |
|---|---|---|---|---|---|---|---|---|
| L-11 | 0 | H | H | CH3 | CH3 | CH3 | CH | |
| L-11 | 0 | H | H | CH3 | CH3 | OCH3 | CH | |
| L-11 | 0 | H | H | CH3 | CH3 | CH3 | N | |
| L-11 | 0 | H | H | CH3 | CH3 | OCH3 | N | |
| L-11 | 0 | H | H | CH3 | CH3 | OCH2CH3 | CH | |
| L-11 | 0 | H | H | CH3 | CH3 | OCH2CF3 | N | |
| L-11 | 0 | H | H | CH3 | CH3 | OCF2H | CH | |
| L-11 | 0 | H | H | CH3 | CH3 | CF3 | CH | |
| L-11 | 0 | H | H | CH3 | CH3 | NHCH3 | N | |
| L-11 | 0 | H | H | CH3 | CH3 | N(CH3)2 | N | |
| L-11 | 0 | H | H | CH3 | CH2CH3 | OCH3 | N | |
| L-11 | 0 | H | H | CH3 | CHF2 | OCH3 | CH | |
| L-11 | 0 | H | CH3 | CH3 | CH3 | OCH3 | N | |
| L-11 | 0 | H | CH2CH3 | CH3 | CH3 | OCH3 | CH | |
| L-11 | 0 | H | CH2CH3 | CH3 | CH3 | CH3 | N | |
| L-11 | 0 | H | CH2CH3 | CH3 | CH3 | OCH3 | CH | |
| L-11 | 0 | H | CH2CH3 | CH3 | CHF2 | OCH2CH3 | CH | |
| L-11 | 0 | CH3 | H | CH3 | CH3 | OCH3 | CH | |
| L-11 | 1 | H | H | CH3 | CH3 | CH3 | CH | |
| L-11 | 1 | H | H | CH3 | CH3 | OCH3 | CH | |
| L-11 | 1 | H | H | CH3 | CH3 | CH3 | N | |
| L-11 | 1 | H | H | CH3 | CH3 | OCH3 | N | |
| L-11 | 1 | H | H | CH3 | CH3 | OCH2CH3 | N | |
| L-11 | 1 | H | H | CH3 | CHF2 | OCH3 | CH | |
| L-11 | 1 | H | H | CH3 | CH2CH3 | CH3 | CH | |
| L-11 | 1 | H | H | CH3 | CH2CH3 | OCH3 | CH | |
| L-11 | 1 | H | H | CH3 | CH2CH3 | CH3 | N | |
| L-11 | 1 | H | H | CH3 | CH2CH3 | OCH3 | N | |
| L-11 | 1 | H | H | CH3 | CH2CH3 | CH2CH3 | OCH3 | N |
| L-11 | 1 | CH3 | H | CH3 | CH3 | OCH3 | N | |
| L-12 | 0 | H | H | — | CH3 | CH3 | CH | |
| L-12 | 0 | H | H | — | CH3 | OCH3 | CH | |
| L-12 | 0 | H | H | — | CH3 | CH3 | N | |
| L-12 | 0 | H | H | — | CH3 | OCH3 | N | |
| L-12 | 0 | H | H | — | CH3 | OCH2CH3 | N | |
| L-12 | 0 | H | H | — | CH3 | OCH2CF3 | CH | |
| L-12 | 0 | H | H | — | CH3 | OCF2H | CH | |
| L-12 | 0 | H | H | — | CH3 | CF3 | N | |
| L-12 | 0 | H | H | — | CH3 | NHCH3 | N | |
| L-12 | 0 | H | H | — | CH3 | N(CH3)2 | CH | |
| L-12 | 0 | H | H | — | CH2CH3 | OCH3 | CH | |
| L-12 | 0 | H | H | — | CHF2 | CH3 | CH | |
| L-12 | 0 | H | CH3 | — | CH3 | OCH3 | CH | |
| L-12 | 0 | H | CH3 | — | CH3 | OCH3 | N | |

TABLE 15-continued

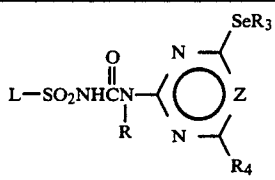

| L | m | R | R14 | R17 | R3 | R4 | Z | m.p. (°C.) |
|---|---|---|---|---|---|---|---|---|
| L-12 | 0 | CH3 | H | — | CH3 | OCH3 | CH | |
| L-12 | 1 | H | H | — | CH3 | CH3 | CH | |
| L-12 | 1 | H | H | — | CH3 | OCH3 | CH | |
| L-12 | 1 | H | H | — | CH3 | CH3 | N | |
| L-12 | 1 | H | H | — | CH3 | OCH3 | N | |
| L-12 | 1 | H | H | — | CH2CH3 | OCH3 | CH | |
| L-12 | 1 | H | H | — | CH3 | OCH2CF3 | N | |
| L-12 | 1 | CH3 | H | — | CH3 | OCH3 | N | |
| L-13 | 0 | H | H | — | CH3 | CH3 | CH | |
| L-13 | 0 | H | H | — | CH3 | OCH3 | CH | |
| L-13 | 0 | H | H | — | CH3 | CH3 | N | |
| L-13 | 0 | H | H | — | CH3 | OCH3 | N | |
| L-13 | 0 | H | H | — | CH3 | OCH2CH3 | N | |
| L-13 | 0 | H | H | — | CH3 | OCF2H | CH | |
| L-13 | 0 | H | H | — | CH2CH3 | OCH3 | N | |
| L-13 | 0 | H | H | — | CHF2 | OCH3 | CH | |
| L-13 | 0 | H | CH3 | — | CH3 | OCH2CH3 | CH | |
| L-13 | 0 | CH3 | H | — | CH3 | OCH3 | CH | |
| L-13 | 1 | H | H | — | CH3 | CH3 | CH | |
| L-13 | 1 | H | H | — | CH3 | OCH3 | CH | |
| L-13 | 1 | H | H | — | CH3 | CH3 | N | |
| L-13 | 1 | H | H | — | CH3 | OCH3 | N | |
| L-13 | 1 | H | H | — | CH3 | OCH2CH3 | CH | |
| L-13 | 1 | H | H | — | CH2CH3 | OCH3 | N | |
| L-13 | 1 | CH3 | H | — | CH3 | OCH3 | N | |
| L-14 | 0 | H | H | — | CH3 | CH3 | CH | |
| L-14 | 0 | H | H | — | CH3 | OCH3 | CH | |
| L-14 | 0 | H | H | — | CH3 | CH3 | N | |
| L-14 | 0 | H | H | — | CH3 | OCH3 | N | |
| L-14 | 0 | H | H | — | CH3 | OCH2CF3 | CH | |
| L-14 | 0 | H | H | — | CHF2 | OCH3 | CH | |
| L-14 | 0 | H | CH3 | — | CH3 | OCH3 | N | |
| L-14 | 0 | CH3 | H | — | CH3 | OCH3 | N | |
| L-14 | 1 | H | H | — | CH3 | CH3 | CH | |
| L-14 | 1 | H | H | — | CH3 | OCH3 | CH | |
| L-14 | 1 | H | H | — | CH3 | CH3 | N | |
| L-14 | 1 | H | H | — | CH3 | OCH3 | N | |
| L-14 | 1 | H | H | — | CH3 | OCH2CH3 | N | |
| L-14 | 1 | H | H | — | CH2CH3 | OCH3 | N | |
| L-14 | 1 | CH3 | H | — | CH3 | OCH3 | CH | |
| L-15 | — | H | — | CH3 | CH3 | CH3 | CH | |
| L-15 | — | H | — | CH3 | CH3 | OCH3 | CH | |
| L-15 | — | H | — | CH3 | CH3 | CH3 | N | |
| L-15 | — | H | — | CH3 | CH3 | OCH3 | N | |
| L-15 | — | H | — | CH3 | CH3 | OCH2CH3 | CH | |
| L-15 | — | H | — | CH3 | CH3 | OCH2CF3 | N | |
| L-15 | — | H | — | CH3 | CH3 | CF3 | N | |
| L-15 | — | H | — | CH3 | CH2CH3 | CH3 | CH | |
| L-15 | — | H | — | CH3 | CHF2 | OCH3 | N | |
| L-15 | — | CH3 | — | CH3 | CH3 | OCH3 | CH | |
| L-15 | — | H | — | CH2CH3 | CH3 | CH3 | CH | |
| L-15 | — | H | — | CH2CH3 | CH3 | OCH3 | CH | |
| L-15 | — | H | — | CH2CH3 | CH3 | CH3 | N | |
| L-15 | — | H | — | CH2CH3 | CH3 | OCH3 | N | |
| L-15 | — | H | — | CH2CH3 | CH2CH3 | CH3 | CH | |
| L-15 | — | H | — | CH2CH3 | CH3 | OCH2CF3 | N | |
| L-15 | — | CH3 | — | CH2CH3 | CH3 | OCH3 | N | |

TABLE 16

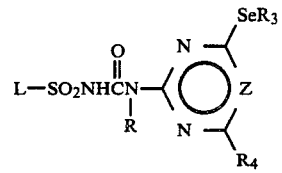

| L | R | R18 | R19 | R3 | R4 | Z | m.p. (°C.) |
|---|---|---|---|---|---|---|---|
| L-16 | H | H | — | CH3 | CH3 | CH | |
| L-16 | H | H | — | CH3 | OCH3 | CH | |
| L-16 | H | H | — | CH3 | CH3 | N | |
| L-16 | H | H | — | CH3 | OCH3 | N | |
| L-16 | H | H | — | CH3 | CF3 | CH | |
| L-16 | H | H | — | CH2CH3 | OCH3 | N | |
| L-16 | H | CH3 | — | CH3 | CH3 | CH | |
| L-16 | H | CH3 | — | CH3 | OCH3 | CH | |
| L-16 | H | CH3 | — | CH3 | CH3 | N | |
| L-16 | H | CH3 | — | CH3 | OCH3 | N | |
| L-16 | H | CH3 | — | CHF2 | OCH3 | CH | |
| L-16 | H | CH3 | — | CH3 | OCH2CF3 | N | |
| L-16 | CH3 | H | — | CH3 | CH3 | CH | |
| L-17 | H | H | — | CH3 | CH3 | CH | |
| L-17 | H | H | — | CH3 | OCH3 | CH | |
| L-17 | H | H | — | CH3 | CH3 | N | |
| L-17 | H | H | — | CH3 | OCH3 | N | |
| L-17 | H | H | — | CH3 | OCH2CH3 | CH | |
| L-17 | H | H | — | CH3 | OCH2CF3 | N | |
| L-17 | H | H | — | CH3 | OCF2H | CH | |
| L-17 | H | H | — | CH3 | CF3 | N | |
| L-17 | H | H | — | CH3 | NHCH3 | CH | |
| L-17 | H | H | — | CH3 | N(CH3)2 | N | |
| L-17 | H | H | — | CH2CH3 | OCH3 | N | |
| L-17 | H | H | — | CHF2 | CH3 | CH | |
| L-17 | H | CH3 | — | CH3 | CH3 | CH | |
| L-17 | H | CH3 | — | CH3 | OCH3 | CH | |
| L-17 | H | CH3 | — | CH3 | CH3 | N | |
| L-17 | H | CH3 | — | CH3 | OCH3 | N | |
| L-17 | H | CH3 | — | CHF2 | OCH3 | CH | |
| L-17 | H | CH3 | — | CH3 | OCH2CH3 | N | |
| L-17 | CH3 | CH3 | — | CH3 | OCH3 | N | |
| L-18 | H | CH3 | H | CH3 | CH3 | CH | |
| L-18 | H | CH3 | H | CH3 | OCH3 | CH | |
| L-18 | H | CH3 | H | CH3 | CH3 | N | |
| L-18 | H | CH3 | H | CH3 | OCH3 | N | |
| L-18 | H | CH3 | H | CH3 | OCH2CH3 | CH | |
| L-18 | H | CH3 | H | CH3 | OCH2CF3 | N | |
| L-18 | H | CH3 | H | CH3 | OCF2H | CH | |
| L-18 | H | CH3 | H | CH3 | CF3 | CH | |
| L-18 | H | CH3 | H | CH3 | NHCH3 | CH | |
| L-18 | H | CH3 | H | CH3 | N(CH3)2 | N | |
| L-18 | H | CH3 | H | CH2CH3 | OCH3 | N | |
| L-18 | H | CH3 | H | CHF2 | OCH3 | CH | |
| L-18 | H | CH3 | CH3 | CH3 | CH3 | CH | |
| L-18 | H | CH3 | CH3 | CH3 | OCH3 | CH | |
| L-18 | H | CH3 | CH3 | CH3 | CH3 | N | |
| L-18 | H | CH3 | CH3 | CH3 | OCH3 | N | |
| L-18 | H | CH3 | CH3 | CH3 | OCH2CH3 | CH | |
| L-18 | H | CH3 | CH3 | CH2CH3 | OCH3 | N | |
| L-18 | CH3 | CH3 | H | CH3 | OCH3 | CH | |
| L-18 | H | H | CH3 | CH3 | OCH2CH3 | N | |
| L-18 | H | H | CH3 | CH3 | N(CH3)2 | CH | |

FORMULATIONS

Useful formulations of the compounds of Formula I and II can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate proportions:

| | Active Ingredient | Percent by Weight | |
|---|---|---|---|
| | | Diluent(s) | Surfactant(s) |
| Wettable Powders | 20–90 | 0–74 | 1–10 |
| Oil Suspensions, Emulsions, Solutions, (including Emulsifiable Concentrates) | 5–50 | 40–95 | 0–15 |
| Aqueous Suspension | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th Ed., McGraw-Hill, New York, 1963, pp. 8–59ff.

For further information regarding the art of formulation, see for example:

J. B. Buchanan, U.S. Pat. No. 3,576,834, Apr. 27, 1971, col. 5, line 36 through col. 7, line 70 and Examples 1–4, 17, 106 and 123–140.

R. R. Shaffer, U.S. Pat. No. 3,560,616, Feb. 2, 1971, col. 3, line 48 through col. 7, line 26 and Examples 3–9 and 11–18.

E. Somers, "Formulation", Chapter 6 in Torgeson, "Fungicides", Vol. I. Academic Press, New York, 1967.

In the following examples, all parts are by weight unless otherwise indicated.

EXAMPLE 7

Wettable Powder

N-[[4-methoxy-6-(methylselenyl)pyrimidin-2-yl]aminocarbonyl]-2-(methylsulfonyl)benzenesulfonamide: 80%
sodium alkylnaphthalenesulfonate: 2%
sodium ligninsulfonate: 2%
synthetic amorphous silica: 3%
kaolinite: 13%

The ingredients are blended and hammer-milled.

EXAMPLE 8

High Strength Concentrate

N-[[[4-methyl-6-(methylselenyl)pyrimidin-2-yl]aminocarbonyl]aminosulfonyl]benzoic acid, methyl ester: 98.5%
silica aerogel: 0.5%
synthetic amorphous silica: 1.0%

The ingredients are blended and ground in a hammer-mill to produce a high strength concentrate essentially all passing a U.S.S. No. 50 sieve (0.3 mm openings). This material may then be formulated in a variety of ways.

EXAMPLE 9

Dust

Wettable Powder of Example 7: 10%
pyrophyllite (powder): 90%

The wettable powder and the pyrophyllite diluent are thoroughly blended and then packaged. The product is suitable for use as a dust.

EXAMPLE 10

Aqueous Suspension

2-[[[4-methoxy-6-(methylselenyl)-1,3,5-triazin-2-yl]aminocarbonyl]aminosulfonyl]benzoic acid, ethyl ester: 25%
hydrated attapulgite: 3%
crude calcium ligninsulfonate: 10%
sodium dihydrogen phosphate: 0.5%
water: 61.5%

The ingredients are ground together in a ball, sand or roller mill until the solid particles have been reduced to diameters under 10 microns.

EXAMPLE 11

Oil Suspension

N-[(4,6-dimethoxypyrimidin-2-yl)aminocarbonyl]-2-(methylselenyl)benzenesulfonamide: 35%
blend of polyalcohol carboxylic esters and oil soluble petroleum sulfonates: 6%
mineral oil: 59%

The ingredients are combined and ground together in a sand mill to produce particles essentially all below 3 microns. The product can be used directly, extended with oils, or emulsified in water.

EXAMPLE 12

Solution

N-[(4-methoxy-6-methyl-1,3,5-triazin-2-yl)aminocarbonyl]-2-(methylselenyl)benzenesulfonamide: 30%
dimethylformamide: 70%

The ingredients are combined and stirred to produce a solution, which can be used for low volume applications.

EXAMPLE 13

Emulsifiable Concentrate

N-[[4-methoxy-6-(methylselenyl)pyrimidin-2-yl]aminocarbonyl]-2-(methylsulfonyl)benzenesulfonamide: 10%
blend of oil soluble sulfonates and polyoxyethylene ethers: 4%
xylene: 86%

The ingredients are combined and stirred with gentle warming to speed solution. A fine screen filter is included in packaging operation to insure the absence of any extraneous undissolved material in the product.

EXAMPLE 14

Granule wettable powder of Example 7: 50%
gypsum: 34%
potassium sulfate: 16%

The ingredients are blended in a rotating or fluid bed mixer and sprayed on to accomplish granulation. When most of the material has reached the desired range of 1.0 to 0.42 mm (U.S.S. #18 to 40 sieves), the granules are removed, dried, and screened. Oversize material is crushed to produce additional material in the desired range. These granules contain 40% active ingredient.

UTILITY

Test results indicate that the compounds of the present invention are active herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, many of the subject compounds should be useful for the selective pre- or post-emergence weed control in crops, especially wheat, cotton and soybeans.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.01 to 5 kg/ha, the lower rates being suggested for use on lighter soils and/or those having a low organic matter content, for selective weed control or for situations where only short-term persistence is required.

The compounds of the invention may be used in combination with any other commercial herbicide; examples of which are those of the triazine, triazole, uracil, urea, amide, diphenylether, carbamate and bipyridylium types. They may also be used in combination with mefluidide.

The herbicidal properties of the subject compounds were discovered in a number of greenhouse tests. The test procedures and results follow.

TEST A

Seeds of crabgrass (Digitaria sp.), barnyard-grass (Echinochloa crusgalli), wild oats (Avena fatua), sicklepod (Cassia obtusifolia), morningglory (Ipomoea sp.), cocklebur (Xanthium sp.), sorghum, corn, soybean, cotton, sugar beet, rice, wheat and purple nutsedge (Cyperus rotundus) tubers were planted and treated pre-emergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/nectosis;
E=emergence inhibition;
G=growth retardation;
H=formative effects; and
U=unusual pigmentation.

COMPOUNDS

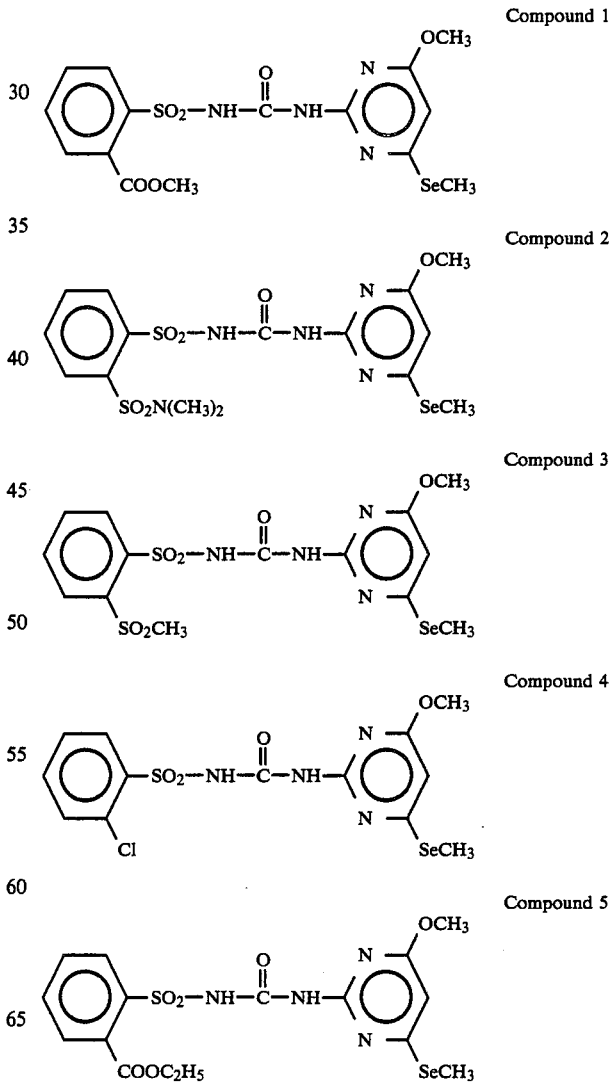

Compound 6
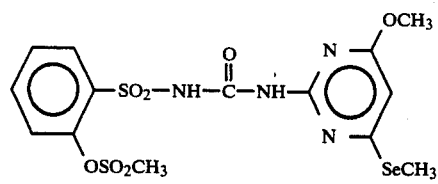
Compound 7
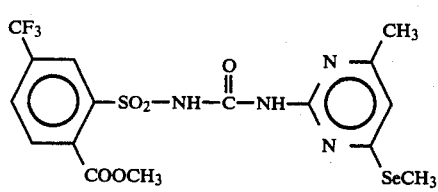
Compound 8
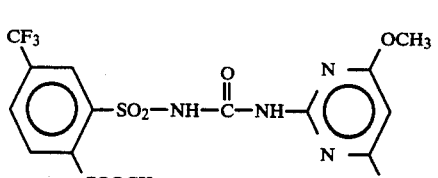
Compound 9
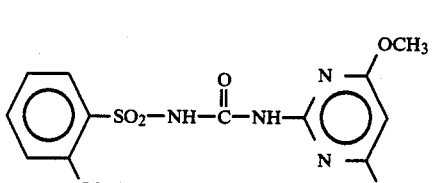
Compound 10
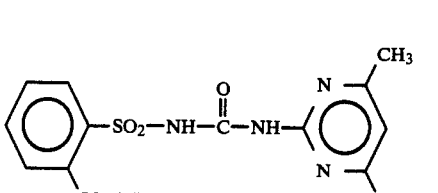
Compound 11
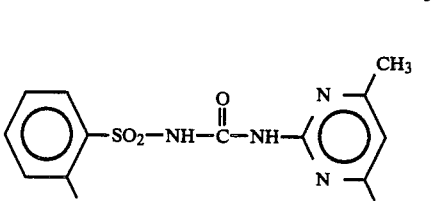
Compound 12
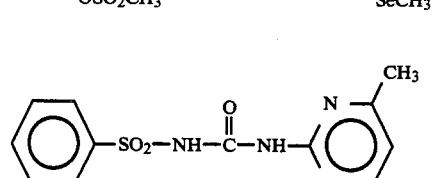
Compound 13
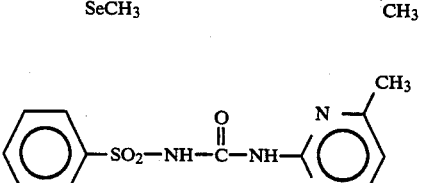
Compound 14
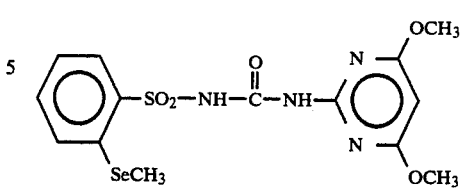
Compound 15
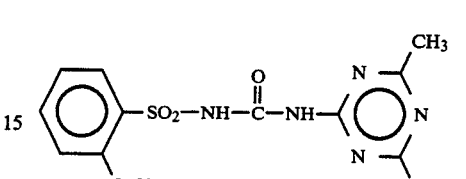
Compound 16
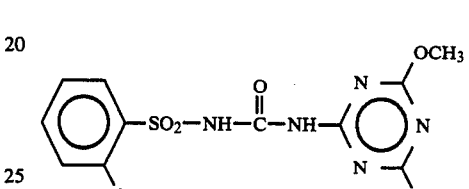
Compound 17
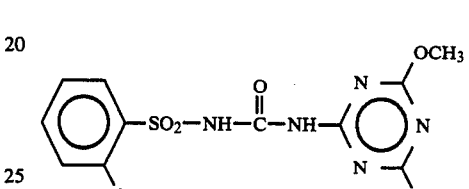
Compound 18
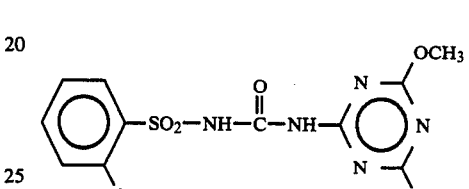
Compound 19
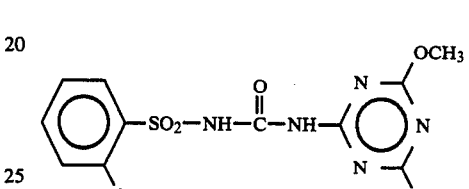
Compound 20
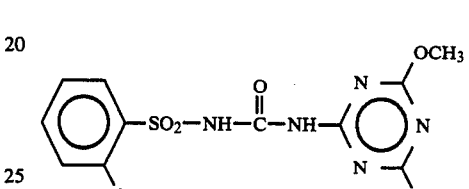
Compound 21
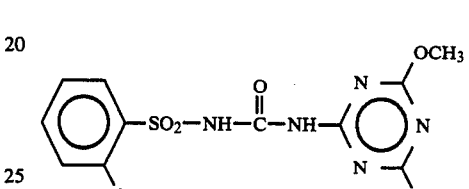

Compound 22
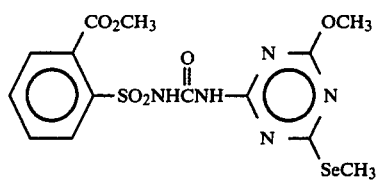
Compound 23
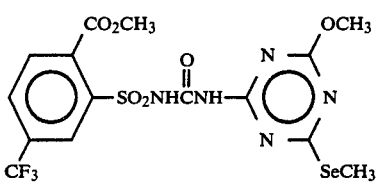
Compound 24
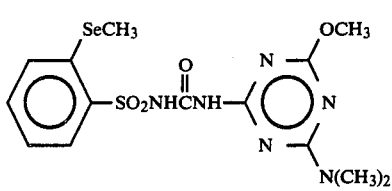
Compound 25
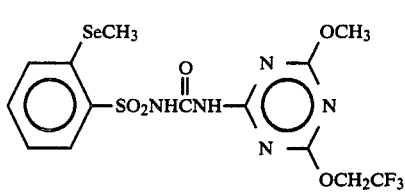
Compound 26
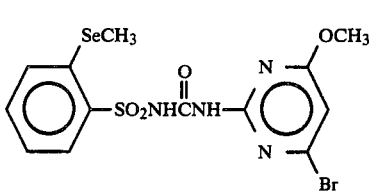
Compound 27
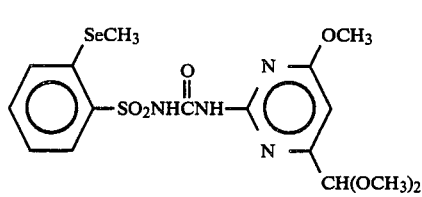
Compound 28
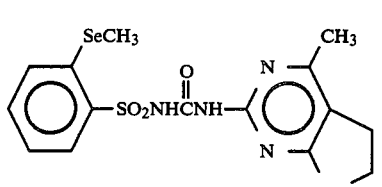
Compound 29
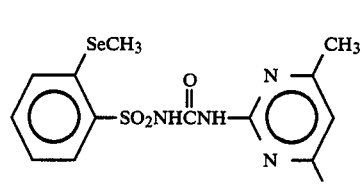
Compound 30
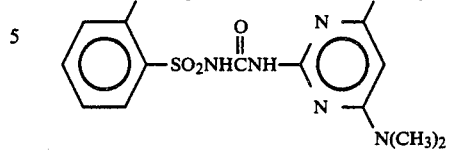
Compound 31
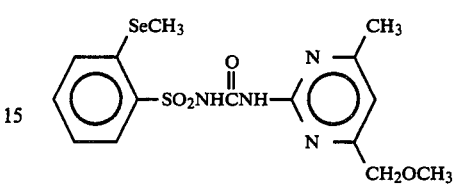
Compound 32
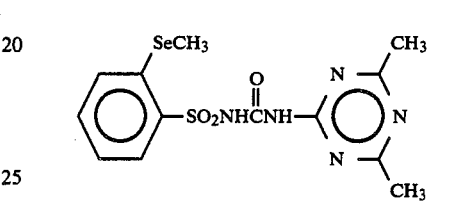
Compound 33
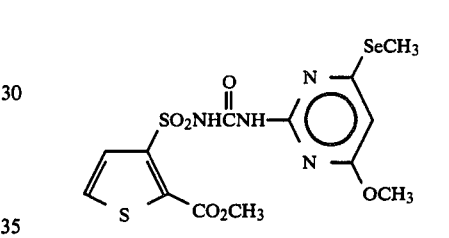
Compound 34
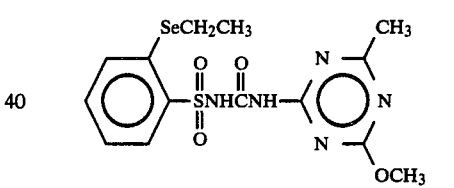
Compound 35
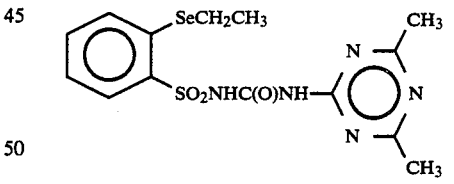
Compound 36
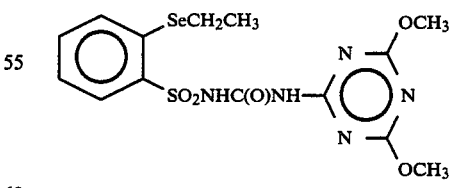
Compound 37
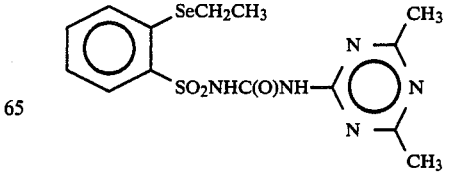

-continued
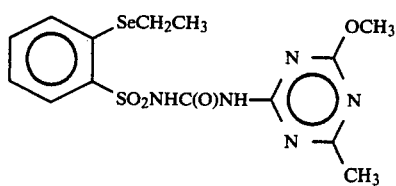
Compound 38
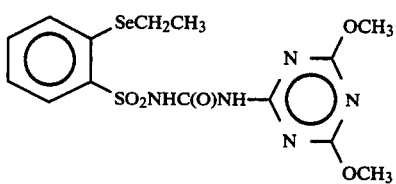
Compound 39
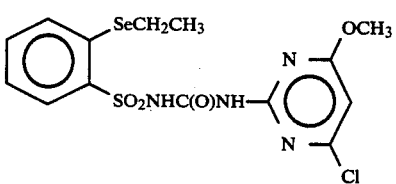
Compound 40
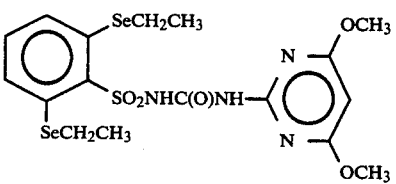
Compound 41
-continued
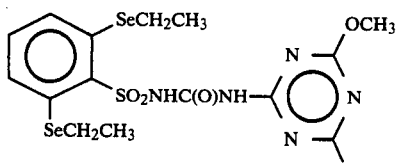
Compound 42
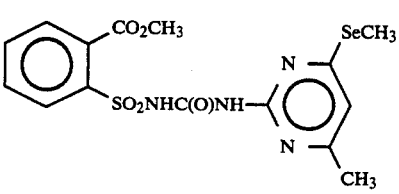
Compound 43
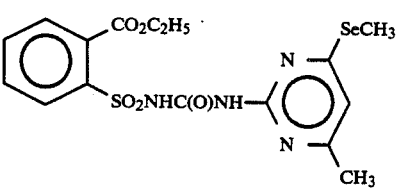
Compound 44
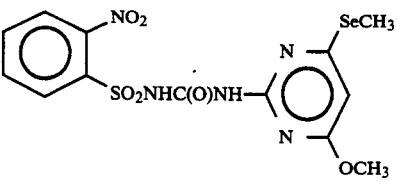
Compound 45

TABLE A

POST-EMERGENCE

| | Cmpd. 1 | Cmpd. 2 | Cmpd. 3 | Compound 4 | | Cmpd. 5 | Cmpd. 6 | Cmpd. 7 | Cmpd. 8 | Compound 9 | | Compound 10 | | Cmpd. 11 | Cmpd. 12 | Cmpd. 13 | Cmpd. 14 | Cmpd. 15 |
|---|---|---|---|---|---|---|---|---|---|---|---|---|---|---|---|---|---|---|
| Rate kg/ha | .05 | .05 | .05 | .4 | .5 | .05 | .05 | .4 | .05 | .4 | .05 | .4 | .05 | .05 | .05 | .05 | .05 | .05 |
| Morningglory | 9C | 2C,8G | 3C,9G | 3C,9H | 3C,8H | 5C,9G | 5C,9G | 3C,8H | 3C,8G | 4C,6G | 2C,3G | 3C,9H | 2C,3H | 1C,2H | 2C,4G | 4C,8G | 1C,2G | 9C |
| Cocklebur | 10C | 5C,9G | 3C,9G | 3C,9G | 2C,5G | 5C,9G | 5C,9G | 4C,9H | 9C | 3C,9G | 5H | 0 | 2G | 2G | 5C,9G | 4C,9H | 9C | 9C |
| Sicklepod | 9C | 6C,9G | 5C,9G | 5C,9G | 2C,4G | 9C | 5C,9G | 3C | 3C,7G | 4C,9G | 2C | 4C,4H | 2C,5G | 2C,5G | 9C | 5C,9G | 9C | 9C |
| Nutsedge | 9C | 3C,6G | 3C,6G | 3C,7G | 2C | 10C | 5G | 2C,5G | 5C,9G | 3C,9G | 0 | 3G | 0 | 0 | 4C,9G | 5G | 9C | 2C,7G |
| Crabgrass | 4C,9G | 2C,7G | 2C,8G | 0 | 0 | 0 | 5G | 2G | 0 | 3G | 3G | 3G | 0 | 0 | 5C,9H | 3G | 5C,9G | 3C,8G |
| Barnyardgrass | 9C | 3C,9H | 3C,9H | 3C,9H | 3C,5G | 3C,5G | 5C,9H | 2C,5H | 0 | 9H | 3H | 8H | 0 | 0 | 5C,9H | 3C,9H | 10C | 5C,9H |
| Wild Oats | 9C | 3C,9G | 5C,9G | 0 | 0 | 0 | 2C,5G | 2C | 0 | 1C | 2G | 2G | 0 | 0 | 3C,9H | 0 | 9C | 3C,9G |
| Wheat | 9C | 9C | 5C,9G | 4G | 2G | 9C | 2G | 2C,6G | 0 | 2G | 0 | 1H | 1C,2H | 0 | 3C,9G | 0 | 3U,9H | 0 |
| Corn | 9C | 4C,9G | 3C,9H | 9H | 7H | 8H | | 4C,8G | 3C,7H | 2G | 2H | 0 | 1C,4G | 1C,4G | 3C,9G | 3U,9G | 5C,9G | 9C |
| Soybean | 5C,9G | 4C,9G | 3C,7H | 2C,5H | 2C | 4C,9G | 8H,9G | 4C,8G | 4C,9G | 2C,7H | 2H | 3G | 3H,5G | 3H,5G | 5C,9G | 5C,9G | 6C,9G | 5C,9G |
| Rice | 9C | 9C | 5C,9G | 7G | 3C,8G | 5C,9G | 4C,9G | 3C,9G | 6G | 2H,7G | 2C,3H | 3G | 1H | 2C,8G | 6C,9G | 2C,8G | 6C,9G | 6C,9G |
| Sorghum | 4U,9G | 2C,9G | 2C,3H | 9C | 5C,9G | 9C | 9C | 2G | 2C,9G | 2C,8G | 3C,9G | 2G | 2G | 9C | 6C,9G | 3C,9H | 3C,9H | 3C,9H |
| Sugar beet | 9C | 9C | 9C | 9C | | 9C | 9C | 3C,8G | 3C,8G | 9C | 2C,2G | 5G | 4C,8G | 9C | 2C,8G | 9C | 9C | 9C |
| Cotton | 9C | 9C | 3C,8H | 5C,9G | 5G | 5C,9G | 9C | 3C,9G | 5G | 4C,9G | 4C,8G | 2G | 4C,9G | 2C,8G | 5C,9G | 5C,9G | 9C | 9C |

POST-EMERGENCE

| | Cmpd. 16 | Cmpd. 17 | Cmpd. 18 | Cmpd. 19 | Cmpd. 20 | | Cmpd. 21 | | Cmpd. 22 | Cmpd. 23 | | Cmpd. 24 | Cmpd. 25 | Cmpd. 26 | Cmpd. 27 | Cmpd. 28 | Cmpd. 29 | Cpd. 30 | Cpd. 31 |
|---|---|---|---|---|---|---|---|---|---|---|---|---|---|---|---|---|---|---|---|
| Rate kg/ha | .05 | .05 | .05 | .05 | .40 | .05 | 2.0 | .05 | .40 | .05 | .05 | .05 | .05 | .05 | .05 | .05 | .05 | .05 | .05 |
| Morningglory | 4C,8H | 5C,9G | 4C,9G | 9C | 2C,3G | 0 | 2B | 3C,8H | 3C,8H | 1C | 0 | 3G | 3C,8G | 4C,8G | 2C,5G | 2C,5H | 1C,3G | 9C | 1C,4H | 1C,2G |
| Cocklebur | 4C,9H | 6C,9G | 9C | 2C,5G | 2C,8G | 0 | 2B | 3C,8H | 3C,8H | 0 | 3G | 9C | 9C | 10C | 5C,9G | 2C,9G | 5C,9G | 9C | 4C,9H | 5G,9H |
| Sicklepod | 9C | 4C,9G | 5C,9G | 5C,9G | 2C,7G | 0 | 2B | 5C,9G | 5C,9G | 26 | 0 | 5C,9G | 5C,9G | 3C,8H | 2C,9G | 2C,9G | 5C,9G | 4C,9G | 4C,5H | 5C,9G |
| Nutsedge | 3C,8G | 9C | 9G | 9G | 5C,9G | 0 | 0 | 9G | 9G | 0 | 0 | 4C,9G | 2C,8G | 3C,7G | 3G | 2C,4G | 0 | 2C,9G | 2G | 8G |
| Crabgrass | 2C,3H | 3C,8G | 4G | 0 | 7G | 0 | 0 | 3C,8H | 3C,8H | 2H | 2H | 4C,9H | 3C,7H | 2C,8G | 5C,9H | 4C,8G | 4C,8G | 3C,7G | 3C,5H | 4C,9H |
| Barnyardgrass | 2C,6G | 9C | 5C,9H | 5C,9G | 2H | 0 | 0 | 1C | 1C | 0 | 0 | 4C,9H | 3C,5G | 9C | 3C,8G,8X | 4C,9H | 5C,9H | 5C,9H | 1C | 5C,9G |
| Wild Oats | 0 | 4C,9G | 0 | 9C | 0 | 0 | 0 | 2C | 2C | 0 | 0 | 9C | 4C,8G | 4C,9G | 3C,6G | 2C,9G | 3C,8G | 3C,8G | 0 | 4C,9G |
| Wheat | 0 | 6G | 3C,9H | 0 | 3G | 0 | 1B,6G | 1C,5H | 1C,5H | 0 | 0 | 4C,9G | 3C,9G | 3C,9G | 5C,9G | 4C,9G | 4C,9G | 3C,9G | 3C,8H | 4C,9G |
| Corn | 4C,9G | 4C,9G | 3C,9H | 1C,1H | 3C,3H | 0 | 2G | 2C,9G | 1C,1H | 3G | 0 | 2C,9G | 5C,9G | 3C,9G | 5C,9G | 2C,9G | 4C,9G | 3C,9G | 3C,9G | 4C,9G |
| Soybean | 5C,9G | 4C,9G | 5C,9G | 2G | 4C,4G | 0 | | 3G | 3C,8G | 2G | 0 | 5C,9G | 5C,9G | 4C,9G | 5C,9G | 6C,9G | 6C,9G | 4C,9G | 2C,8G | 4C,9G |
| Rice | 7G | 5C,9G | 5C,9G | 1C | 3G | 0 | 0 | 2G | 3C,8G | 0 | 0 | 2C,9G | 5C,9H | 5C,9G | 4C,9G | 3C,9H | 3C,9H | 3C,9H | 3C,7G | 3C,9H |
| Sorghum | 2C,5G | 9H | 9C | 2C,5G | 5C,8G | 0 | 2B,9C | 5G | 4G | 0 | 0 | 4C,9G | 2C,9G | 4C,8G | 4C,8G | 9C | 3C,7H | 3C,9H | 4C,9G | 5C,9G |
| Sugar beet | 9C | 9C | 5C,9G | 9C | 9C | 0 | 1B | 2C,6G | 9C | 0 | 0 | 9C | 9C | 9C | 4C,9G | 9C | 9C | 9C | 9C | 9C |
| Cotton | 9C | 9C | 9H | 3C,8H | 2C,8G | 0 | | 9C | | 0 | 0 | 4C,9G | | 5C,9G | 9C | | 5C,9G | 10C | 4C,9G | 5C,9G |

POST-EMERGENCE

| | Cpd. 32 | Cpd. 33 | Cpd. 34 | Cmpd. 35 | Cmpd. 36 | Cmpd. 37 | Cmpd. 38 | Cmpd. 39 | Cmpd. 40 | Cmpd. 41 | Cmpd. 42 | Cmpd. 43 | Cmpd. 44 | Cmpd. 45 |
|---|---|---|---|---|---|---|---|---|---|---|---|---|---|---|
| Rate kg/ha | .05 | .05 | .05 | .05 | .05 | .05 | .05 | .05 | .05 | .05 | .05 | .05 | .05 | .05 |
| Morningglory | 4C,8G | 2C,7G | 9C | 4C,8H | 9C | 9C | 9C | 9C | 10C | 10C | 3C,9G | 1C | 2C,3G | 5C,9G |
| Cocklebur | 10C | 2C,4G | 9C | 9C | 9C | 5C,9G | 9C | 9C | 9C | 9C | 9C | 2G | 3C,8H | 9C |
| Velvetleaf | | | | | | | | — | — | — | — | — | | |
| Sicklepod | 9C | 1C | 9C | 9C | 9C | 9C | 9C | — | — | 9C | 9C | 0 | 2C | 5C,9G |
| Nutsedge | 2C,5G | 0 | 5G | 2C,8G | 2C,5G | 5C,9G | 5G | 5C,9G | 9G | 5C,9G | 0 | 3C,8G | 2C,8G | 5C,9G |
| Crabgrass | 5C,9G | 0 | 2C,6G | 4C,9H | 3C,9G | 2C,5G | 6G | 9G | 2C,8G | 5C,9H | 9C | 2G | 0 | 4G |
| Barnyardgrass | 9C | 0 | 2C,8H | 5C,9H | 5C,9G | 9G | 2C,8H | 2C,8H | 5C,9H | 5C,9H | 2C,9H | 2C,5H | 3H | 3C,8H |
| Cheatgrass | | | | | | | | — | — | — | | — | | |
| Wild Oats | 5C,9G | 2C,8G | 2C,8G | 4C,9G | 4C,9G | 2C,9G | 2C,9G | 0 | 2C,8G | 4C,9H | 2C,7G | 0 | 0 | 2C,7G |
| Wheat | 10C | 0 | 0 | 5C,9G | 2C,9G | 0 | 0 | 9H | | 3C,8G | 3G | 0 | 0 | 2G |
| Corn | 9C | 2G | 3C,9G | 3C,9H | 2C,9G | 2C,9G | 4C,9G | 4C,8G | 9H | 3C,9G | 4C,9G | 1U,4G | 1U,4G | 9C |
| Soybean | 9C | 1H | 4C,9G | 5C,9G | 3C,8G | 3C,8G | 2C,6G | 4C,8G | 5C,9G | 6C,9G | 5C,9G | 5H | 2H | 3C,9G |
| Rice | 6C,9G | 2G | 3C,8G | 6C,9G | 6C,9G | 4C,9G | 4C,9G | 5C,9G | 5C,9G | 6C,9G | 4G | 4G | 4G | 5C,9G |

TABLE A-continued

PRE-EMERGENCE

| | Cmpd. 1 | Cmpd. 2 | Cmpd. 3 | Compound 4 | | Cmpd. 5 | Cmpd. 6 | Cmpd. 7 | | Cmpd. 8 | Compound 9 | | Compound 10 | Cmpd. 11 | Cmpd. 12 | Cmpd. 13 | Cmpd. 14 | Cmpd. 15 |
|---|---|---|---|---|---|---|---|---|---|---|---|---|---|---|---|---|---|---|
| Rate kg/ha | .05 | .05 | .05 | 0.4 | 0.5 | .05 | .05 | 0.4 | .05 | .05 | 0.4 | .05 | 0.4 | .05 | .05 | .05 | .05 | .05 |
| Morningglory | 9C | 9G | 9G | 9G | 8G | 9H | 9C | 4G | 2C | 8G | 8G | 1C | 8G | 3C,5G | 4G | 9G | 8H | 4C,9G |
| Cocklebur | 9H | 9H | 9H | 9H | 1H | — | 9H | 9H | — | 9H | 9H | 2H | 7G | 9H | 8H | 9H | 3C,9H | 9H |
| Sicklepod | 9G | 8G | 8G | 8G | 0 | 3C,9G | 9C | 3G | 0 | 0 | 3C,4G | 0 | 4G | 5C,9G | 3C | 5C,9G | 6C,9G | 9C |
| Nutsedge | 10E | 5G | 7G | 2G | 0 | 10E | 4G | 2G | 0 | 0 | 0 | 1C | 0 | 10E | 5G | 3G | 3C,8G | 3G |
| Crabgrass | 3C,8G | 0 | 0 | 1C | 0 | 2C | 0 | 0 | 0 | 0 | 0 | 0 | 2G | 6C,9G | 3C,8G | 2C,5G | 5C,9G | 4C,8G |
| Barnyardgrass | 5C,9H | 3C,8H | 8H | 2H | 0 | 3C,8H | 4H | 2H | 0 | 4C,5G | 3C,5G | 2C | 7H | 6C,8H | 3C,7H | 4C,8H | 5C,9H | 4C,6H |
| Wild Oats | 4C,9G | 2C,8G | 2C,7G | 2C,7G | 0 | 3C,9G | 2C,8H | 3G | 0 | 0 | 2C,4G | 0 | 6G | 5C,8H | 4C,8G | 5C,8H | 6C,9G | 4C,9G |
| Wheat | 9C | 2C,9G | 9G | 9G | 0 | 9G | 0 | 3G | 0 | 0 | 2G | 0 | 6G | 9H | 5C,9H | 10E | 9H | 0 |
| Corn | 2U,9G | 3C,9G | 2C,9G | 2C,9G | 2C,7G | 9G | 2C,8G | 2C,6G | 3G | 2C,4G | 2C,9H | 5G | 2C,7G | 10E | 10E | 7C,9H | 3C,9H | 4C,9H |
| Soybean | 2C,8H | 6H | 0 | 2C,3H | 0 | 1H | 2C,5H | 1C | 0 | 1H | 2C,2H | 1C,5G | 2C,2H | 9H | 9H | 9H | 3C,9H | 9H |
| Rice | 10E | 2C,8G | 10E | 9G | 5G | 10E | 9H | 6G | 0 | 3C,5G | 1H | 1C,6G | 3C,9H | 10E | 10E | 10E | 5C,9H | 10E |
| Sorghum | 6C,9H | 3C,9H | 3C,9H | 2C,8G | 0 | 5C,9H | 3C,9G | 2C,6G | 0 | 3C,8H | 3C,3G | 2C | 3C,9H | 10H | 7C,9H | 5C,9H | 9C | 4C,9H |
| Sugar beet | 6C,9G | 10E | 9G | 5C,9G | 8G | 5C,9G | 10E | 8G | 2G | 7G | 2C,9G | 5G | 3C,7G | 6C,9G | 4C,9G | 5C,9G | 10E | 10E |
| Cotton | 9G | 8G | 5G | 8G | 2G | 8G | 9G | 5G | 0 | 0 | 5G | 6G | 7G | 3C,9G | 9G | 5C,9G | 3C,9G | 3C,9G |

PRE-EMERGENCE

| | Cmpd. 16 | Cmpd. 17 | Cmpd. 18 | Cmpd. 19 | Cmpd. 20 | | Cmpd. 21 | | Cmpd. 22 | Cmpd. 23 | Cmpd. 24 | Cmpd. 25 | Cmpd. 26 | Cmpd. 27 | Cmpd. 28 | Cmpd. 29 | Cpd. 30 | Cpd. 31 |
|---|---|---|---|---|---|---|---|---|---|---|---|---|---|---|---|---|---|---|
| Rate kg/ha | .05 | .05 | .05 | .40 | .05 | 2.0 | .05 | 0 | .40 | .05 | .05 | .05 | .05 | .05 | .05 | .05 | .05 | .05 |
| Morningglory | 4C,9G | 9G | 8G | 2C,4G | 2C,5G | 0 | 5G | 0 | 5G | 0 | 8H | 3C,5G | 9G | 9G | 5G | 4G | 0 | 2C | 3G |
| Cocklebur | 5C,9H | 8H | 8H | 8H | 7G | — | — | 0 | — | 0 | 5G | 4C,4G | 9H | 9H | — | 8H | 8H | 9H | — |
| Sicklepod | 9C | 2C,8G | 4G | 2C,8G | 5G | 5G | 5G | 0 | 5G | 0 | 3C,5G | 2C,7G | 5G | 5G | 9G | 3C | 3C | 3C | 4C,5G |
| Nutsedge | 0 | 2C,8G | 8G | 4G | 10E | 0 | 10E | 0 | 10E | 3G | 0 | 0 | 5G | 2C | 2C | 5G | 9G | 0 | 7G |
| Crabgrass | 2C,3G | 2C,5G | 2G | 0 | 0 | 0 | 0 | 0 | 0 | 7H | 3C,8G | 1H | 2C,5G | 4C,6G | 3C,5G | 3C,8G | 2C,5G | 3C,8G | 3C,8G |
| Barnyardgrass | 3C | 4C,7H | 4G | 0 | 2C | 0 | 2C | 0 | 2C | .4G | 3C,8H | 1C | 2C,7H | 4C,8H | 3C,7H | 3C,8H | 2C | 2C,7H | 3C,7G |
| Wild Oats | 0 | 3C,8G | 2G | 1C | 0 | 0 | 0 | 0 | 0 | 2G | 3C,9G | 1C | 5C,8G | 3C,7G | 4C,8G | 4C,8G | 3C,9G | 2C,7G | 3C,8H |
| Wheat | 4C,8G | 3C,8G | 2G | 0 | 0 | 0 | 0 | 0 | 0 | 2C | 3C,9G | 2C,9H | 4C,8H | 2C,7G | 2C,7G | 5C,9H | 3U,9H | 2C,8G | 3C,9H |
| Corn | 9H | 2U,9G | 3C,8G | 7G | 5G | 3G | 2G | 0 | 7G | 3G | 4C,9G | 3C,3H | 4C,8H | 5C,9H | 5C,9H | 4C,4H | 1C,2H | 5C,9H | 5C,9H |
| Soybean | 9H | 3C,8H | 1H | 2C,3G | 0 | 0 | 2C,5G | 0 | 5H | 1C | 3G | 2C,9H | 2C,3G | 1C | 1C | 10E | 10E | 3C,9H | 4C,7H |
| Rice | 10E | 10E | 3C,8H | 4G | 3G | 2G | 3C,5G | 0 | 3C,9H | 0 | 10E | 3C,8H | 10E | 2C,7G | 2C,7G | 10E | 10E | 7C,9H | 10E |
| Sorghum | 6C,9H | 5C,9H | 3C,9H | 3C,7G | 2G | 2G | 2C,5G | 0 | 2C,6G | 1C | 4C,9G | 3C,9H | 9C,9H | 8C,9H | 9C,9H | 4C,4H | 1C,2H | 7C,9H | 6C,9H |
| Sugar beet | 10E | 10E | 9G | 9G | 8G | 8G | 8G | 3G | 8G | 4G | 4C,9G | 5C,9H | 5C,9G | 4C,7G | 4C,9G | 4C,9G | 8G | 5C,9H | 5C,8G |
| Cotton | 3C,9G | 8G | 8G | 8G | 6G | 6G | 8G | 0 | 9G | 5G | 8G | 7G | 9G | 6G | 9G | 9G | 8G | 7G | 8G |

PRE-EMERGENCE

| | Cpd. 32 | Cpd. 33 | Cpd. 34 | Cmpd. 35 | Cmpd. 36 | Cpd. 37 | Cmpd. 38 | Cmpd. 39 | Cmpd. 40 | Cmpd. 41 | Cmpd. 42 | Cmpd. 43 | Cmpd. 44 | Cmpd. 45 |
|---|---|---|---|---|---|---|---|---|---|---|---|---|---|---|
| Rate kg/ha | .05 | .05 | .05 | .05 | .05 | .05 | .05 | .05 | .05 | .05 | .05 | .05 | .05 | .05 |
| Morningglory | 7G | 7G | 9G | 9G | 9G | 7G | 9G | 9G | 9G | 9G | 2G | 2G | 0 | 9G |
| Cocklebur | 8H | 5G | 9H | 9H | 9H | 5G | 9H | 9H | 9H | 4G | 3C,9G | — | 1H | 9H |
| Velvetleaf | — | — | — | — | — | — | — | — | — | — | — | — | — | — |
| Sicklepod | 4C,9G | 5G | 10C | 10E | 10E | 10C | 10C | 10E | 3C,3G | 3C,3G | 2G | 3C,5G | 1C | 2C,8G |
| Nutsedge | 2C,5G | 0 | 2C | 3C,9G | 3C,9G | 2C | 2C | 10E | 4G | 4G | 3C | 3G | 3G | 3C,8G |
| Crabgrass | 4C,9G | 0 | 2C,8G | 4C,9H | 3C,9H | 3C,9G | 2C,8G | 5C,9G | 5C,9G | 5G | 0 | 0 | 0 | 2G |
| Barnyardgrass | 4C,8H | 1C | 5G | — | — | 5G | 5G | 9G | 9G | 3C,7G | 2C | 2C | 1C | 4C,5G |
| Cheatgrass | | | | | | | | | | | | | | |

TABLE A-continued

| | | | | | | | | | | | | | |
|---|---|---|---|---|---|---|---|---|---|---|---|---|---|
| Wild Oats | 4C,8H | 0 | 2C,6G | 5C,9H | 2C,8G | 3C,8H | 2C,6G | 4G | 3C,8G | 2C | 3G | 0 | 0 | 2C,8G |
| Wheat | 5C,9H | 0 | 2G | 5C,9H | 3C,9H | 2C,8G | 2G | 0 | 8G | 7H | 2G | 3G | 2G | 7G |
| Corn | 6C,9H | 4G | 2C,8G | 9H | 8G | 3C,9H | 2C,8G | 5G | 8G | 2C,8G | 7G | 2C,8H | 6G | 2C,9G |
| Soybean | 8H | 0 | 10E | 9H | 9H | 8H | 10E | 7G | 9H | 3C,7G | 3C,7G | 2C,3H | 1H | 2H |
| Rice | 10E | 6G | 9H | 10E | 10E | 10E | 9H | 9H | 10E | 5C,9H | 2G | 4C,8H | 5G | 10E |
| Sorghum | 7C,9H | 2C,7G | 2C,8G | 2C,9H | 2C,9G | 5C,9H | 2C,8G | 5G | 5C,9H | 4C,8G | 2G | 6G | 4G | 2C,8G |
| Sugar beet | 4C,8H | 4C,9G | 5C,9G | 5C,9G | 3C,9G | 5C,9G | 5C,9G | 9C | 5C,9G | 5C,9G | 4C,8G | 2C,7G | 2C,6G | 9C |
| Cotton | 8G | 7G | 9G | 9G | 2C,9G | 3C,9G | 9G | 9G | 10E | 8G | 2C,7G | 8G | 7G | 9G |
| Bushbean | — | — | — | — | — | — | — | — | — | — | — | — | — | — |

TEST B
Post-emergence

Two round pans (25 cm diameter by 12.5 cm deep) were filled with Woodstown sandy loam soil. One pan was planted with blackgrass (*Alopecurus myosuroides*), sugarbeets, nutsedge (*Cyperus rotundus*) tubers, crabgrass (*Digitaria sanguinalis*), sicklepod (*Cassia obtusifolia*), teaweed (*Sida spinosa*), jimsonweed (*Datura stramonium*), velvetleaf (*Abutilon theophrasti*), and giant foxtail (*Setaria faberii*). The other pan was planted with two pans were sprayed pre-emergence with the chemicals dissolved in a non-phytotoxic solvent.

Treated plants and controls were maintained in the greenhouse for 28 days, then all treated plants were compared to controls and visually rated for plant response utilizing the rating system as described for Test A.

Response ratings are contained in Table B. The data show the potential utility of several of the compounds tested for selective weed control in crops such as wheat, soybeans and cotton.

TABLE B

|  | Compound 1 | | | | Compound 2 | | | | Compound 3 | | | | Compound 5 | | | |
|---|---|---|---|---|---|---|---|---|---|---|---|---|---|---|---|---|
| Post-Emergence | | | | | | | | | | | | | | | | |
| Rate g/ha | 62 | 16 | 4 | 1 | 62 | 16 | 4 | 1 | 250 | 62 | 16 | 4 | 62 | 16 | 4 | 1 |
| Corn | 10C | 10C | 9G | 3G | 10G | 9G | 6G | 3G | 10C | 10C | 9G | 4G | 10C | 10G | 8G | 5G |
| Wheat | 3G | 2G | 0 | 0 | 7G | 3G | 0 | 0 | 5G | 0 | 0 | 0 | 0 | 0 | 0 | 0 |
| Rice | 10G | 10G | 9G | 2G | 8G | 3G | 0 | 0 | 10G | 10G | 8G | 0 | 9G | 3G | 0 | 0 |
| Soybeans | 10G | 9G | 7G | 3G | 8G | 8G | 3G | 0 | 10G | 9G | 7G | 3G | 9G | 5G | 2G | 0 |
| Cotton | 10G | 9G | 5G | 2G | 9G | 3G | 0 | 0 | 9G | 4G | 0 | 0 | 10G | 7G | 2G | 0 |
| Sugar beets | 10C | 10G | 8G | 3G | 10C | 9G | 6G | 2G | 10C | 10G | 8G | 5G | 10C | 7G | 3G | 0 |
| Crabgrass | 6G | 3G | 0 | 0 | 3G | 0 | 0 | 0 | 9G | 7G | 5G | 0 | 5G | 3G | 0 | 0 |
| Johnsongrass | 10C | 10C | 9G | 2G | 6G | 3G | 0 | 0 | 10C | 10C | 4G | 2G | 10G | 6G | 3G | 0 |
| Blackgrass | 9G | 7G | 4G | 2G | 6G | 0 | 0 | 0 | 10C | 6G | 0 | 0 | 10G | 9G | 4G | 0 |
| Barnyardgrass | 10C | 9G | 5G | 2G | 6G | 2G | 0 | 0 | 10C | 10C | 6G | 0 | 10G | 3G | 0 | 0 |
| Nutsedge | 9C | 9C | 4G | 0 | 6C | 4G | 3G | 0 | 8C | 3G | 0 | 0 | 10C | 9C | 8C | 5C |
| Giant foxtail | 9G | 8G | 4G | 2G | 5G | 3G | 0 | 0 | 10C | 9G | 3G | 0 | 2G | 0 | 0 | 0 |
| Wild Oats | 8G | 4G | 0 | 0 | 4G | 0 | 0 | 0 | 9C | 4G | 0 | 0 | 4G | 0 | 0 | 0 |
| Cocklebur | 10G | 10G | 6G | 3G | 10G | 9G | 8G | 4G | 10G | 9G | 8G | 3G | 10G | 10G | 4G | 0 |
| Morningglory | 10G | 10C | 9G | 3G | 9G | 8G | 3G | 0 | 10G | 6G | 4G | 2G | 10G | 9G | 3G | 0 |
| Teaweed | 5G | 3G | 0 | 0 | 4G | 2G | 0 | 0 | 3G | 0 | 0 | 0 | 5G | 4G | 0 | 0 |
| Sicklepod | 6G | 3G | 2G | 0 | 4G | 3G | 0 | 0 | 7G | 5G | 3G | 0 | 10G | 9G | 6G | 3G |
| Jimsonweed | 10C | 10G | 7G | 5G | 10G | 10G | 9G | 3G | 10C | 10G | 8G | 4G | 10G | 10G | 7G | 3G |
| Velvetleaf | 10G | 5G | 2G | 0 | 10G | 9G | 8G | 2G | 10G | 6G | 0 | 0 | 9G | 6G | 3G | 0 |
| Pre-Emergence | | | | | | | | | | | | | | | | |
| Rate g/ha | 250 | 62 | 16 | 4 | 250 | 62 | 16 | | 250 | 62 | 16 | 4 | 250 | 62 | 16 | 4 |
| Corn | 7G | 2G | 0 | 0 | 10E | 3G | 0 | | 9G | 3G | 0 | 0 | 10E | 10G | 9G | 2G |
| Wheat | 7G | 2G | 0 | 0 | 9G | 7G | 2G | | 5G | 0 | 0 | 0 | 5G | 2G | 0 | 0 |
| Rice | 10E | 9G | 9G | 4G | 10E | 10E | 6G | | 10E | 10E | 9G | 5G | 10E | 10E | 9G | 4G |
| Soybeans | 6G | 2G | 0 | 0 | 6G | 2G | 0 | | 2G | 0 | 0 | 0 | 6G | 2G | 0 | 0 |
| Cotton | 4G | 0 | 0 | 0 | 2G | 0 | 0 | | 0 | 0 | 0 | 0 | 6G | 2G | 0 | 0 |
| Sugar beets | 10G | 4G | 0 | 0 | 10G | 8G | 4G | | 4G | 2G | 0 | 0 | 10G | 10G | 5G | 0 |
| Crabgrass | 9G | 6G | 3G | 0 | 10G | 7G | 3G | | 10G | 9G | 5G | 0 | 8G | 7G | 2G | 0 |
| Johnsongrass | 10C | 7G | 6G | 3G | 10G | 10G | 5G | | 9G | 5G | 2G | 0 | 10G | 9G | 6G | 2G |
| Blackgrass | 9G | 5G | 3G | 0 | 10E | 9G | 6G | | 10E | 8G | 2G | 0 | 10E | 10G | 4G | 0 |
| Barnyardgrass | 10G | 6G | 3G | 0 | 10G | 10G | 4G | | 10E | 9G | 3G | 0 | 10G | 9G | 8G | 2G |
| Nutsedge | 9G | 4G | 0 | 0 | 5G | 3G | 0 | | 6G | 3G | 0 | 0 | 9G | 9G | 4G | 0 |
| Giant foxtail | 10G | 3G | 0 | 0 | 10E | 10G | 5G | | 10E | 6G | 0 | 0 | 10E | 10E | 5G | 0 |
| Wild Oats | 7G | 2G | 0 | 0 | 9G | 7G | 3G | | 6G | 0 | 0 | 0 | 7G | 4G | 0 | 0 |
| Cocklebur | 9G | 6G | 3G | 0 | 8G | 6G | 0 | | 3G | 0 | 0 | 0 | 10G | 9G | 5G | 0 |
| Morningglory | 8G | 5G | 2G | 0 | 2G | 0 | 0 | | 0 | 0 | 0 | 0 | 10G | 3G | 2G | 0 |
| Teaweed | 9G | 5G | 2G | 0 | 7G | 4G | 0 | | 7G | 4G | 0 | 0 | 9G | 7G | 3G | 0 |
| Sicklepod | 6G | 4G | 2G | 0 | 9G | 3G | 0 | | 5G | — | 0 | 0 | 10G | 6G | 3G | 0 |
| Jimsonweed | 10G | 9G | 8G | 2G | 8G | 3G | 0 | | 9G | 3G | 0 | 0 | 10G | 10G | 3G | 0 |
| Velvetleaf | 7G | 2G | 0 | 0 | 4G | 3G | 0 | | 4G | 0 | 0 | 0 | 9G | 7G | 2G | 0 | wheat, cotton, rice, corn, soybean, wild oats (*Avena fatua*), cocklebur (*Xanthium pensylvanicum*), morningglory (*Ipomoea hederacea*), johnsongrass (*Sorghum halepense*) and barnyardgrass (*Echinochloa crusgalli*). The plants were grown for approximately fourteen days, then sprayed post-emergence with the chemicals dissolved in a non-phytotoxic solvent.

Post-emergence

Two round pans (25 cm diameter by 12.5 cm deep) were filled with Woodstown sandy loam soil. One pan was planted with blackgrass, sugarbeets, nutsedge, crabgrass, sicklepod, teaweed, jimsonweed, velvetleaf and giant foxtail. The other pan with planted with wheat, cotton, rice, corn, soybean, wild oats, cocklebur, morningglory, johnsongrass and barnyardgrass. The

What is claimed is:
1. A compound having the formula:

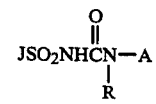

wherein
R is H or CH$_3$;
J is

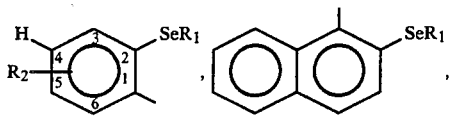

J-1 , J-2 ,

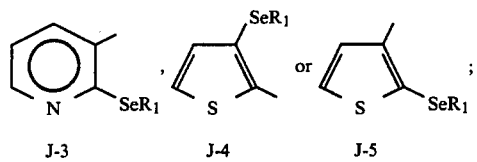

J-3 , J-4 or J-5 ;

$R_1$ is $C_1$-$C_4$ alkyl, $C_3$-$C_4$ alkenyl, $C_3$-$C_4$ alkynyl, $CF_2H$ or $CH_2CH_2OCH_3$;

$R_2$ is H, $C_1$-$C_3$ alkyl, $C_1$-$C_3$ haloalkl, halogen, nitro, $SeR_1$, $C_1$-$C_3$ alkoxy, $SO_2NR^IR^{II}$, $C_1$-$C_3$ alkylthio, $C_1$-$C_3$ alkylsulfinyl, $C_1$-$C_3$ alkylsulfonyl or $CO_2R^{III}$;

$R^I$ is H, $C_1$-$C_4$ alkyl, $C_2$-$C_3$ cyanoalkyl, methoxy or ethoxy;

$R^{II}$ is H, $C_1$-$C_4$ alkyl or $C_3$-$C_4$ alkenyl; or $R^I$ and $R^{II}$ may be taken together as —$(CH_2)_3$—, —$(CH_2)_4$—, —$(CH_2)_5$ or —$CH_2CH_2OCH_2CH_2$—;

$R^{III}$ is $C_1$-$C_4$ alkyl, $C_3$-$C_4$ alkenyl, $C_3$-$C_4$ alkynyl, $C_2$-$C_4$ haloalkyl, $C_1$-$C_3$ cyanoalkyl, $C_5$-$C_6$ cycloalkyl, $C_4$-$C_7$ cycloalkylalkyl or $C_2$-$C_4$ alkoxyalkyl;

A is

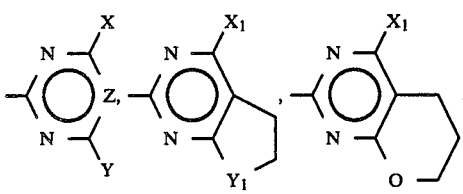

A-1 , A-2 , A-3 ,

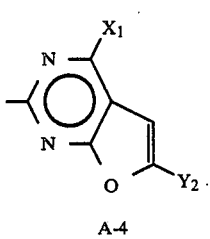

A-4

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino or di($C_1$-$C_3$ alkyl)amino;

Y is H, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino, di($C_1$-$C_3$-alkyl)amino, $C_3$-$C_4$ alkenyloxy, $C_3$-$C_4$ alkynyloxy, $C_2$-$C_5$ alkylthioalkyl, $C_1$-$C_4$ haloalkyl, $C_3$-$C_5$ cycloalkyl, $C_2$-$C_4$ alkynyl,

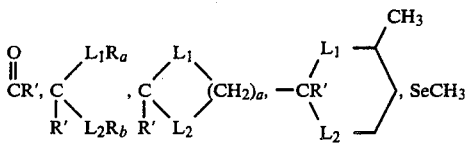

or $N(OCH_3)CH_3$;

a is 2 or 3;

$L_1$ is O or S;

$L_2$ is O or S;

$R_a$ is $C_1$-$C_2$ alkyl;

$R_b$ is $C_1$-$C_2$ alkyl;

R' is H or $CH_3$;

Z is CH;

$Y_1$ is $CH_2$ or O;

$X_1$ is $CH_3$, $OCH_3$, $OCH_2CH_3$ or $OCF_2H$;

$Y_2$ is H or $CH_3$;

(1) provided that when X is Cl, F or Br, then Y is $OCH_3$, $OCH_2CH_3$, $NH_2$, $NHCH_3$, $N(CH_3)_2$ or $OCF_2H$;

(2) when Y is $SeCH_3$, then X is $CH_3$, $OCH_3$, $OCH_2CH_3$, $OCF_2H$ or $CF_3$; and (3) when $R_2$ is $SeR_1$ or $CO_2R^{III}$, then it is attached to position 6 of J-1.

2. A compound of claim 1 where:

$R_2$ is H, F, Cl, Br, $CH_3$, $CF_3$, $OCH_3$, $SCH_3$, $OCF_2H$ or $SCF_2H$;

X is $CH_3$, $OCH_3$, $OCH_2CH_3$, Cl, F, Br, $OCF_2H$, $CH_2F$ or $CF_3$; and

Y is H, $C_1$-$C_3$ alkyl, cyclopropyl, $OCH_3$, $OCH_2CH_3$, $CH_2OCH_3$, $SeCH_3$, $CH_2OCH_2CH_3$, $NH_2$, $NHCH_3$, $N(CH_3)_2$, $CF_3$, $SCH_3$, $OCH_2CH=CH_2$, $OCH_2C\equiv CH$, $OCH_2CF_3$, $OCH_2CH_2OCH_3$, $CH_2SCH_3$, $OCF_2H$, $SCF_2H$,

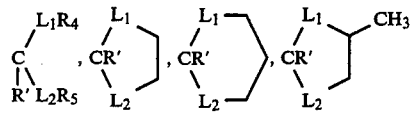

or $CR'(QCH_2CH_3)_2$.

3. A compound of claim 2 where A is A-1.

4. A compound of claim 3 where Y is $C_1$-$C_3$ alkyl, cyclopropyl, $OCH_3$, $OCH_2CH_3$, $CH_2OCH_3$, $CH_2OCH_2CH_3$, $OCH_2CF_3$ or $CH(OCH_3)_2$.

5. A compound of claim 4 where R is H and $R_1$ is $CH_3$ or $CH_2CH_3$.

6. A compound of claim 5 where H is J-1 and $R_2$ is H.

7. The compound of claim 1 which is N-[(4,6-dimethxypyrimidin-2-yl)aminocarbonyl]-2-(methylselenyl)benzenesulfonamide.

8. A composition suitable for controlling the growth of undesired vegetation which comprises a herbicidally effective amount of a compound of claim 1 and at least one of the following: surfactant, solid or liquid diluent.

9. A composition suitable for controlling the growth of undesired vegetation which comprises a herbicidally effective amount of a compound of claim 4 and at least one of the following: surfactant, solid or liquid diluent.

10. A composition suitable for controlling the growth of undesired vegetation which comprises a herbicidally effective amount of a compound of claim 5 and at least one of the following: surfactant, solid or liquid diluent.

11. A composition suitable for controlling the growth of undesired vegetation which comprises a herbicidally effective amount of a compound of claim 6 and at least one of the following: surfactant, solid or liquid diluent.

12. A method for the control of undesired vegetation which comprises applying to the locus of the undesired vegetation a herbicidally effective amount of a compound of claim 1.

13. A method for the control of undesired vegetation which comprises applying to the locus of the undesired vegetation a herbicidally effective amount of a compound of claim 4.

14. A method for the control of undesired vegetation which comprises applying to the locus of the undesired vegetation a herbicidally effective amount of a compound of claim 5.

15. A method for the control of undesired vegetation which comprises applying to the locus of the undesired vegetation a herbicidally effective amount of a compound of claim 6.

* * * * *